United States Patent
Bestor et al.

(10) Patent No.: US 10,337,049 B2
(45) Date of Patent: Jul. 2, 2019

(54) UNIVERSAL METHYLATION PROFILING METHODS

(71) Applicants: Timothy H. Bestor, New York, NY (US); Jingyue Ju, Englewood Cliffs, NJ (US); Xiaoxu Li, New York, NY (US); James J. Russo, New York, NY (US)

(72) Inventors: Timothy H. Bestor, New York, NY (US); Jingyue Ju, Englewood Cliffs, NJ (US); Xiaoxu Li, New York, NY (US); James J. Russo, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 448 days.

(21) Appl. No.: 14/973,637

(22) Filed: Dec. 17, 2015

(65) Prior Publication Data

US 2016/0355542 A1    Dec. 8, 2016

Related U.S. Application Data

(63) Continuation-in-part of application No. PCT/US2014/042567, filed on Jun. 16, 2014.
(Continued)

(51) Int. Cl.
| | | |
|---|---|---|
| *C12Q 1/68* | (2018.01) | |
| *C12Q 1/6806* | (2018.01) | |
| *C07H 19/16* | (2006.01) | |
| *C07H 19/167* | (2006.01) | |
| *C12Q 1/6874* | (2018.01) | |
| *C12N 9/10* | (2006.01) | |

(Continued)

(52) U.S. Cl.
CPC ........... *C12Q 1/6806* (2013.01); *C07H 19/16* (2013.01); *C07H 19/167* (2013.01); *C12N 9/1007* (2013.01); *C12P 19/34* (2013.01); *C12Q 1/6827* (2013.01); *C12Q 1/6874* (2013.01); *C12Y 201/01* (2013.01)

(58) Field of Classification Search
CPC .................................................. C12Q 1/6806
USPC ........................................................ 435/6.1
See application file for complete search history.

(56) References Cited

U.S. PATENT DOCUMENTS

| | | |
|---|---|---|
| 3,726,821 A | 4/1973 | Chiu et al. |
| 4,267,171 A | 5/1981 | Bergstrom et al. |

(Continued)

FOREIGN PATENT DOCUMENTS

| | | |
|---|---|---|
| EP | 1 712 557 A1 | 10/2006 |
| EP | 2 053 131 A1 | 4/2009 |

(Continued)

OTHER PUBLICATIONS

International Search Report mailed by the International Searching Authority (ISA/US) dated Sep. 16, 2009 in connection with PCT International Application No. PCT/US2009/04257.
(Continued)

*Primary Examiner* — Jezia Riley
(74) *Attorney, Agent, or Firm* — John P. White; Cooper & Dunham LLP

(57) ABSTRACT

The present invention provides a method of determining whether cytosine residues present at a predetermined positions within a single strand of a double stranded DNA of known sequence are methylated as well as compounds for carrying out this method.

14 Claims, 35 Drawing Sheets

Specification includes a Sequence Listing.

Related U.S. Application Data

(60) Provisional application No. 61/836,060, filed on Jun. 17, 2013, provisional application No. 62/094,850, filed on Dec. 19, 2014.

(51) Int. Cl.
*C12P 19/34* (2006.01)
*C12Q 1/6827* (2018.01)

(56) References Cited

U.S. PATENT DOCUMENTS

| | | | |
|---|---|---|---|
| 5,032,594 | A | 7/1991 | Takehiko et al. |
| 5,824,669 | A | 10/1998 | Garvey et al. |
| 6,049,329 | A | 4/2000 | Prusse et al. |
| 6,214,556 | B1 | 4/2001 | Olek et al. |
| 6,268,132 | B1 | 7/2001 | Conrad |
| 7,794,939 | B2 | 9/2010 | Maki et al. |
| 9,738,922 | B2 | 8/2017 | Bestor et al. |
| 2003/0114402 | A1 | 6/2003 | Reich et al. |
| 2006/0019270 | A1 | 1/2006 | Yang et al. |
| 2006/0172988 | A1 | 8/2006 | Johansson et al. |
| 2007/0161007 | A1 | 7/2007 | Rajski et al. |
| 2008/0103053 | A1 | 5/2008 | Siddiqi et al. |
| 2008/0175814 | A1 | 7/2008 | Phiasivongsa et al. |
| 2009/0018101 | A1 | 1/2009 | Weinhold et al. |
| 2011/0033708 | A1 | 2/2011 | Harimoto et al. |
| 2012/0208711 | A1 | 8/2012 | Cortese |

FOREIGN PATENT DOCUMENTS

| | | |
|---|---|---|
| WO | WO 1997/028177 | 8/1997 |
| WO | WO 2003/031648 A2 | 4/2003 |
| WO | WO 2005/121361 A2 | 12/2005 |
| WO | WO 2009/078876 A1 | 6/2009 |
| WO | WO 2014/204861 A1 | 12/2014 |
| WO | 2018/187382 A1 | 11/2018 |

OTHER PUBLICATIONS

Written Opinion of the International Searching Authority issued by the International Searching Authority (ISA/US) dated Sep. 16, 2009 in connection with PCT International Application No. PCT/US2009/004257, filed Feb. 17, 2010.
International Search Report mailed by the International Searching Authority (ISA/US) dated Oct. 7, 2014 in connection with PCT International Application No. PCT/US2014/042567, filed Jun. 16, 2014.
Written Opinion of the International Searching Authority issued by the International Searching Authority (ISA/US) dated Oct. 7, 2014 in connection with PCT International Application No. PCT/US2014/042567, filed Jun. 16, 2014.
International Search Report mailed by the International Searching Authority (ISA/US) dated Apr. 22, 2016 in connection with PCT International Application No. PCT/US2015/066771, filed Dec. 18, 2015.
Written Opinion of the International Searching Authority issued by the International Searching Authority (ISA/US) dated Apr. 22, 2016 in connection with PCT International Application No. PCT/US2015/066771, filed Dec. 18, 2015.
Jan. 7, 2013 Office Action issued in connection with U.S. Appl. No. 13/055,208.
Jul. 8, 2013 Response dated Jan. 7, 2013 Office Action issued in connection with U.S. Appl. No. 13/055,208.
Mar. 17, 2014 Response dated Jan. 15, 2014 Notice of Non-Responsive Amendment issued in connection with U.S. Appl. No. 13/055,208.
Jun. 24, 2014 Office Action issued in connection with U.S. Appl. No. 13/055,208.
May 20, 2015 Office Action issued in connection with U.S. Appl. No. 14/578,125.
Aug. 19, 2015 Response dated May 20, 2015 Office Action issued in connection with U.S. Appl. No. 14/578,125.
Oct. 14, 2015 Office Action issued in connection with U.S. Appl. No. 14/578,125.
Dec. 2, 2015 response dated Oct. 14, 2015 Office Action issued in connection with U.S. Appl. No. 14/578,125.
Extended European Search Report dated Mar. 4, 2012 in connection with European Patent Application No. 09800674.5.
PubChem Compound Summary for CID446104, available online at <https://pubchem.ncbi.nlm.nih.gov/summary/summary.cgi?loc=ec_rcs&cid=446104>.
PUBCHEM. CID12641134. Feb. 8, 2007, pp. 1-2 [online], (retrieved on Dec. 12, 2017]. Retrieved from the Internet <URL:http://pubchem.ncbi.nlm.nih.gov/summary/summary.cgi?cid=12641134>; p. 1, formula.
PUBCHEM, Substance Record for SID 34950751, Create Date: Dec. 5, 2007. [retrieved on Dec. 13, 2017]. Retrieved from the internet <https://pubchem.ncbi.nlm.nih.gov/substance/34950751/version/1#section=Top >.
National Center for Biotechnology Information. PubChem Substance Database; SID=236517547, https://pubchem.ncbi.nlm.nih.gov/substance/236517547 (accessed Dec. 19, 2017).
National Center for Biotechnology Information. PubChem Substance Database; SID=236528318, https://pubchem.ncbi.nlm.nih.gov/substance/236528318 (accessed Dec. 19, 2017).
National Center for Biotechnology Information. PubChem Substance Database; SID=52332545, https://pubchem.ncbi.nlm.nih.gov/substance/52332545 (accessed Dec. 19, 2017).
Ansorge, Wilhelm. Next-generation DNA sequencing techniques. New biotechnology. 25. 195-203. (2009) (abstract).
Benjamin Chanrion, Yurong Xin and Fatemeh Haghighi, Enzymatic Approaches for Genome DNA Methylation Profiling From Epigenetics: A Reference Manual (Edited by: Jeffrey M. Craig and Nicholas C. Wong). Caister Academic Press, U.K. (2011) (abstract).
Dalhoff C et al. (2006a) Direct transfer of extended groups from synthetic cofactors by DNA methyltransferases. Nat. Chem. Biol. 2:31-32.
Dalhoff C et al. (2006b) Synthesis of S-adenosyl-L-methionine analogs and their use for sequence-specific transkylation of DNA by methyltransferases. Nat. Protoc. 1, 1879-86.
Grunau et al. Bisulfite genomic sequencing: a systematic investigation of critical experimental parameters. Nucleic Acid Research, 2001, vol. 29, No. 13 e65 [abstract].
Islam et al. Defining efficient enzyme-cofactor pairs for bioorthogonal profiling of protein methylation. PNAS 110(42): 16778-16783, 2013.
Jones, PA, et al. Cellular Differentiation, Cytidine Analogs and DNA Methylation. Cell, vol. 20, No. 1, May 1980, pp. 85-93 [online abstract], abstract.
Laird, Peter W. Principles and challenges of genome-wide DNA methylation analysis. Nature Reviews Genetics 11, 191-203 (2010) (abstract).
Lukinavic G et al. Targeted labeling of DNA by Methyltransferase-Directed Transfer of Activated Groups (mTAG). Journal of the American Chemical Society. 129, 10 (2007) 2758-2759.
Takiguchi, Metal. Effects of Cadmium on DNA-(Cytosine-5) Methyltransferase Activity and DNA Methylation Status During Cadmium-Induced Cellular Transformation. Experimental Cell Research, vol. 286, 2003, pp. 355-365.
Vilkaitis, G et al. The Mechanism of DNA Cytosine-5 Methylation. Journal of Biological Chemistry 2001, vol. 276, pp. 20924-20934 A172.
Xu, M. et al. Cloning, Characterization and Expression at the Gene Coding for a Cytosine-5-DNA Methyltransferase Recognizing GpC. Nucleic Acids Research, vol. 26, No. 17, 1998, pp. 3961-3966.
Yehua Yang, Molecular Genetics, p. 61-64, China Agricultural Press, Mar. 31, 2001.
Zhang X et al. Genome-wide high-resolution mapping and functional analysis of DNA methylation in *Arabidopsis*. Cell. Sep. 22, 2006;126(6):1189-201. Epub Aug. 31, 2006.
Extended European Search Report dated May 7, 2018 in connection with European Patent Application No. 15871195.2.

(56) References Cited

OTHER PUBLICATIONS

Dec. 4, 2018 Response to Extended European Search Report dated May 7, 2018 in connection with European Patent Application No. 15871195.2.

Darii, M.V., et al. Isolation and site—directed mutagenesis of DNA methyltransferase SssI. Mol Biol (2007) 41: 110.

Kriukienė E, et al. "DNA unmethylome profiling by covalent capture of CpG sites" Nature Communications, 4 (2013): 2190.

Renbaum et al. "Cloning, characterization, and expression in *Escherichia coli* of the gene coding for the CpG DNA methylase from *Spiroplasma* sp. strain MQ1(M.SssI)" *Nucleic acids research* vol. 18,5 (1990): 1145-52.

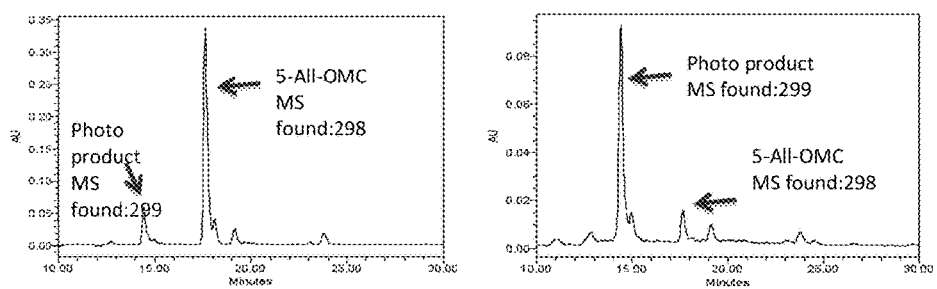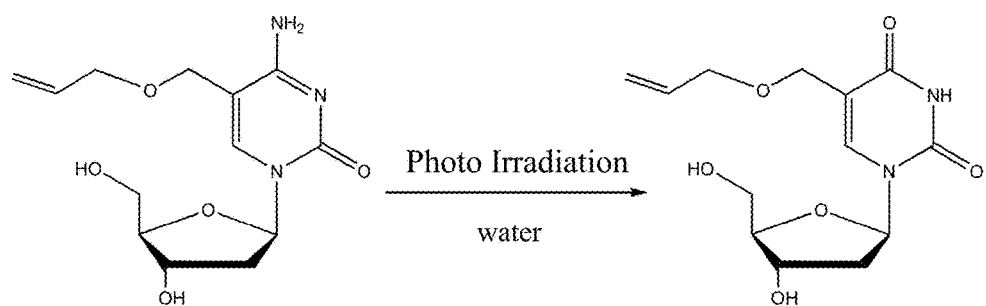
Fig. 3

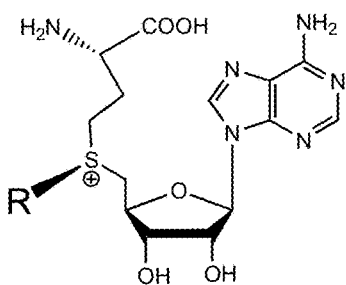
R:
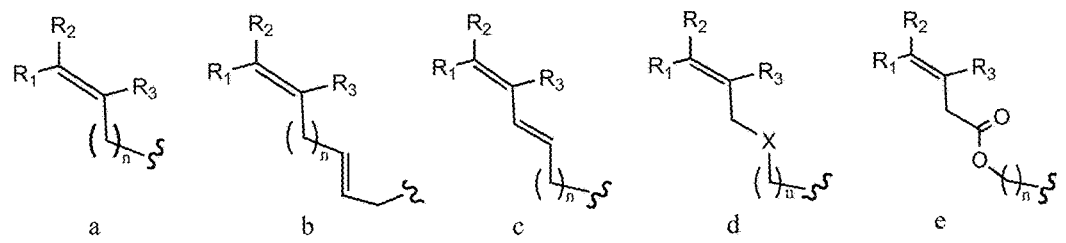
a    b    c    d    e
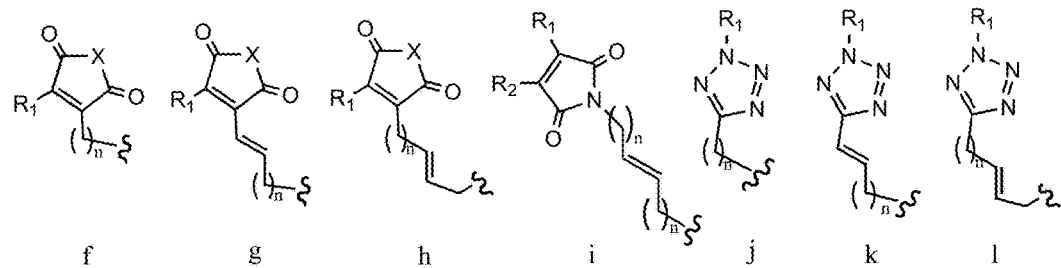
f    g    h    i    j    k    l
Fig. 8

Example A
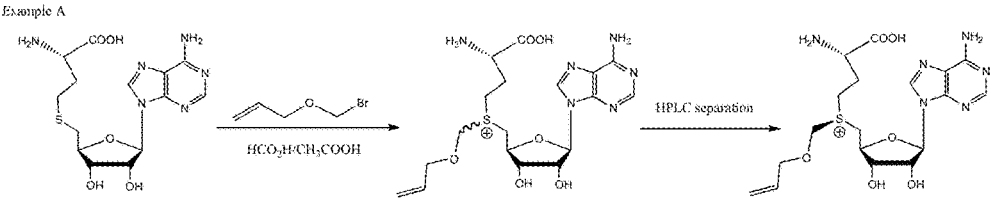
Example B
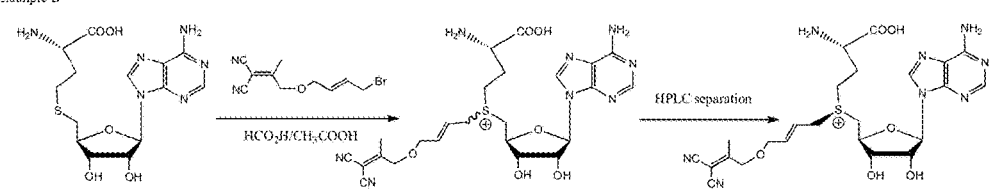
Example C
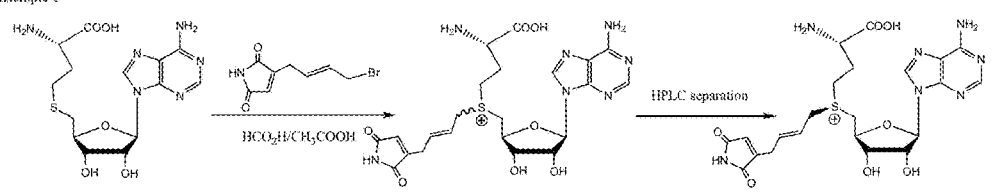
Fig. 9

Example A
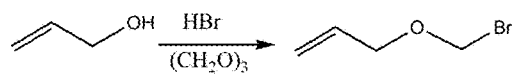
Example B
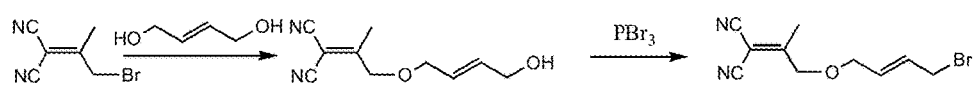
Example C
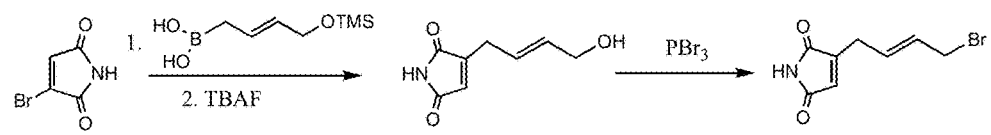
Fig. 10

| Name | Amino Acid | | Designed |
|---|---|---|---|
| WT | 142 Q | 370 N | No |
| SS | 142 S | 370 S | Yes |
| SA | 142 S | 370 A | Yes |
| AS | 142 A | 370 S | Yes |
| AA | 142 A | 370 A | Yes |
| QS | 142 Q | 370 S | Yes |
| QA | 142 Q | 370 A | Yes |
| SN | 142 S | 370 N | No |
| AN | 142 A | 370 N | No |

Fig. 17

Oligos to synthesize:

5'-A?CACGGA?AC?A??AACTGACC??AGACT?????????AT?AT??TACT-3' SEQ ID NO: 33

5'-AGTACGGATCCATCCCC?A?T????????T?AGTCCTAC?TAGCCGCT-3' SEQ ID NO: 34

Anneal

5'-A?CACGGA????????AACTGACC??AGACT???????????ATCACCGTACT-3' SEQ ID NO: 35
3'-TCGTGCCTA?????????TCCTTGACT????????????????TACCTAGGCATGA-5' SEQ ID NO: 36

Irradiate

5'-AGCACGGAT?????????AACTGACC???????????????ATGATCCGTACT-3' SEQ ID NO: 37
3'-TCGTGCCTA???????????CCTTGACT???????????????TACCTAGGCATGA-5' SEQ ID NO: 38

Amplify

5'-AGCACGGA?????????AACTGA?????????????????ATGGATCCGTACT-3' SEQ ID NO: 39
3'-??????????????????CCTTGACT?TCTGACC??????TACCTAGGCATGA-5' SEQ ID NO: 40

GEL ← Hpall / SmaBI       Bfol / SmaBI → GEL
         MALDI                 MALDI

Fig. 20

A.
Fig. 34
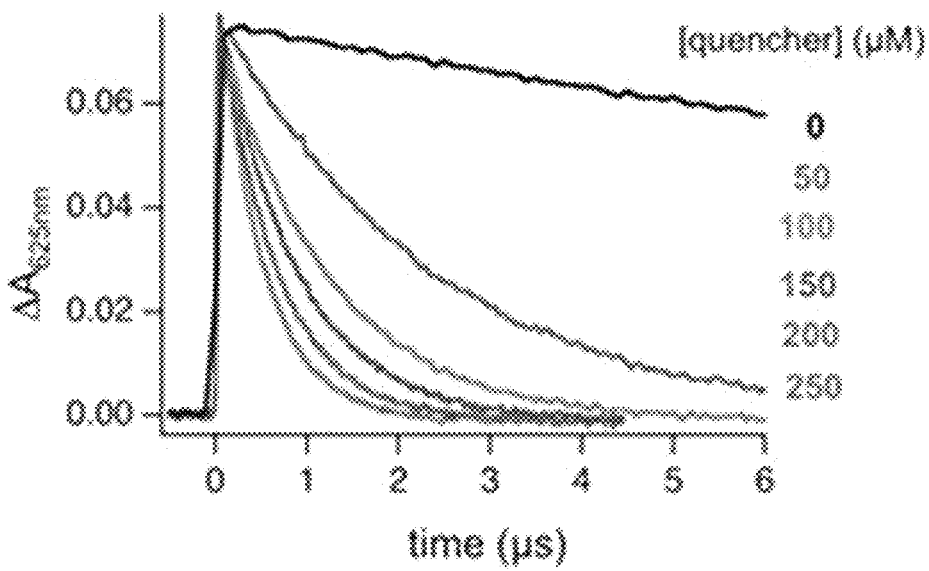
B.
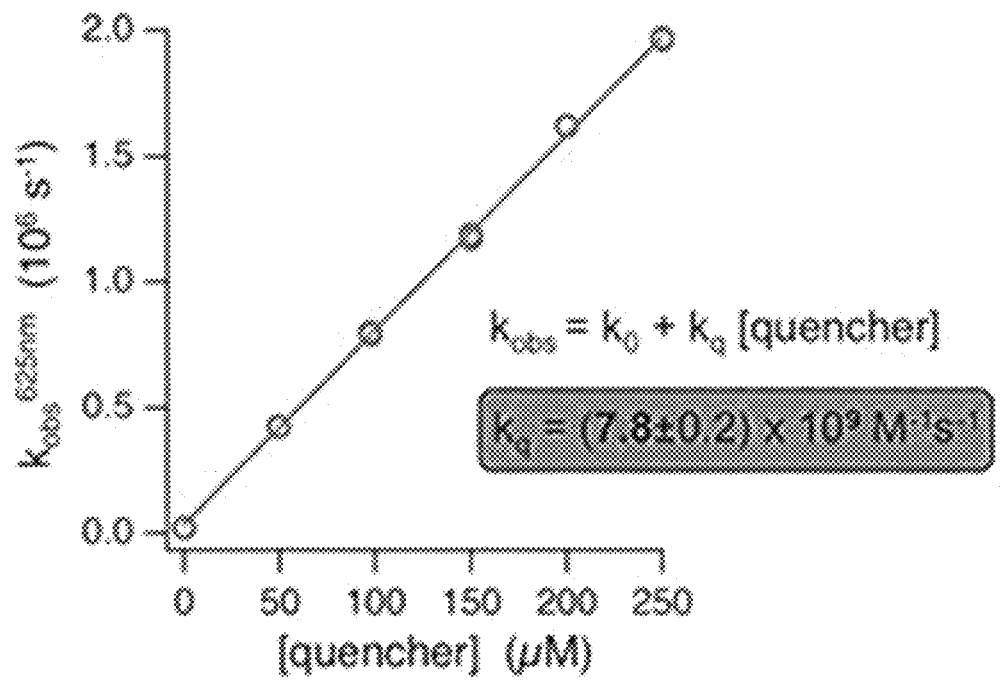

Fig. 35

| Protein | Substitutions | 142nd Codon | 370th Codon |
|---|---|---|---|
| WT (no His-Tag) | NA | TTCCTTGTCAAGACT SEQ ID NO. 18 | TTTGTGGAAATTCAA SEQ ID NO.19 |
| SS | Q142S/N370S (CA578TC/AG1261GT) | TTCCTTGTTCAGACTT SEQ ID NO. 20 | TTTGTGGAAGTTCAA SEQ ID NO. 21 |
| SA | Q142S/N370A (CA578TC/AG1261GC) | TTCCTTGTTCAGACTT SEQ ID NO. 22 | TTTGTGGAGCTTCAA SEQ ID NO. 23 |

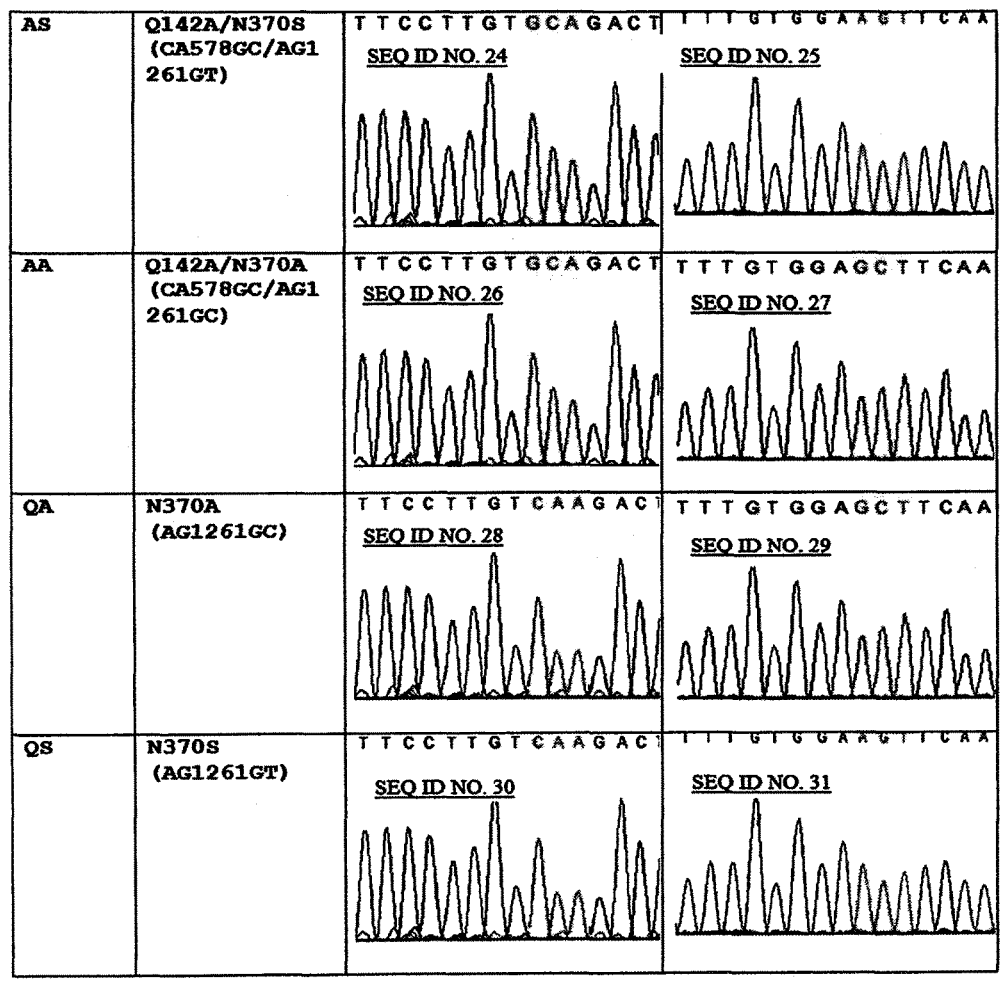
(Fig. 35 continued)

UNIVERSAL METHYLATION PROFILING METHODS

CROSS-REFERENCE TO RELATED APPLICATIONS

This application is a continuation-in-part of PCT International Application No. PCT/US2014/042567, filed Jun. 16, 2014, claiming the benefit of U.S. Provisional Application No. 61/836,060, filed Jun. 17, 2013; and claiming the benefit of U.S. Provisional Application No. 62/094,850, filed Dec. 19, 2014, the contents of each of which are hereby incorporated by reference in their entirety.

REFERENCE TO SEQUENCE LISTING

This application incorporates-by-reference nucleotide and/or amino acid sequences which are present in the file named "160808_85014-C_Sequence_Listing_JTC.txt," which is 9 kilobytes in size, and which was created Aug. 9, 2016 in the IBM-PC machine format, having an operating system compatibility with MS-Windows, which is contained in the text file filed Aug. 9, 2016 as part of this application.

Throughout this application, various publications are referenced. Full citations for these references are present immediately before the claims. The disclosures of these publications in their entireties are hereby incorporated by reference into this application to more fully describe the state of the art to which this invention pertains.

BACKGROUND OF THE INVENTION

DNA methylation is an important epigenetic mechanism having several regulatory functions such as X-chromosome inactivation, genomic imprinting, and suppression of retrotransposition (Goll and Bestor 2005). This process of methylation involves the transfer of a methyl group from S-adenosyl L-methionine (AdoMet) to the C5 carbon of a cytosine (C) by an enzyme called DNA methyltransferase (Mtases) to produce 5-methylcytosine (5mC) (Goll and Bestor, 2005). The human genome contains ~28 million CpG sites, about 70% of which are methylated at the 5 position of the cytosine (Edwards at al., 2010). Aberrant or abnormal DNA methylation has been linked to a growing number of human diseases including Immunodeficiency, Centromere instability and Facial anomalies (ICF) syndrome, fragile X syndrome, and other developmental diseases, age-related neurodegenerative disorders, diabetes and cancer (Robertson et al., 2005; reviewed by Goll and Bestor, 2005). Hence, epigenetic changes in DNA methylation status are increasingly being studied for their role in both normal and disease-associated phenotypic changes, including the Roadmap Epigenomics Project launched by NIH to create reference epigenomes for a variety of cell types. To fulfill this goal, genome-wide methods and techniques that can comprehensively profile DNA methylation status with single base resolution and high throughput are essential (Suzuki et al., 2008, Laird, 2010).

Over 30 methylation analysis technologies have been developed, but all have shortcomings (Laird, 2010). Bisulfite genomic sequencing (BGS), reported by Susan Clark and Marianne Frommer in 1994 (Clark et al., 1994), is regarded as the best available method. However, BGS has several serious shortcomings: (1) there is a severe loss of sequence information upon bisulfite conversion which produces sequences that cannot be aligned to the genome; (2) strong biases against GC-rich sequences (Edwards et al., 2010); (3) bisulfite conversion artifacts, and (4) the need for large amounts of long starting DNA due to high rates of strand cleavage under the harsh reaction conditions (Warnecke et al., 2002, 1997). In spite of the development of over 30 technologies that enable identification of the methylation status of DNA (methylome analysis), the determination of whole-genome methylation patterns remains difficult and expensive (Clark et al., 1994). Major improvements or new approaches overcoming the above mentioned limitations are needed to further advance genome-wide DNA methylation profiling.

SUMMARY OF THE INVENTION

The present invention provides a compound having the structure:

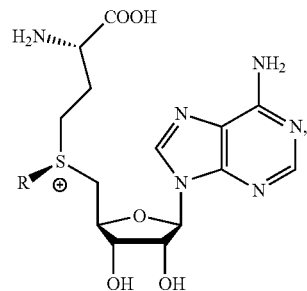

wherein R is

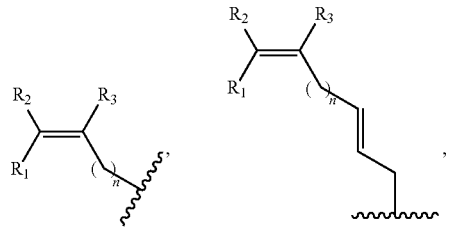

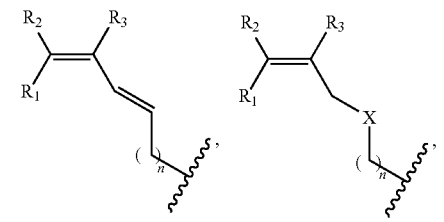

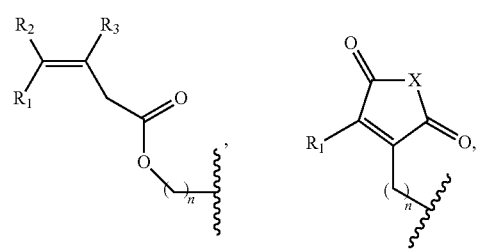

-continued

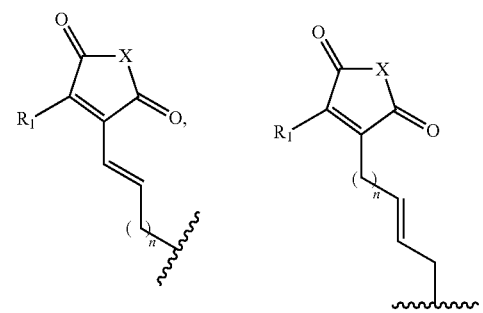

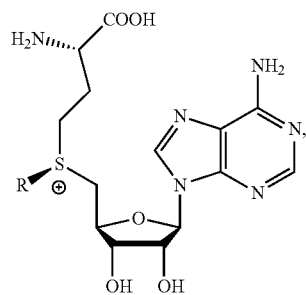

wherein R is

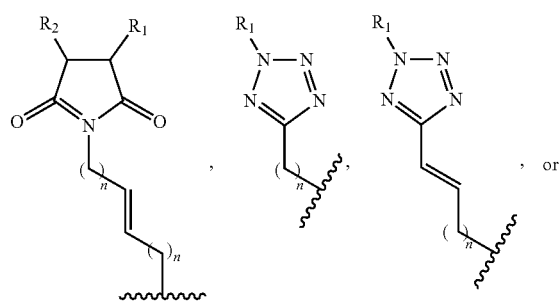

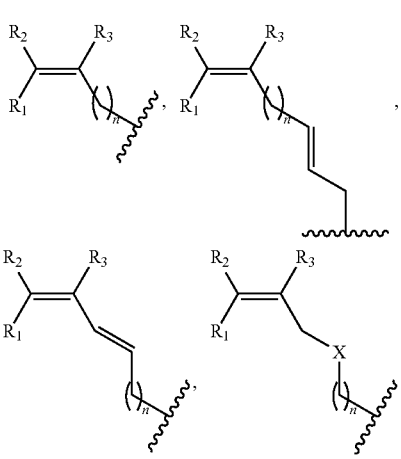

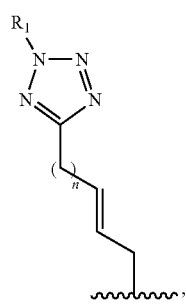

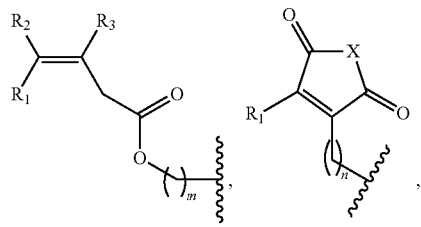

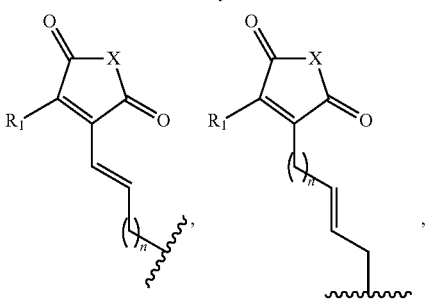

wherein $R_1$, $R_2$ and $R_3$ are independently H, alkyl, aryl, $C(O)NH_2$, $C(O)R'$, CN, $NO_2$, $C(O)R'$, $S(O)_2NHR'$;
wherein X is O or NR';
wherein R' is H, alkyl or aryl; and
wherein n is an integer from 1 to 8,
with the proviso that, when R is

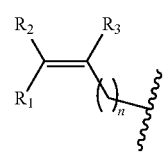

and n is 1, at least one of $R_1$, $R_2$ or $R_3$ is other than H.

The present invention also provides a composition of matter comprising a compound having the structure:

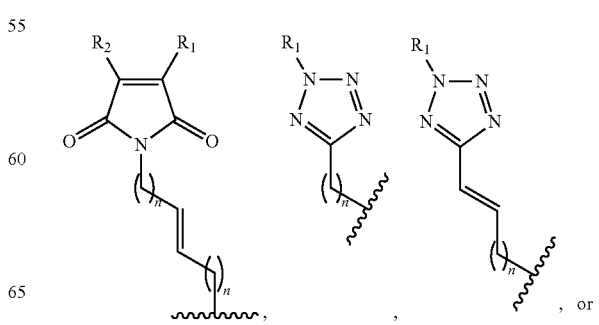

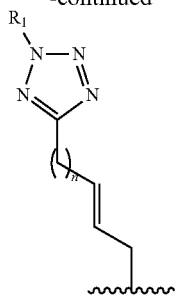

wherein $R_1$, $R_2$ and $R_3$ are independently H, alkyl, aryl, C(O)NH$_2$, C(O)R', CN, NO$_2$, C(O)R', S(O)$_2$NHR';
wherein X is O or NR';
wherein R' is H, alkyl or aryl; and
wherein n is an integer from 1 to 8,
with the proviso that, when R is

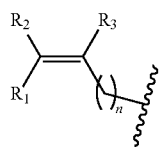

and n is 1, at least one of $R_1$, $R_2$ or $R_3$ is other than H, attached to a CpG methyltransferase.

The present invention also provides a process of producing a derivative of a double-stranded DNA comprising contacting the double-stranded DNA with a CpG methyltransferase and an S-adenosylmethionine analog having the structure:

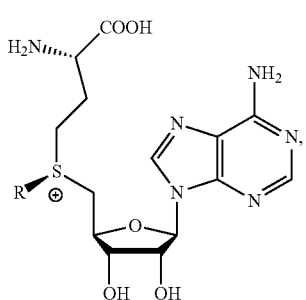

wherein R is a chemical group capable of being transferred from the S-adenosylmethionine analog by the CpG methyltransferase to a 5-carbon of a non-methylated cytosine of the double-stranded DNA, under conditions such that the chemical group covalently binds to the 5-carbon of the non-methylated cytosine of the double-stranded DNA, and thereby produces the derivative of the double-stranded DNA, wherein the chemical group has the structure:

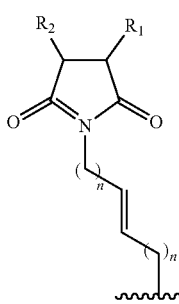 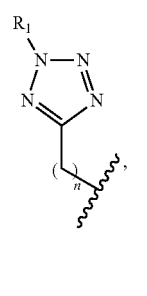

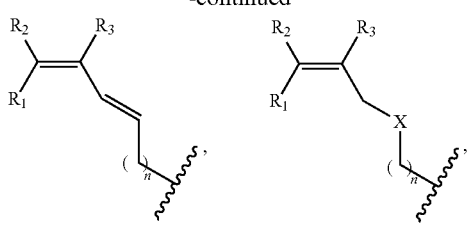

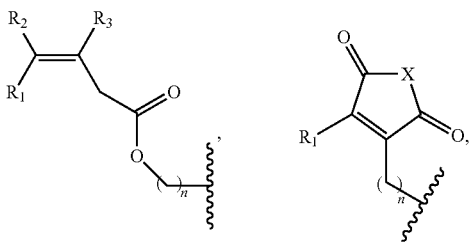

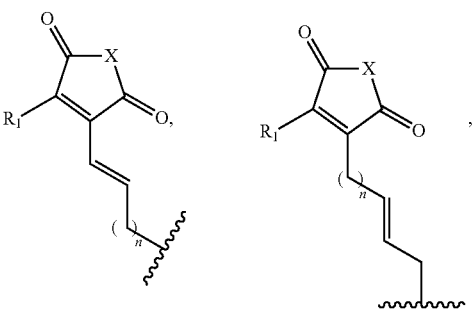

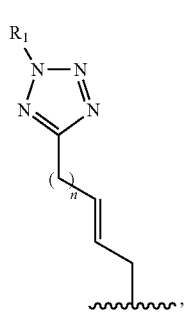

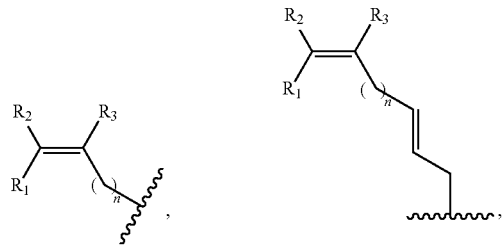

wherein $R_1$, $R_2$ and $R_3$ are independently H, alkyl, aryl, C(O)NH$_2$, C(O)R', CN, NO$_2$, C(O)R', S(O)$_2$NHR';
wherein X is O or NR';
wherein R' is H, alkyl or aryl; and
wherein n is an integer from 1 to 8, with the proviso that, when R is

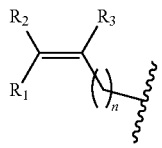

and n is 1, at least one of $R_1$, $R_2$ or $R_3$ is other than H.

The present invention also provides a method of determining whether a cytosine present within a double-stranded DNA sequence of known sequence is non-methylated comprising:

a) producing a derivative of the double-stranded DNA by contacting the double-stranded DNA with a CpG methyltransferase and an S-adenosylmethionine analog having the structure:

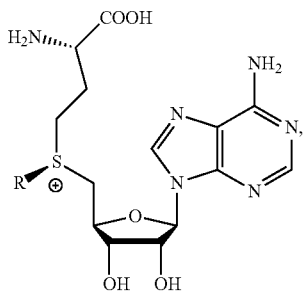

wherein R is a chemical group capable of being transferred from the S-adenosylmethionine analog by the CpG methyltransferase to a 5 carbon of a non-methylated cytosine of the double-stranded DNA so as to covalently bond the chemical group to the 5 carbon of the non-methylated cytosine of the double-stranded DNA, thereby making a derivatized double stranded DNA, wherein the chemical group has the structure:

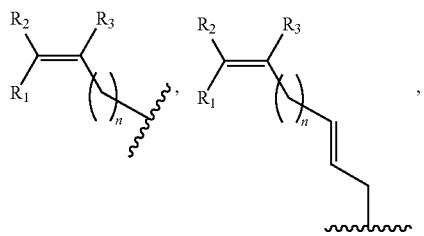

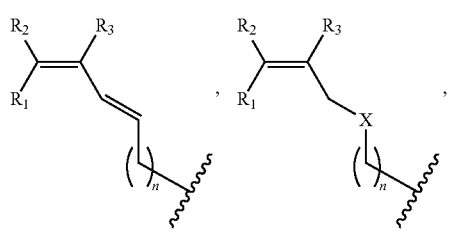

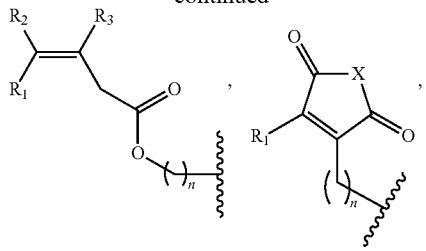

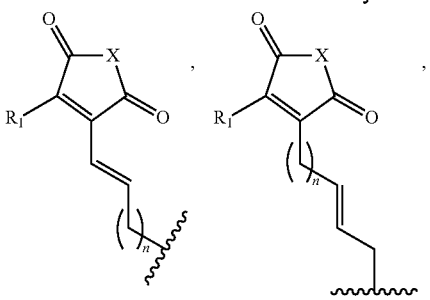

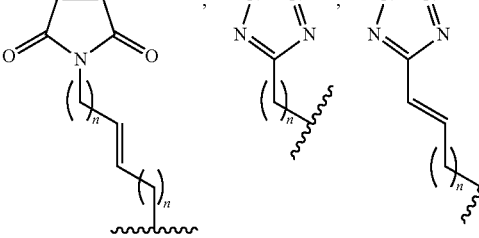

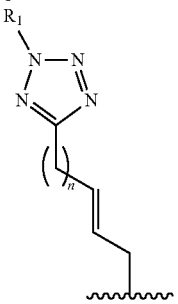

wherein $R_1$, $R_2$ and $R_3$ are independently H, alkyl, aryl, $C(O)NH_2$, $C(O)R'$, CN, $NO_2$, $C(O)R'$, $S(O)_2NHR'$;
wherein X is O or NR';
wherein R' is H, alkyl or aryl; and
wherein n is an integer from 1 to 8;

b) producing a U analogue by photo-conversion of the derivative produced in step a);
c) separately obtaining a single strand of the derivative of the double-stranded DNA;
d) sequencing the single strand so obtained in step c); and
e) comparing the sequence of the single strand determined in step d) to the sequence of a corresponding strand of the double-stranded DNA of which a derivative has not been produced, wherein the presence of a uracil analog in the single strand of the derivative single strand instead of a cytosine at a predefined position in the corresponding strand of the double-stranded DNA of which a derivative has not been produced indicates that the cytosine at that position in the double-stranded DNA is non-methylated.

The present invention also provides a derivatized DNA molecule, wherein the derivatized DNA molecule differs from DNA by comprising a nucleotide residue which comprises a base having the following structure:

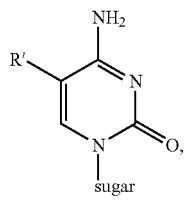

wherein R' is

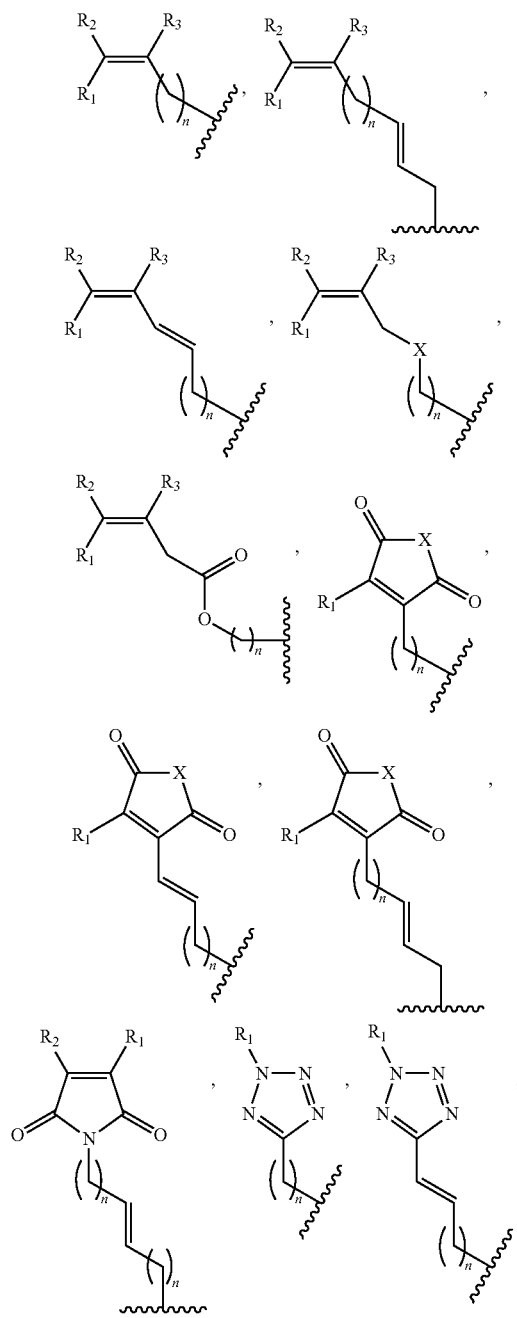

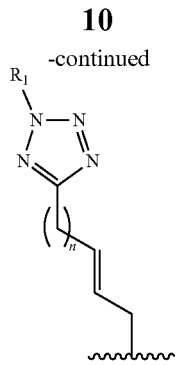

wherein $R_1$, $R_2$ and $R_3$ are independently H, alkyl, aryl, $C(O)NH_2$, $C(O)R''$, CN, $NO_2$, $C(O)R''$, $S(O)_2NHR''$;
wherein X is O or NR'';
wherein R'' is H, alkyl or aryl; and
wherein n is an integer from 1 to 8,
with the proviso that, when R' is

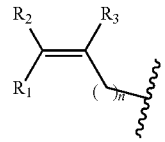

and n is 1, at least one of $R_1$, $R_2$ or $R_3$ is other than H,
and wherein the sugar is a sugar of the nucleotide residue.

The present invention also provides a derivatized DNA molecule, wherein the derivatized DNA molecule differs from DNA by comprising a nucleotide residue which comprises a base having the following structure:

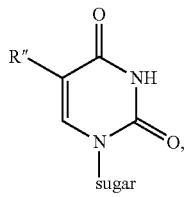

wherein R'' is

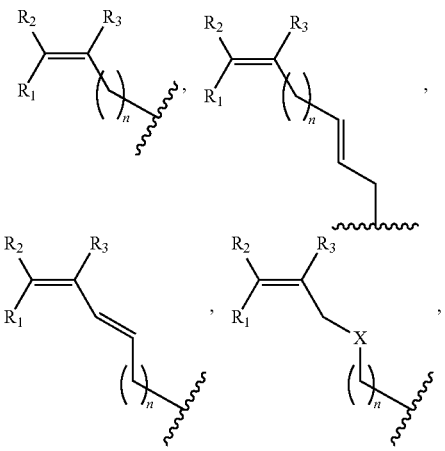

-continued

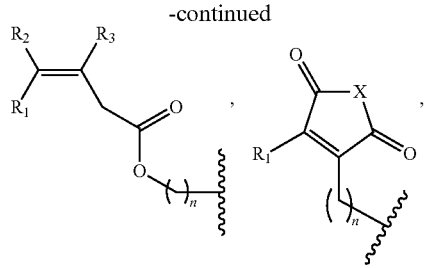,

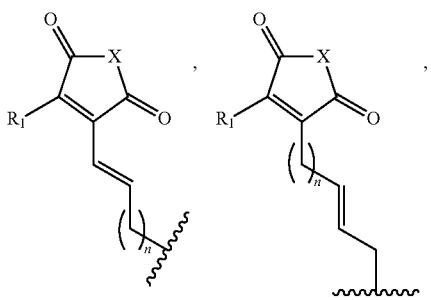,

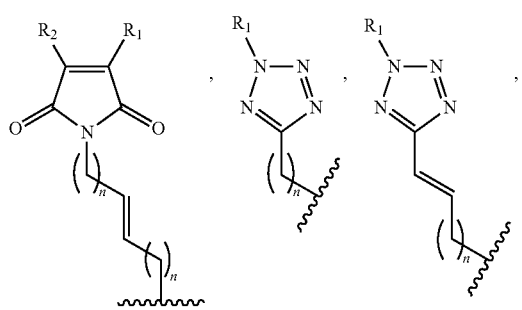,

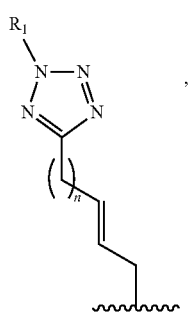, wherein $R_1$, $R_2$ and $R_3$ are independently H, alkyl, aryl, $C(O)NH_2$, $C(O)R'$, CN, $NO_2$, $C(O)R'$, $S(O)$ 2NHR';
wherein X is O or NR';
wherein R' is H, alkyl or aryl; and
wherein n is an integer from 1 to 8,
and wherein the sugar is a sugar of the nucleotide residue.

The present invention also provides a kit for derivatizing a double-stranded DNA molecule or for determining whether a cytosine present within a double-stranded DNA sequence of known sequence is non-methylated comprising:

a) a compound having the structure:

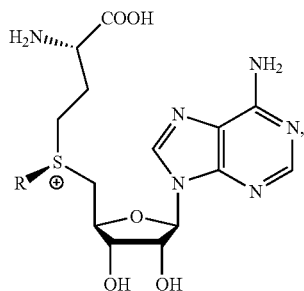

wherein R is

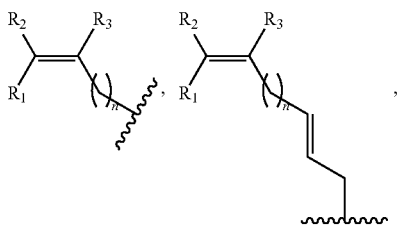

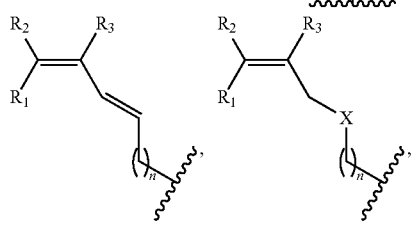

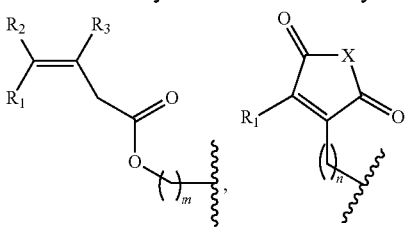

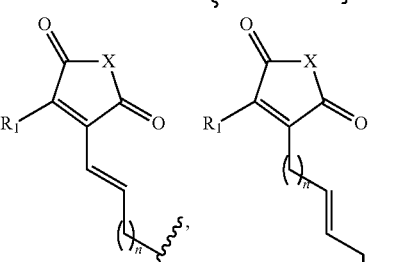

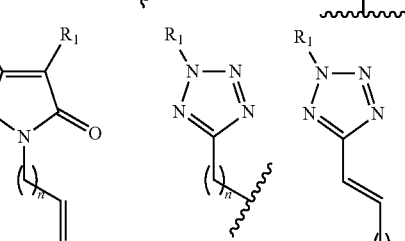, or

-continued

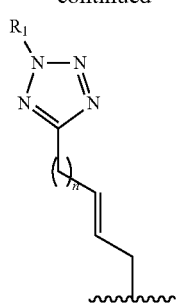

wherein $R_1$, $R_2$ and $R_3$ are independently H, alkyl, aryl, C(O)NH$_2$, C(O)R', CN, NO$_2$, C(O)R', S(O)$_2$NHR';

wherein X is O or NR';

wherein R' is H, alkyl or aryl; and wherein n is an integer from 1 to 8; and b) instructions for use.

The present invention also provides a method of determining whether a cytosine present within a double-stranded DNA sequence of known sequence is non-methylated comprising:

a) producing a derivative of the double-stranded DNA by contacting the double-stranded DNA with a CpG methyltransferase and an S-adenosylmethionine analog having the structure:

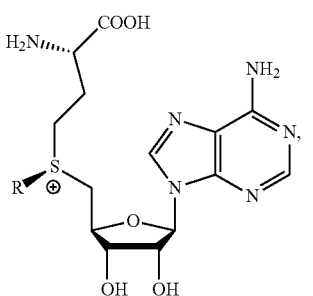

wherein R is a chemical group capable of being transferred from the S-adenosylmethionine analog by the CpG methyltransferase to a 5 carbon of a non-methylated cytosine of the double-stranded DNA so as to covalently bond the chemical group to the 5 carbon of the non-methylated cytosine of the double-stranded DNA, thereby making a derivatized double stranded DNA, wherein the chemical group has the structure:

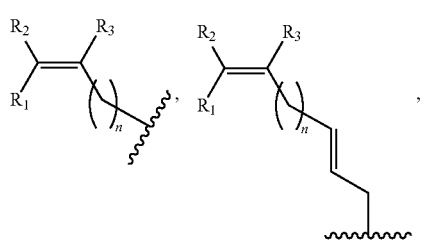

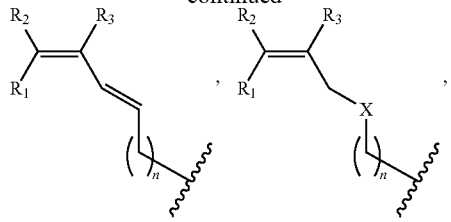

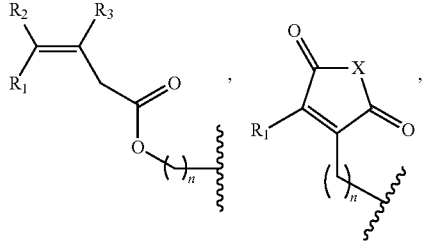

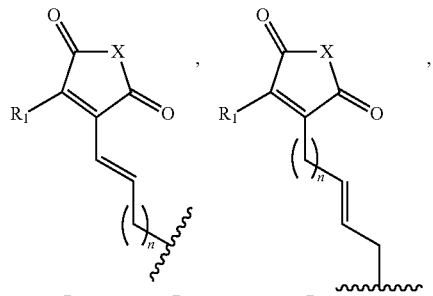

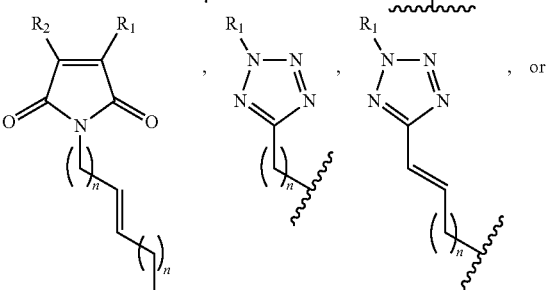

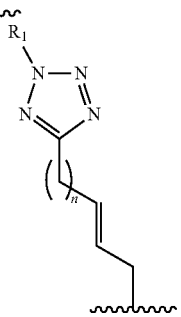

wherein $R_1$, $R_2$ and $R_3$ are independently H, alkyl, aryl, C(O)NH$_2$, C(O)R', CN, NO$_2$, C(O)R', S(O)$_2$NHR';

wherein X is O or NR';

wherein R' is H, alkyl or aryl; and wherein n is an integer from 1 to 8; and b) determining whether a cytosine at a predefined position in the double-stranded DNA has been modified with the chemical group R, wherein modification with the chemical group R on the cytosine at a predefined position in the double-stranded DNA indicates that the cytosine at that position in the double-stranded DNA is non-methylated.

BRIEF DESCRIPTION OF THE FIGURES

FIG. 3. HPLC profile during time course of photo-irradiation of 5-All-OMC. After 3 h of irradiation, the main peak is the starting material 5-All-OMC (MS-MW found 298) (Left). After 12 h photo-irradiation, the starting material is mostly consumed yielding a new product 5-All-OMU with MS-MW 299 (Right).

FIG. 8. Example structures of photoreactive moiety containing AdoMet analogs. $R_1$, $R_2$ and $R_3$ are independently H, alkyl, aryl, $C(O)NH_2$, $C(O)R'$, CN, $NO_2$, $C(O)R'$, $S(O)_2NHR'$; X is O or NR'; R' is H or alkyl; and n=1-8.

FIG. 9. Example synthetic schemes for photoreactive group-containing AdoMet analogs.

FIG. 10. Example synthetic schemes for the syntheses of bromide intermediates leading to the AdoMet analogs shown in FIG. 9.

FIG. 17. The His-tagged wild type and mutant variants that were designed or are in process of being generated.

FIG. 20. Photo-Conversion Assay. Oligonucleotides are synthesized bearing a photo-convertible 5-modified cytosine (C') on each strand within the context of the same CpG site. Prior to irradiation, or in the absence of photo-conversion to the U analog (U'), the site can be cut by the restriction enzyme HpaII following PCR amplification which results in replacement of the C' by a normal C. After photo-conversion, PCR will convert the resulting U' to a normal U, in which case the site can be cut with BfaI. Other restriction sites are included in the DNA to produce fragment sizes that allow easy discrimination of the bands on gels or the peaks obtained with mass spectroscopy.

FIG. 34. A. Decay traces of the transient absorbance of thioxanthone triplet monitored at 625 nm after pulsed laser excitation (355 nm, 5 ns pulse width) in argon saturated acetonitrile solutions in absence and presence of various concentrations of cinnamyl alcohol (0 to 0.25 mM). B. Determination of the triplet energy transfer rate constant. Pseudo-first order rate constant of the decay of the thioxanthone triplet at various concentrations of cinnamyl alcohol.

FIG. 35. Sequencing confirmation of the substitutions to generate mutant variants of M.SssI. The substituted nucleotide is highlighted. WT shows sequence at the sites targeted for the substitution in the unmutated plasmid (without His insertion).

DETAILED DESCRIPTION OF THE INVENTION

Terms

Figure 1:
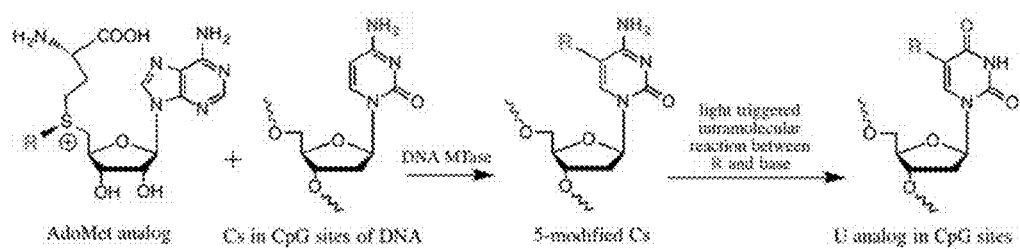
FIG. 1. Conversion of C to U by DNA methyltransferase (MTase) using AdoMet analoq. MTase transfers a chemical conversion group R from AdoMet analog to the 5 position of cytosine. After transfer, photochemically triggered intramolecular reaction between the R group and C facilitates deamination at the 4 position to form a U analog. DNA MTases are able to transfer a wide variety of functional groups to the 5 position of cytosines in double stranded DNA with high sequence specificity.

As used herein, and unless stated otherwise, each of the following terms shall have the definition set forth below.

| A | Adenine; |
|---|---|
| C | Cytosine; |
| DNA | Deoxyribonucleic acid; |
| G | Guanine; |
| RNA | Ribonucleic acid; |
| T | Thymine; and |
| U | Uracil. |

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Type" of nucleotide refers to A, G, C, T or U. "Type" of base refers to adenine, guanine, cytosine, uracil or thymine.

For simplicity in this application, C and dC are used interchangeably, as are A and dA, U and dU, G and dG, T and dT. Similarly, for simplicity, analogs bearing intermediate structures/properties between T and U are herein referred to as U.

"Mutant" DNA methyltransferases refer to modified DNA methyltransferases including but not limited to modified M.SssI, M.HhaI and M.CviJI.

"Mass tag" shall mean a molecular entity of a predetermined size which is capable of being attached by a cleavable bond to another entity.

"Solid substrate" shall mean any suitable medium present in the solid phase to which a nucleic acid or an agent may be affixed. Non-limiting examples include chips, beads and columns.

"Hybridize" shall mean the annealing of one single-stranded nucleic acid to another nucleic acid based on sequence complementarity. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.)

Embodiments of the Invention

The present invention provides a compound having the structure:

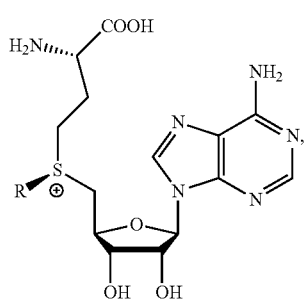

wherein R is

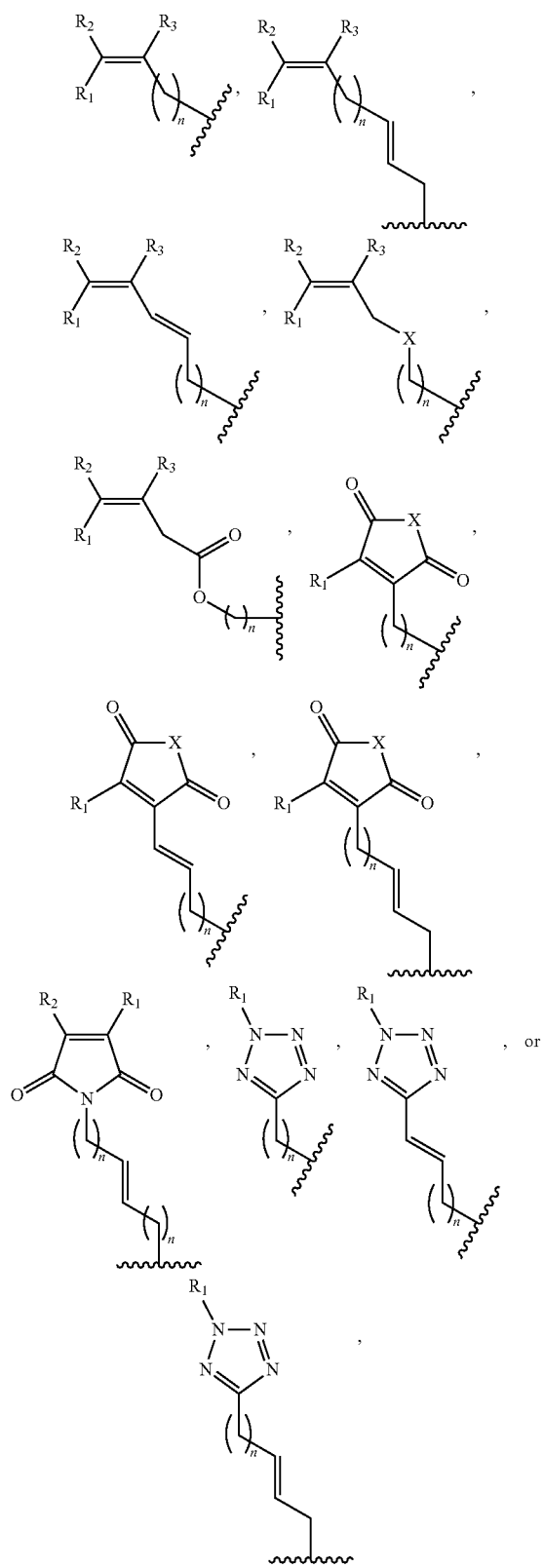

wherein $R_1$, $R_2$ and $R_3$ are independently H, alkyl, aryl, $C(O)NH_2$, $C(O)R'$, CN, $NO_2$, $C(O)R'$, $S(O)_2NHR'$;

wherein X is O or NR';
wherein R' is H, alkyl or aryl; and
wherein n is an integer from 1 to 8,
with the proviso that, when R is

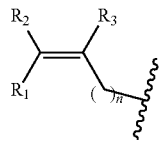

and n is 1, at least one of $R_1$, $R_2$ or $R_3$ is other than H.

In one or more embodiments, R is

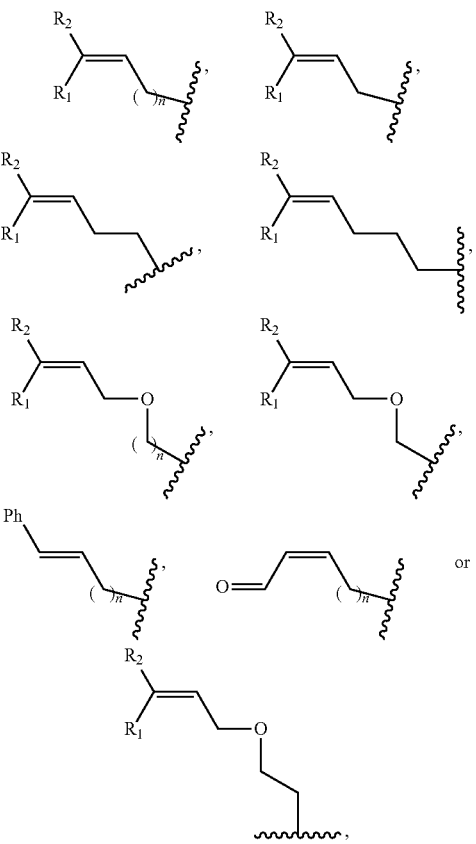

wherein $R_1$ and $R_2$ are independently H, alkyl, aryl, $C(O)NH_2$, $C(O)R'$, CN, $NO_2$, $C(O)R'$, $S(O)_2NHR'$;
wherein X is O or NR';
wherein R' is H, alkyl or aryl; and
wherein n is an integer from 1 to 8,
with the proviso that, when R is

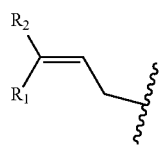

or when R is
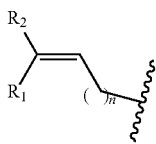
and n is 1, at least one of $R_1$ or $R_2$ is other than H.
In one or more embodiments, R is
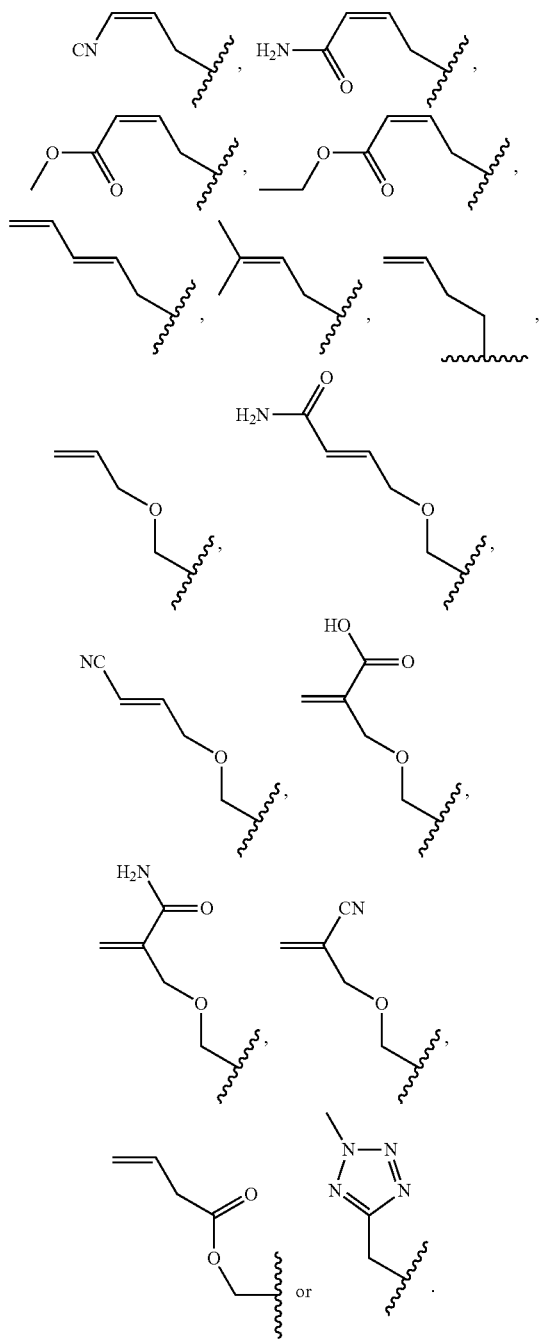
In one or more embodiments, R' is H or alkyl.
The present invention also provides a composition of matter comprising a compound having the structure:
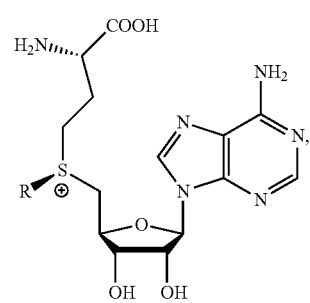
wherein R is
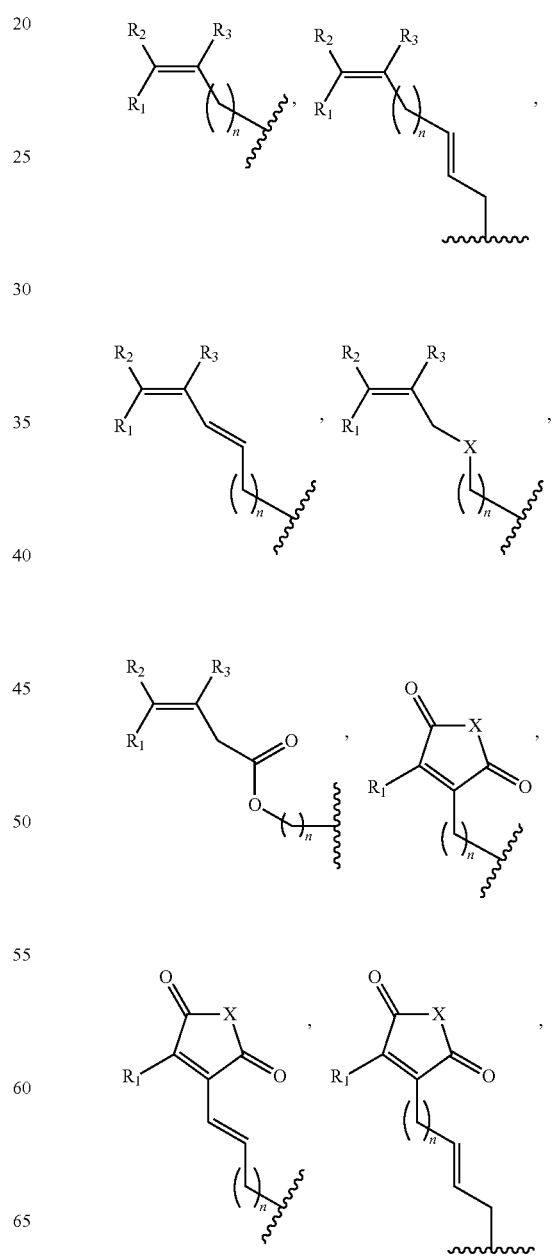

-continued

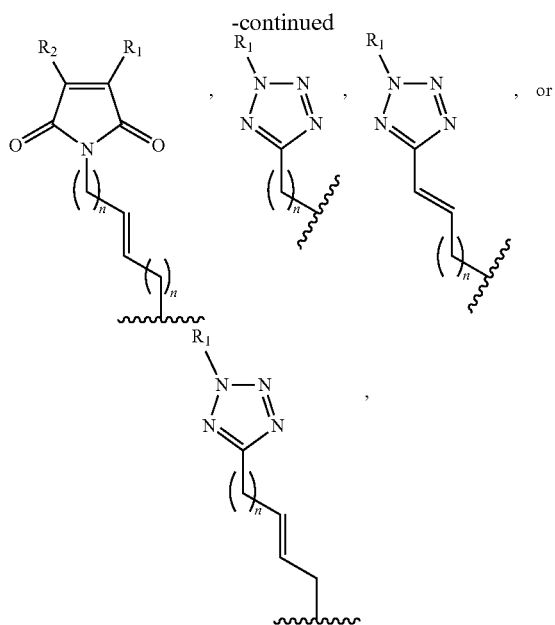

wherein $R_1$, $R_2$ and $R_3$ are independently H, alkyl, aryl, $C(O)NH_2$, $C(O)R'$, CN, $NO_2$, $C(O)R'$, $S(O)_2NHR'$;
wherein X is O or NR';
wherein R' is H, alkyl or aryl; and
wherein n is an integer from 1 to 8,
with the proviso that, when R is

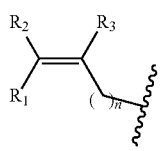

and n is 1, at least one of $R_1$, $R_2$ or $R_3$ is other than H, attached to a CpG methyltransferase.

In one or more embodiments, R is

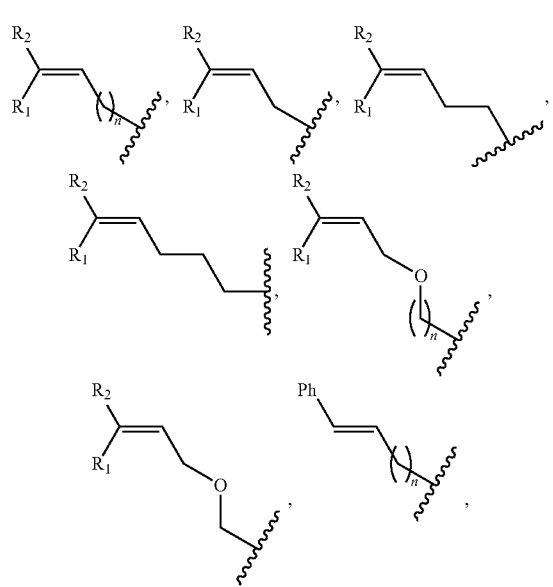

-continued

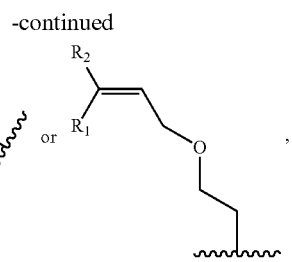

wherein $R_1$ and $R_2$ are independently H, alkyl, aryl, $C(O)NH_2$, $C(O)R'$, CN, $NO_2$, $C(O)R'$, $S(O)_2NHR'$;
wherein X is O or NR';
wherein R' is H, alkyl or aryl; and
wherein n is an integer from 1 to 8,
with the proviso that, when R is

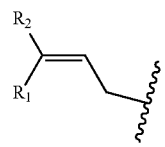

or when R is

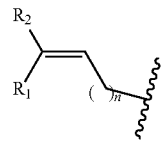

and n is 1, at least one of $R_1$ or $R_2$ is other than H.

In on or more embodiments, R is

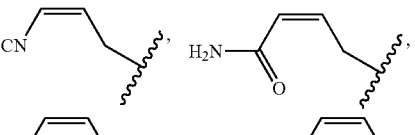

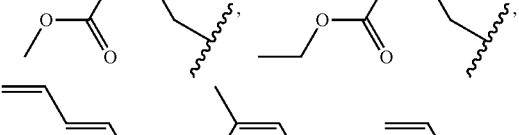

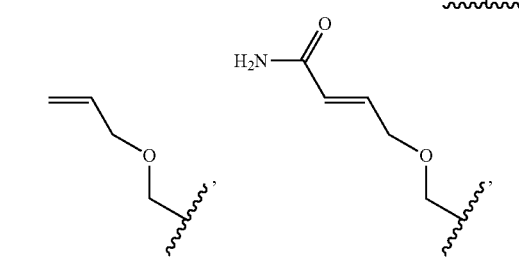

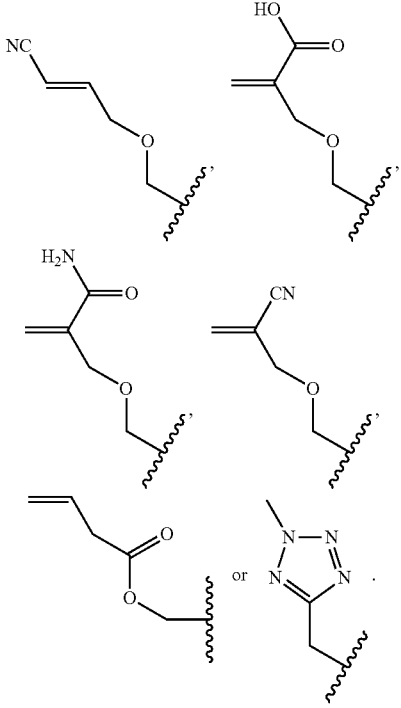

In one or more embodiments, R' is H or alkyl.

In one or more embodiments, the compound is attached to the active site of the CpG methyltransferase.

In one or more embodiments, the CpG methyltransferase is SssI methyltransferase or a mutant thereof.

In one or more embodiments, the CpG methyltransferase is HhaI methyltransferase or a mutant thereof.

In one or more embodiments, the CpG methyltransferase is CviJI methyltransferase or a mutant thereof.

The present invention also provides a process of producing a derivative of a double-stranded DNA comprising contacting the double-stranded DNA with a CpG methyltransferase and an S-adenosylmethionine analog having the structure:

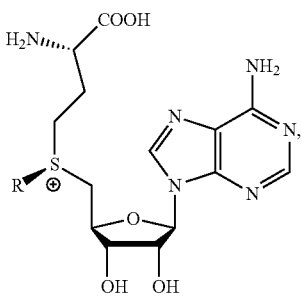

wherein R is a chemical group capable of being transferred from the S-adenosylmethionine analog by the CpG methyltransferase to a 5-carbon of a non-methylated cytosine of the double-stranded DNA, under conditions such that the chemical group covalently binds to the 5-carbon of the non-methylated cytosine of the double-stranded DNA, and thereby produces the derivative of the double-stranded DNA, wherein the chemical group has the structure:

wherein $R_1$, $R_2$ and $R_3$ are independently H, alkyl, aryl, $C(O)NH_2$, $C(O)R'$, CN, $NO_2$, $C(O)R'$, $S(O)_2NHR'$;
wherein X is O or NR';
wherein R' is H, alkyl or aryl; and
wherein n is an integer from 1 to 8, with the proviso that, when R is

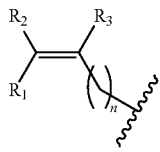

and n is 1, at least one of $R_1$, $R_2$ or $R_3$ is other than H.

In one or more embodiments, the chemical group has the structure

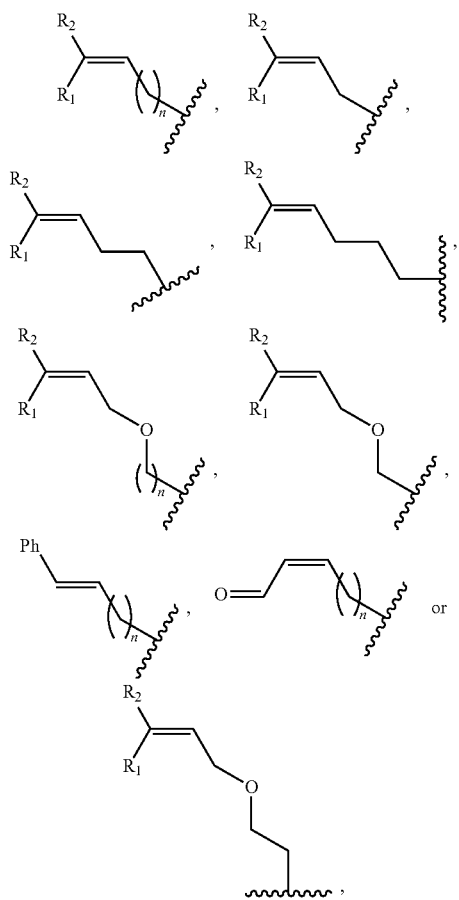

wherein $R_1$ and $R_2$ are independently H, alkyl, aryl, C(O)NH$_2$, C(O)R', CN, NO$_2$, C(O)R', S(O)$_2$NHR';
wherein X is O or NR';
wherein R' is H, alkyl or aryl; and
wherein n is an integer from 1 to 8,
with the proviso that, when R is

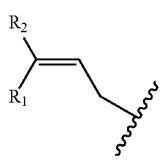

or when R is

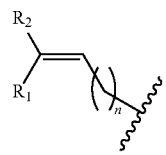

and n is 1, at least one of $R_1$ or $R_2$ is other than H. In one or more embodiments, the chemical group has the structure

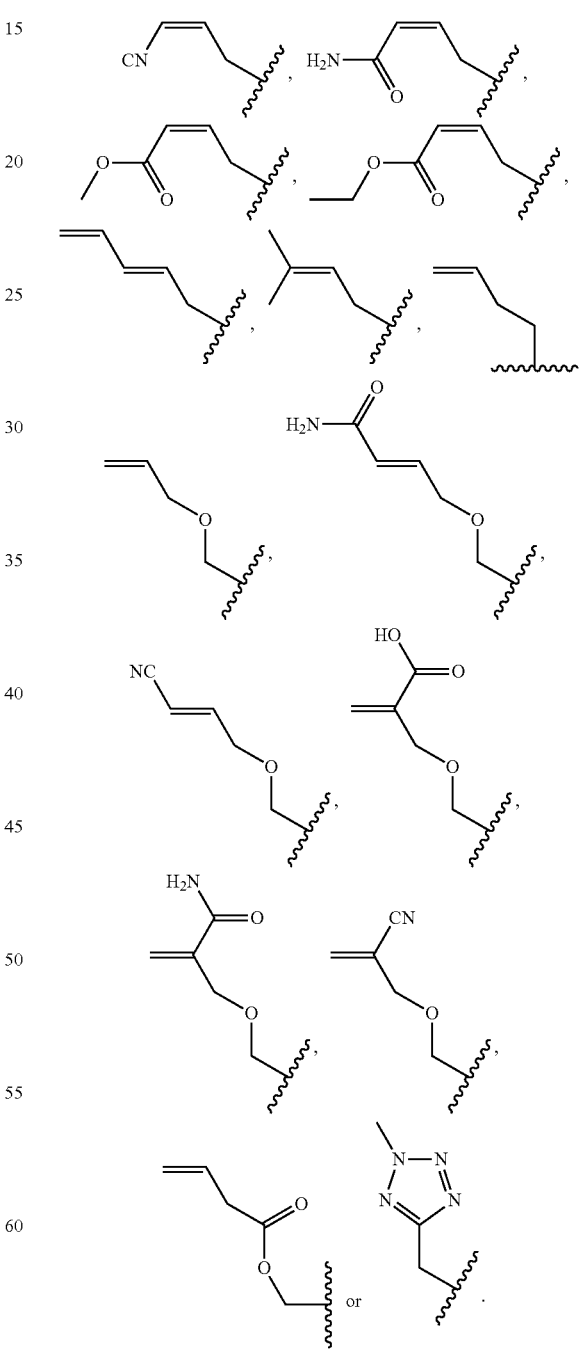

In one or more embodiments, R' is H or alkyl.

In one or more embodiments, the CpG methyltransferase is SssI methyltransferase or a mutant thereof.

In one or more embodiments, the CpG methyltransferase is HhaI methyltransferase or a mutant thereof.

In one or more embodiments, the CpG methyltransferase is CviJI methyltransferase or a mutant thereof.

In one or more embodiments, the chemical group capable of being transferred from the S-adenosylmethionine analog by the CpG methyltransferase to the 5-carbon of the non-methylated cytosine of the double-stranded DNA permits photochemical deamination of a 4-position of the non-methylated cytosine when it is covalently bound to the 5-carbon of the non-methylated cytosine of the double-stranded DNA.

In one or more embodiments, the non-methylated cytosine is immediately adjacent in sequence to a guanine in a single strand of the double-stranded DNA.

The present invention also provides a method of determining whether a cytosine present within a double-stranded DNA sequence of known sequence is non-methylated comprising:

a) producing a derivative of the double-stranded DNA by contacting the double-stranded DNA with a CpG methyltransferase and an S-adenosylmethionine analog having the structure:

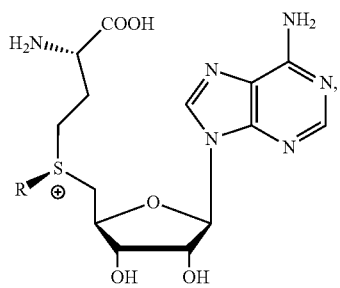

wherein R is a chemical group capable of being transferred from the S-adenosylmethionine analog by the CpG methyltransferase to a 5 carbon of a non-methylated cytosine of the double-stranded DNA so as to covalently bond the chemical group to the 5 carbon of the non-methylated cytosine of the double-stranded DNA, thereby making a derivatized double stranded DNA, wherein the chemical group has the structure:

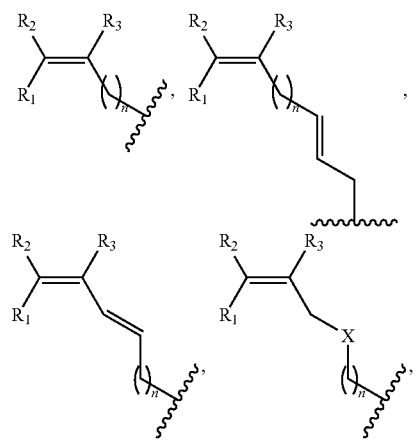

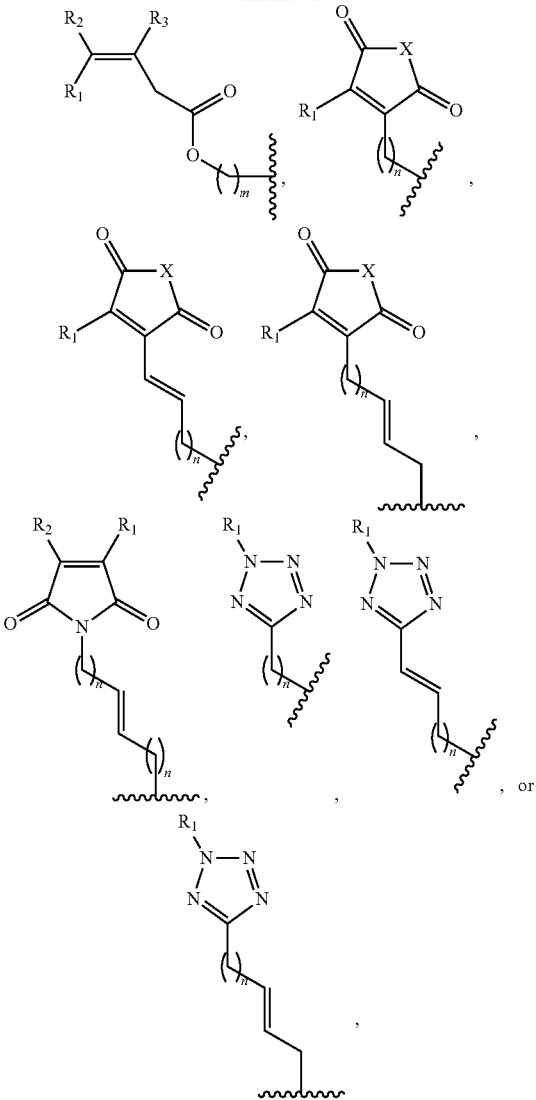

wherein $R_1$, $R_2$ and $R_3$ are independently H, alkyl, aryl, $C(O)NH_2$, $C(O)R'$, CN, $NO_2$, $C(O)R'$, $S(O)_2NHR'$;

wherein X is O or NR';

wherein R' is H, alkyl or aryl; and wherein n is an integer from 1 to 8;

b) producing a U analogue by photo-conversion of the derivative produced in step a);

c) separately obtaining a single strand of the derivative of the double-stranded DNA;

d) sequencing the single strand so obtained in step c); and e) comparing the sequence of the single strand determined in step d) to the sequence of a corresponding strand of the double-stranded DNA of which a derivative has not been produced, wherein the presence of a uracil analog in the single strand of the derivative single strand instead of a cytosine at a predefined position in the corresponding strand of the double-stranded DNA of which a derivative has not been produced indicates that the cytosine at that position in the double-stranded DNA is non-methylated.

In one or more embodiments, the chemical group has the structure

31

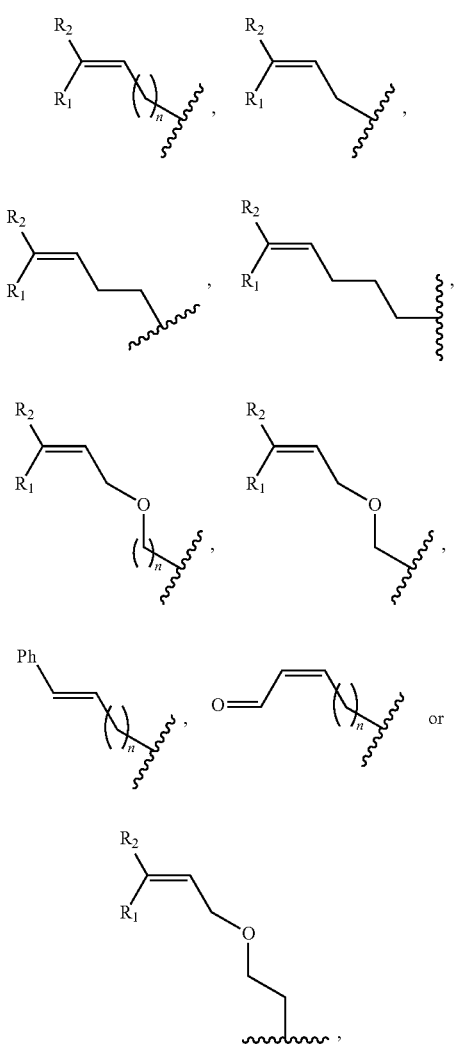

wherein $R_1$ and $R_2$ are independently H, alkyl, aryl, C(O)NH$_2$, C(O)R', CN, NO$_2$, C(O)R', S(O)$_2$NHR';

wherein X is O or NR';

wherein R' is H, alkyl or aryl; and wherein n is an integer from 1 to 8.

In one or more embodiments, the chemical group has the structure

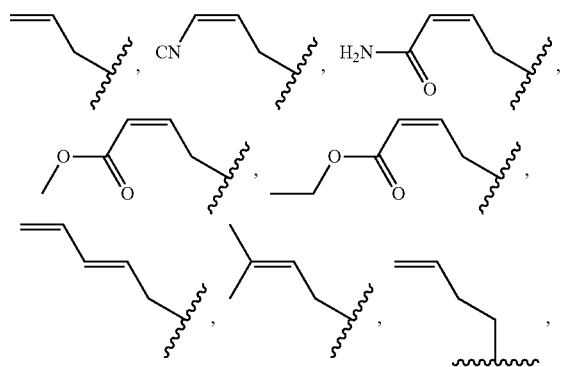

32

-continued

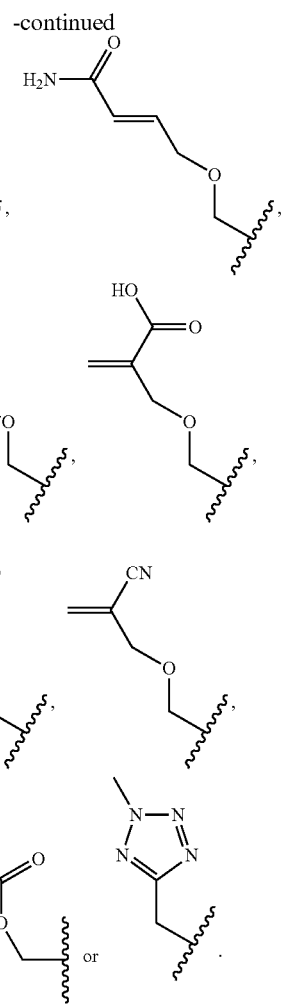

In one or more embodiments, R' is H or alkyl.

In one or more embodiments, the CpG methyltransferase is M.SssI methyltransferase or a mutant thereof.

In one or more embodiments, the CpG methyltransferase is M.HhaI methyltransferase or a mutant thereof.

In one or more embodiments, the CpG methyltransferase is M.CviJI methyltransferase or a mutant thereof.

In one or more embodiments, the non-methylated cytosine is immediately adjacent in sequence to a guanine in a single strand of the double-stranded DNA.

In one or more embodiments, the chemical group capable of being transferred from the S-adenosylmethionine analog by the CpG methyltransferase to the 5 carbon of the non-methylated cytosine of the double-stranded DNA permits photochemical deamination of a 4 position of the non-methylated cytosine when it is covalently bound to the 5 carbon of the non-methylated cytosine of the double-stranded DNA.

In one or more embodiments, in step d) the sequencing is sequencing by synthesis.

In one or more embodiments, the sequencing by synthesis comprises contacting the derivatized single strand with a DNA polymerase, a primer oligonucleotide, dATP, dCTP, dGTP, dTTP, and a dideoxynucleotide triphosphate having a detectable label attached thereto.

In one or more embodiments, the detectable label is radioactive or fluorescent.

In one or more embodiments, the detectable label is a mass tag.

In one or more embodiments, the detectable label is a molecule with electronic properties that affect an ionic current in a nanopore by, for example, reducing such current.

In one or more embodiments, the method further comprises attaching the single strand to a solid support prior to step d).

The present invention also provides a derivatized DNA molecule, wherein the derivatized DNA molecule differs from DNA by comprising a nucleotide residue which comprises a base having the following structure:

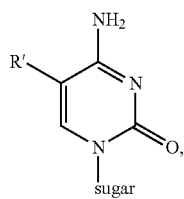

wherein R' is

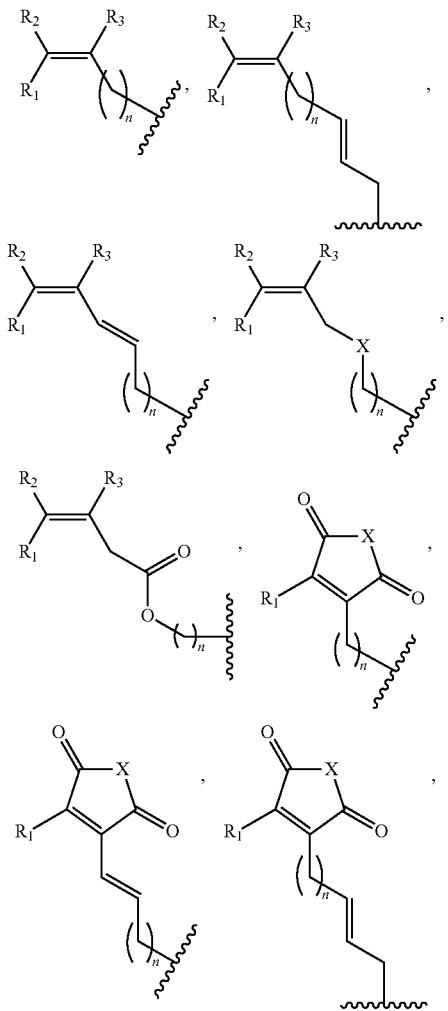

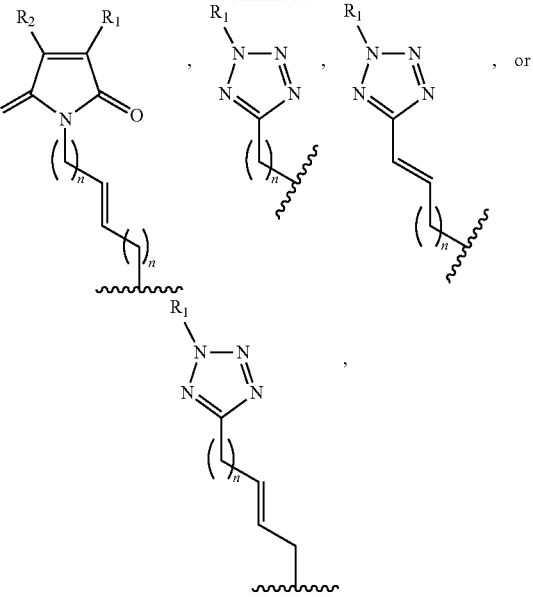

wherein $R_1$, $R_2$ and $R_3$ are independently H, alkyl, aryl, $C(O)NH_2$, $C(O)R''$, CN, $NO_2$, $C(O)R''$, $S(O)_2NHR''$;

wherein X is O or NR'';

wherein R'' is H, alkyl or aryl; and wherein n is an integer from 1 to 8, with the proviso that, when R' is

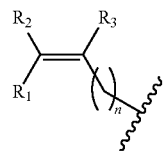

and n is 1, at least one of $R_1$, $R_2$ or $R_3$ is other than H, and wherein the sugar is a sugar of the nucleotide residue.

In one or more embodiments, R' is

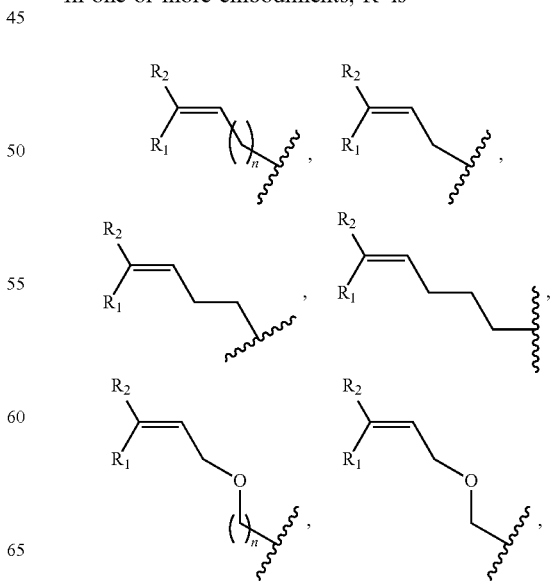

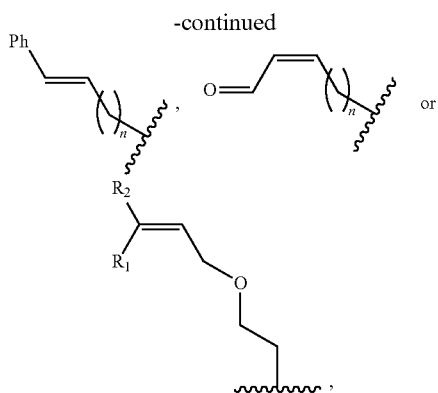

wherein $R_1$ and $R_2$ are independently H, alkyl, aryl, C(O)NH$_2$, C(O)R", CN, NO$_2$, C(O)R", S(O)$_2$NHR";
wherein X is O or NR";
wherein R" is H, alkyl or aryl; and
wherein n is an integer from 1 to 8,
with the proviso that, when R' is

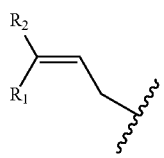

or when R' is

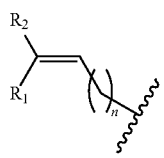

and n is 1, at least one of $R_1$ or $R_2$ is other than H. In one or more embodiments, R' is

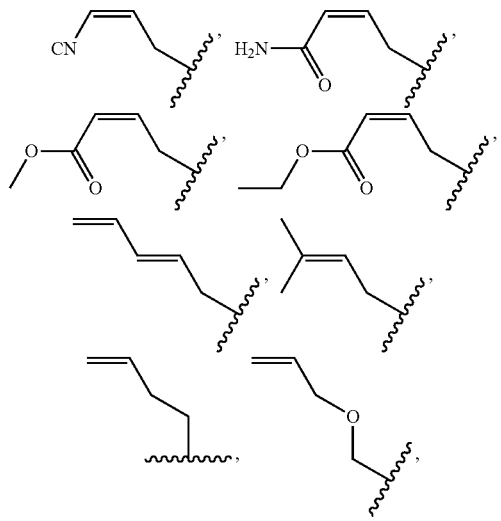

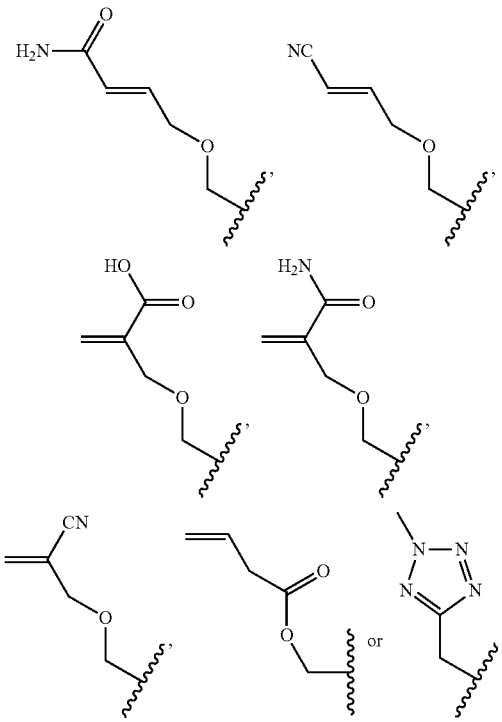

In one or more embodiments, R" is H or alkyl.

The present invention also provides a derivatized DNA molecule, wherein the derivatized DNA molecule differs from DNA by comprising a nucleotide residue which comprises a base having the following structure:

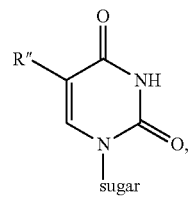

wherein R" is

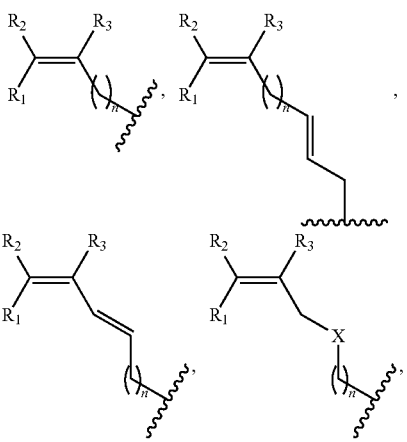

-continued

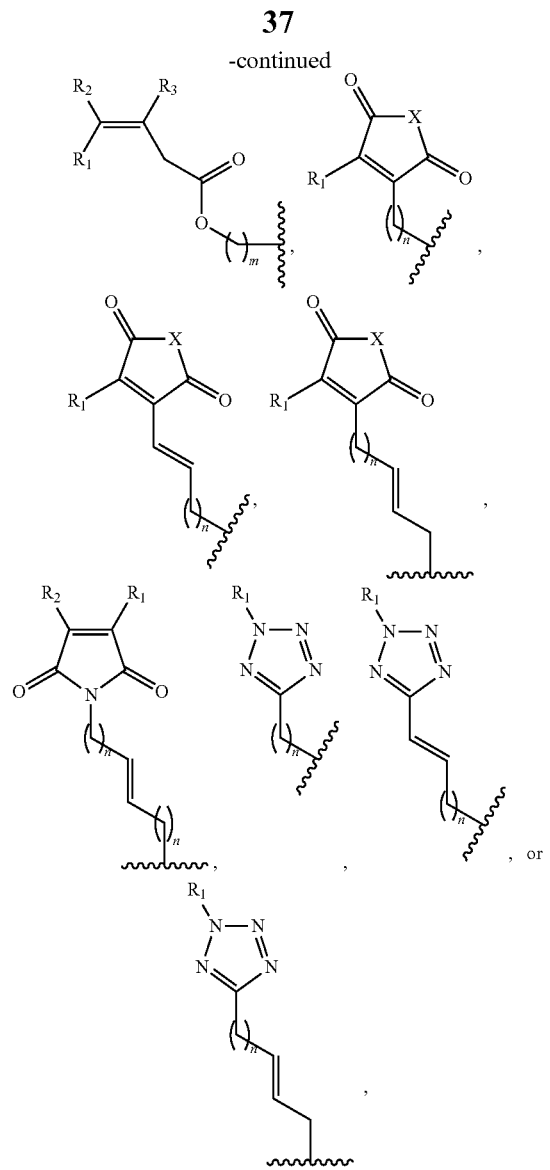

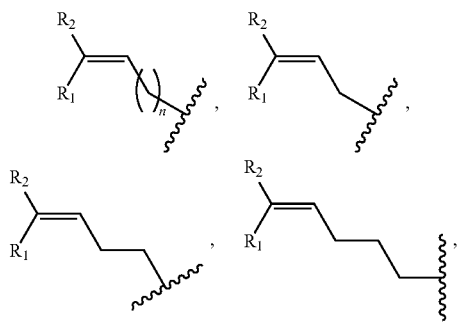

wherein $R_1$, $R_2$ and $R_3$ are independently H, alkyl, aryl, C(O)NH$_2$, C(O)R', CN, NO$_2$, C(O)R', S(O)$_2$NHR';
wherein X is O or NR';
wherein R' is H, alkyl or aryl; and
wherein n is an integer from 1 to 8,
and wherein the sugar is a sugar of the nucleotide residue.

In one or more embodiments, R" is structure

-continued

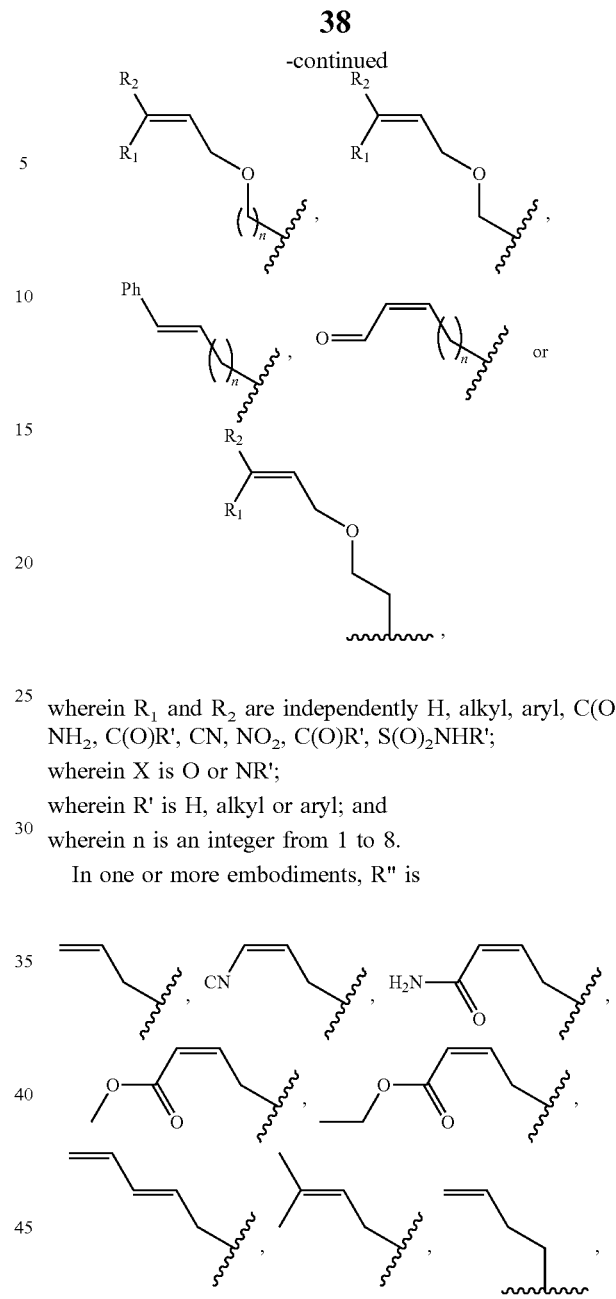

wherein $R_1$ and $R_2$ are independently H, alkyl, aryl, C(O)NH$_2$, C(O)R', CN, NO$_2$, C(O)R', S(O)$_2$NHR';
wherein X is O or NR';
wherein R' is H, alkyl or aryl; and
wherein n is an integer from 1 to 8.

In one or more embodiments, R" is

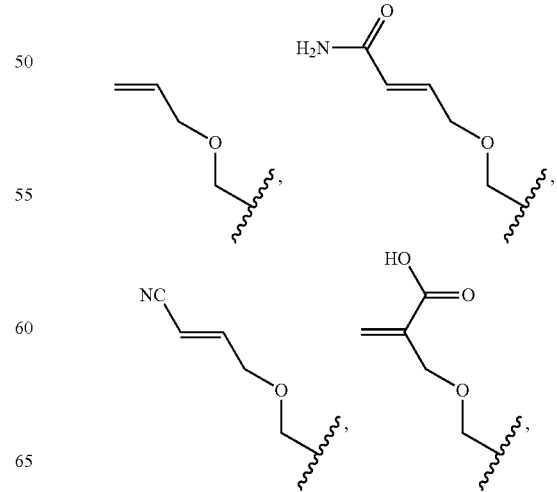

-continued

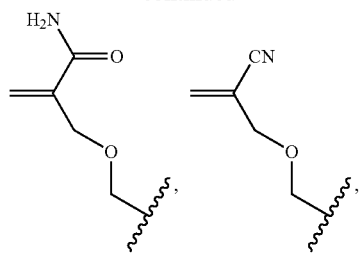

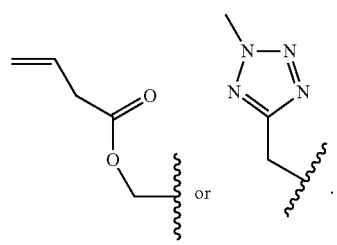

or

In one or more embodiments, R' is H or alkyl.

The present invention also provides a kit for derivatizing a double-stranded DNA molecule or for determining whether a cytosine present within a double-stranded DNA sequence of known sequence is non-methylated comprising:

a) a compound having the structure:

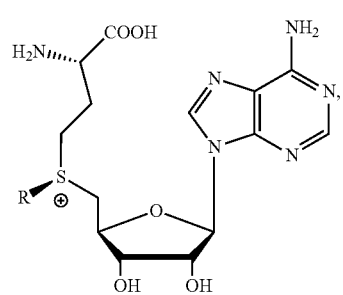

wherein R is

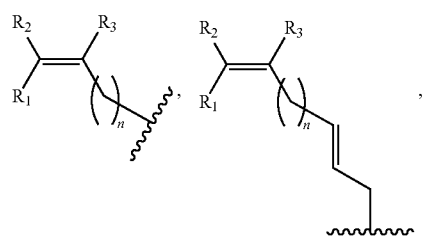

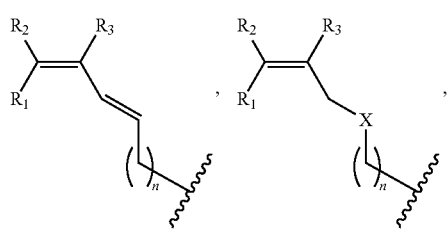

-continued

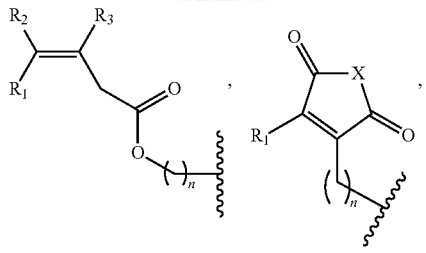

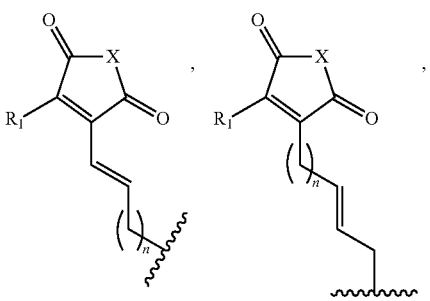

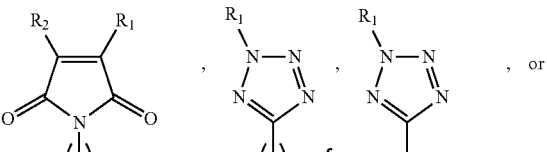

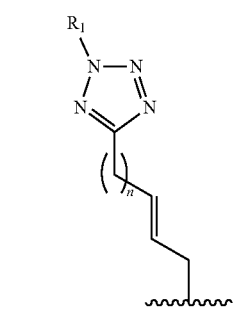

wherein $R_1$, $R_2$ and $R_3$ are independently H, alkyl, aryl, C(O)NH$_2$, C(O)R', CN, NO$_2$, C(O)R', S(O)$_2$NHR';

wherein X is O or NR';

wherein R' is H, alkyl or aryl; and wherein n is an integer from 1 to 8; and b) instructions for use.

In one or more embodiments, R is

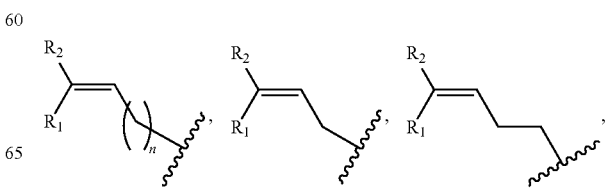

-continued

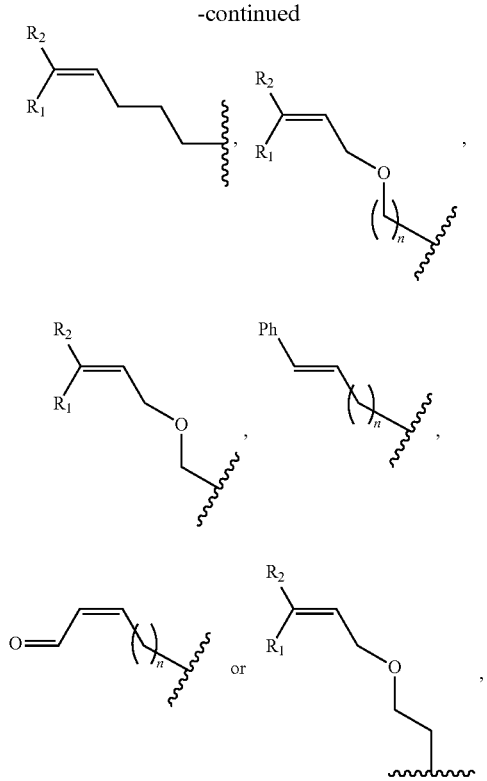

wherein $R_1$ and $R_2$ are independently H, alkyl, aryl, C(O)NH$_2$, C(O)R', CN, NO$_2$, C(O)R', S(O)$_2$NHR';
wherein X is O or NR';
wherein R' is H, alkyl or aryl; and
wherein n is an integer from 1 to 8.

In one or more embodiments, R is

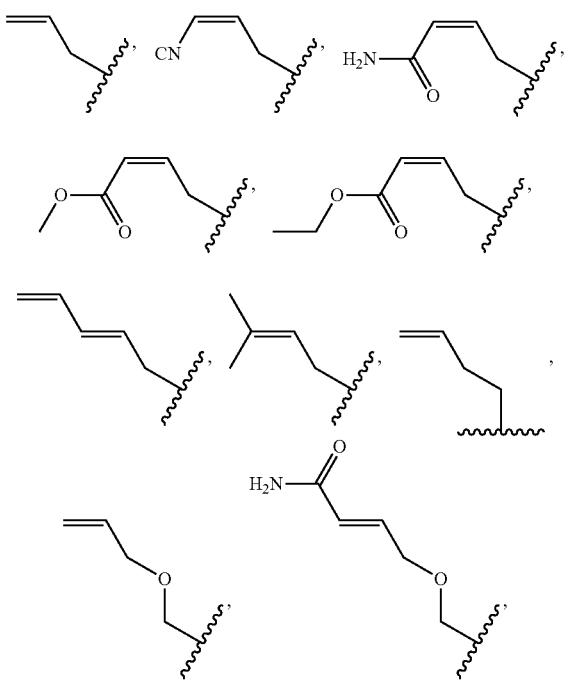

-continued

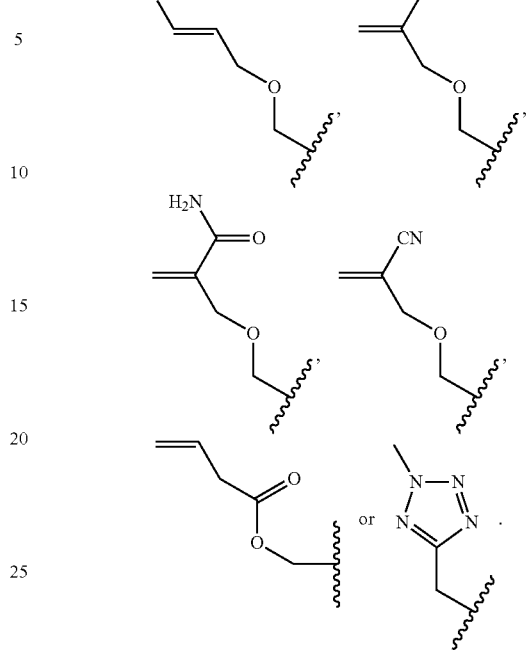

In one or more embodiments, R' is H or alkyl.

In one or more embodiments, the kit further comprises a CpG methyltransferase.

In one or more embodiments, the CpG methyltransferase is M.SssI methyltransferase or a mutant thereof.

In one or more embodiments, the CpG methyltransferase is M.HhaI methyltransferase or a mutant thereof.

In one or more embodiments, the CpG methyltransferase is M.CviJI methyltransferase or a mutant thereof.

The present invention also provides a method of determining whether a cytosine present within a double-stranded DNA sequence of known sequence is non-methylated comprising:

a) producing a derivative of the double-stranded DNA by contacting the double-stranded DNA with a CpG methyltransferase and an S-adenosylmethionine analog having the structure:

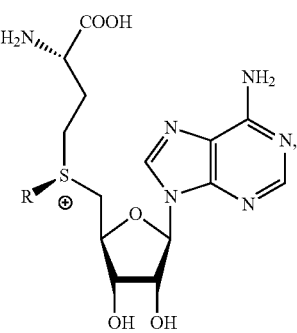

wherein R is a chemical group capable of being transferred from the S-adenosylmethionine analog by the CpG methyltransferase to a 5 carbon of a non-methylated cytosine of the double-stranded DNA so as to covalently bond the chemical group to the 5 carbon of the non-methylated cytosine of the double-stranded DNA, thereby making a derivatized double stranded DNA, wherein the chemical group has the structure:

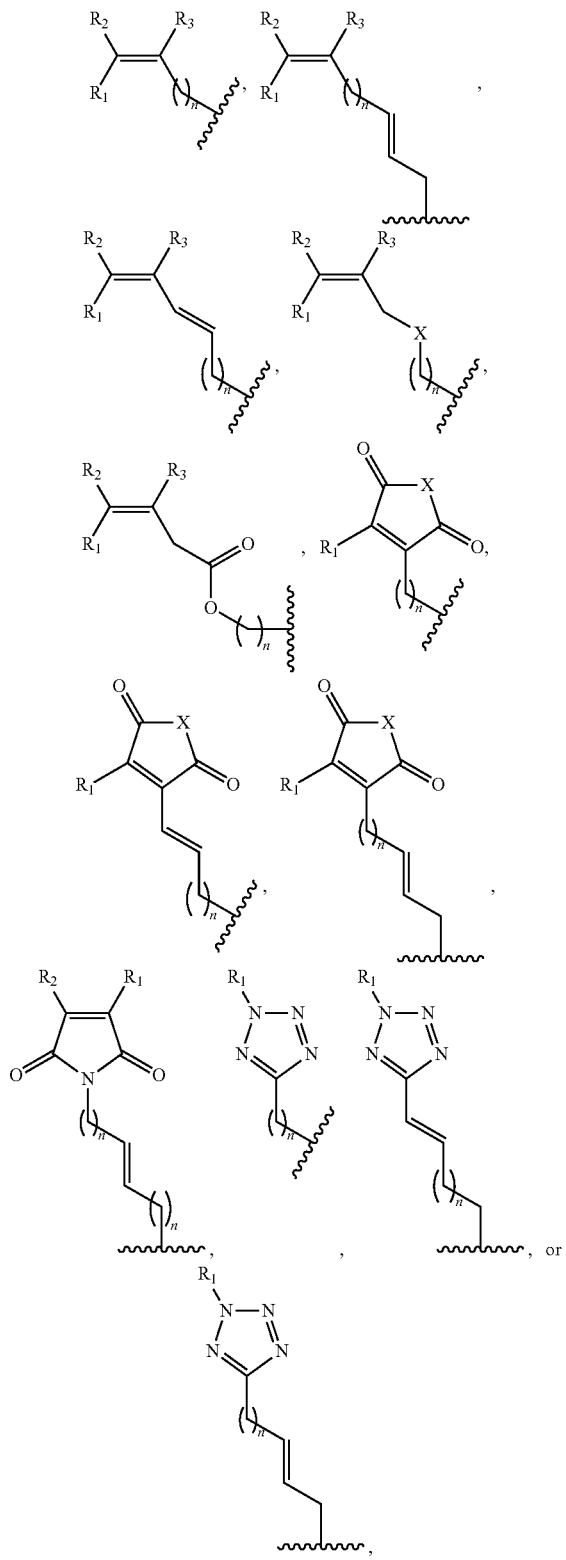

wherein $R_1$, $R_2$ and $R_3$ are independently H, alkyl, aryl, $C(O)NH_2$, $C(O)R'$, CN, $NO_2$, $C(O)R'$, $S(O)_2NHR'$;

wherein X is O or NR';

wherein R' is H, alkyl or aryl; and wherein n is an integer from 1 to 8; and b) determining whether a cytosine at a predefined position in the double-stranded DNA has been modified with the chemical group R, wherein modification with the chemical group R on the cytosine at a predefined position in the double-stranded DNA indicates that the cytosine at that position in the double-stranded DNA is non-methylated.

In an embodiment, the method further comprises a step of photo-conversion of a C analog to a U analog prior to step b).

In one or more embodiments the chemical group has the structure

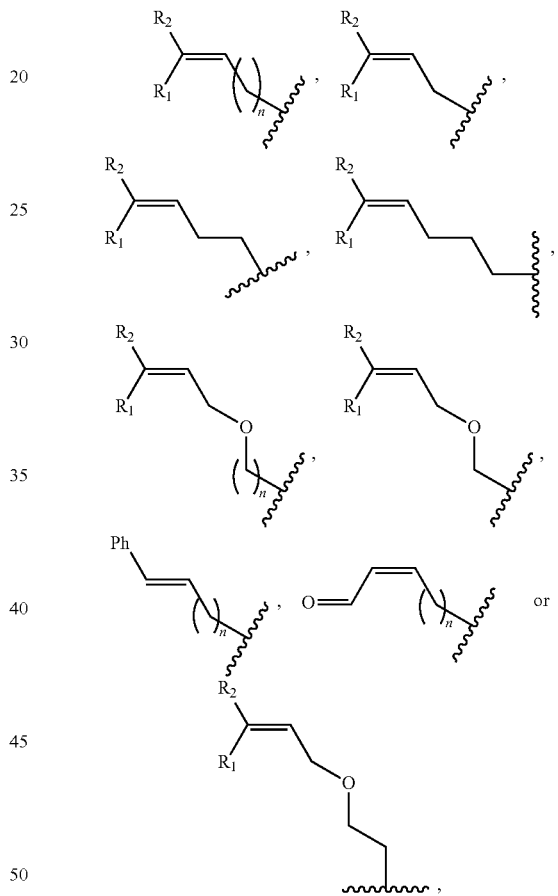

wherein $R_1$ and $R_2$ are independently H, alkyl, aryl, $C(O)NH_2$, $C(O)R'$, CN, $NO_2$, $C(O)R'$, $S(O)_2NHR'$;

wherein X is O or NR';

wherein R' is H, alkyl or aryl; and wherein n is an integer from 1 to 8.

In one or more embodiments the chemical group has the structure

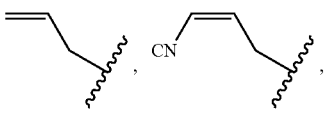

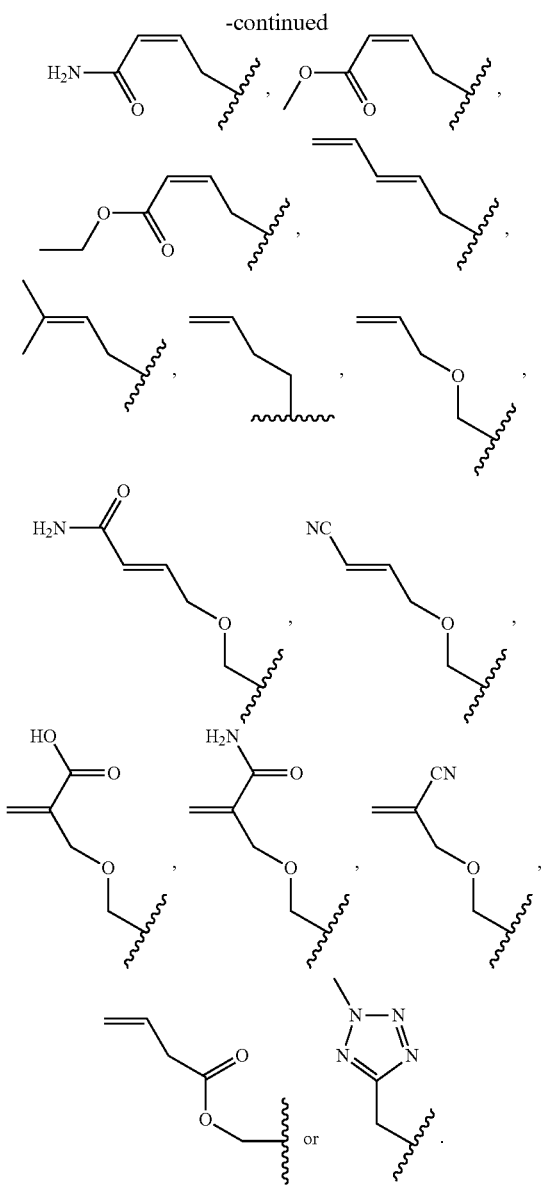

In one or more embodiments the CpG methyltransferase is SssI methyltransferase or a mutant thereof.

In one or more embodiments the CpG methyltransferase is HhaI methyltransferase or a mutant thereof.

In one or more embodiments the CpG methyltransferase is CviJI methyltransferase or a mutant thereof.

In one or more embodiments the CpG methyltransferase is M.SssI methyltransferase or a mutant thereof.

In one or more embodiments the CpG methyltransferase is M.HhaI methyltransferase or a mutant thereof.

In one or more embodiments the CpG methyltransferase is M.CviJI methyltransferase or a mutant thereof.

In one or more embodiments determining whether a cytosine at a predefined position in the double-stranded DNA has been modified with the chemical group R comprises converting the modified cytosine to a uracil analog.

In one or more embodiments, the method further comprises conversion of a modified cysteine residue in the DNA derivative to a uracil analog by a photo-catalyzed reaction.

In one or more embodiments the photo-catalyzed reaction is carried out using a Tris (bipyridine) ruthenium (II) chloride $(Ru(bpy)_3^{2+})$ catalyst.

In one or more embodiments the $(Ru(bpy)_3^{2+})$ catalyst is $Ru(bpy)_3Cl_2$.

In one or more embodiments the $(Ru(bpy)_3^{2+})$ catalyst is $Ru(bpy)_3(PF_6)_2$.

In one or more embodiments the light source for the photo-catalyzed reaction is a household bulb.

In one or more embodiments the light source for the photo-catalyzed reaction is a laser.

In one or more embodiments the laser has a wavelength of 400 nm-600 nm.

In one or more embodiments the photo-catalyzed reaction is carried out using photoirradiation at a wavelength of greater than 350 nm.

In one or more embodiments the photo-catalyzed reaction is carried out using a catalyst having long wavelength absorption properties.

In one or more embodiments the photo-catalyzed reaction is carried out using photoirradiation at a wavelength of 300 nm-700 nm.

In one or more embodiments the photo-catalyzed reaction is further carried out at a temperature between 0° C. and 90° C.

In one or more embodiments, the photo-catalyzed reaction is further carried out in a buffered solution with pH between 4 and 10.

This invention provides methods for methylation profiling. Methods for methylation profiling are disclosed in U.S. Patent Application Publication No. US 2011-0177508 A1, which is hereby incorporated by reference.

This invention provides the use of DNA methyltransferases. Examples of DNA methyltransferases include but are not limited to M.SssI, M.HhaI and M.CviJI as well as modified M.SssI, M.HhaI and M.CviJI. These enzymes are modified mainly to have reduced specificity such that R groups on AdoMet analogs can be more efficiently transferred to unmethylated C residues, including in the context of a CpG site in DNA. Examples of such modified M.SssI and M.HhaI genes have been described in the literature (Lukinavicius et al (2012) Engineering the DNA cytosine-5 methyltransferase reaction for sequence-specific labeling of DNA. Nucleic Acids Res 40:11594-11602; Kriukene et al (2013) DNA unmethylome profiling by covalent capture of CpG sites. Nature Commun 4:doi:10.1038/ncomms3190).

This invention provides the instant methods and processes, wherein the detectable label bound to the base via a cleavable linker is a dye, a fluorophore, a chromophore, a combinatorial fluorescence energy transfer tag, a mass tag, an electrophore, or a molecule that is capable of reducing an ion current in a nanopore. Combinatorial fluorescence energy tags and methods for production thereof are disclosed in U.S. Pat. No. 6,627,748, which is hereby incorporated by reference.

Detectable tags and methods of affixing nucleic acids to surfaces which can be used in embodiments of the methods described herein are disclosed in U.S. Pat. Nos. 6,664,079 and 7,074,597 which are hereby incorporated by reference.

This invention also provides the instant methods and processes, wherein the DNA is bound to a solid substrate. This invention also provides the instant method, wherein the DNA is bound to the solid substrate via 1,3-dipolar azide-alkyne cycloaddition chemistry. This invention also provides the instant methods and processes, wherein the DNA is bound to the solid substrate via a polyethylene glycol molecule. This invention also provides the instant methods and processes, wherein the DNA is alkyne-labeled. This invention also provides the instant method and processes, wherein the DNA is bound to the solid substrate via a polyethylene glycol molecule and the solid substrate is azide-functionalized. This invention also provides the instant methods and processes, wherein the DNA is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. This invention also provides the instant methods and processes, wherein the DNA is bound to the solid substrate via a polyethylene glycol molecule and the solid substrate is azide-functionalized or the DNA is immobilized on the solid substrate via an azido linkage, an alkynyl linkage, or biotin-streptavidin interaction. In an embodiment, the DNA or nucleic acid is attached/bound to the solid surface by covalent site-specific coupling chemistry compatible with DNA.

This invention also provides the instant methods and processes, wherein the solid substrate is in the form of a chip, a bead, a well, a capillary tube, a slide, a wafer, a filter, a fiber, a porous medium, or a column. This invention also provides the instant methods and processes, wherein the solid substrate is gold, quartz, silica, plastic, glass, nylon, diamond, silver, metal, polypropylene, or graphene. This invention also provides the instant method, wherein the solid substrate is porous. Chips or beads may be made from materials common for DNA microarrays, for example glass or nylon. Beads/micro-beads may be in turn immobilized to chips.

This invention also provides the instant methods and processes, wherein about 1000 or fewer copies of the DNA are bound to the solid substrate. This invention also provides the instant methods and processes wherein $2 \times 10^7$, $1 \times 10^7$, $1 \times 10^6$ or $1 \times 10^4$ or fewer copies of the DNA are bound to the solid substrate.

This invention also provides the instant methods and processes, wherein the nucleotide analogues comprise one of the fluorophores Cy5, Bodipy-FL-510, ROX and R6G.

This invention also provides the instant methods and processes, wherein the DNA polymerase is a 9°N polymerase or a variant thereof.

DNA polymerases which can be used in the instant invention include, for example E. coli DNA polymerase I, Bacteriophage T4 DNA polymerase, Sequenase™, Taq DNA polymerase, 9° N polymerase (exo-) A485L/Y409V, Phi29 or Bst2.0. RNA polymerases which can be used in the instant invention include, for example, Bacteriophage SP6, T7 and T3 RNA polymerases.

Methods for production of cleavably capped and/or cleavably linked nucleotide analogues are disclosed in U.S. Pat. No. 6,664,079, which is hereby incorporated by reference.

DNA Methylation is described in U.S. Patent Application Publication No. 2003-0232371 A1 which is hereby incorporated by reference in its entirety.

All combinations and subcombinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

DNA methylation at specific sequences was first analyzed by Southern blotting after cleavage with methylation-sensitive restriction endonucleases (MSREs) such as HpaII, which fails to cleave the sequence 5'-CCGG-3' when the central CpG dinucleotide is methylated (Waalwijk and Flavell, 1978). This method is robust and provides an internal control for complete digestion when the blot is reprobed for mitochondrial DNA, which is not methylated and is present in many copies. However, the MSRE method is tedious, expensive, requires relatively large amounts of radioactive nucleotides, and can test only a small number of CpG sites per fragment because only ~20% of all CpG sites fall within the recognition sequence of a known MSRE. If a given fragment contains many CpG sites and only one or a few are unmethylated, the sequence is often scored as unmethylated. MSRE provides the best-controlled method of methylation analysis, but low throughput and other shortcomings means that it cannot form the basis for a whole-genome methylation profiling platform.

Numerous other PCR-based methods for rapid methylation profiling of single or small numbers of CpG sites have been developed; examples are methylation-sensitive PCR (MSP; Steigerwald et al., 1990), COBRA (Eads and Laird, 2002) and methyl-light (Trinh et al., 2001). These methods are fast and inexpensive but can test only small numbers of CpG sites; they are unsuitable for unbiased whole-genome methylation profiling. After specific methylation abnormalities have been found to be associated with a given disorder, these focused methods might be found to be appropriate for diagnostic and prognostic tests in clinical samples.

Microarray analysis has been applied, with considerable success (for example, Gitan et al., 2002). However, microarray methods cannot address the methylation status of repeated sequences (which contain the majority of 5-methylcytosine in the genome; Rollins et al., 2006), and CpG islands give rise to high noise levels as a result of their high G+C contents. Microarrays cannot examine the methylation status of each CpG dinucleotide. Again, while this method has its advantages, it is not suited to whole-genome methylation profiling.

An important advance in methylation profiling came with the introduction of bisulfite genomic sequencing (BGS) by Susan Clark and Marianne Frommer in 1994 (Clark et al., 1994). BGS depends on the ability of sodium bisulfite to oxidatively deaminate the 4 position of cytosine, thereby converting the base to uracil. A methyl group at the 5 position prevents bisulfite from adding across the 5-6 double bond, which renders 5-methyl cytosine resistant to bisulfite conversion. PCR amplification followed by DNA sequencing produces a C lane in which each band corresponds to what was a 5-methylcytosine in the starting DNA; all unmethylated cytosines are sequenced as thymines. BGS was an important advance over earlier methods of genomic sequencing (Church and Gilbert, 1984).

However, BGS has severe drawbacks when applied to whole genome methylation profiling. First, it cannot be known if the thymines in the final sequence were thymines or cytosines in the starting material unless one sequences both in the presence and in the absence of bisulfite treatment and compares the results. This severely reduces the information content of DNA. As a result, the new ultrahigh throughput DNA sequencing methods cannot be used, as sequence reads are short and a large percentage of the sequences cannot be mapped to a single position in the genome. Very few repetitive sequences can be mapped at all. BGS is largely restricted to pre-selected regions of the genome where primers can be designed to selectively amplify the region of interest. Whole-genome methylation profiles cannot be obtained by this method, as many regions of the genome do not allow design of unique primer sets.

CpG islands are especially problematic, as primer sites free of CpG dinucleotides cannot be found in most CpG islands. Second, bisulfite conversion requires that the DNA be single stranded; any double stranded DNA will be resistant to conversion and will be scored as methylated. As a result, bisulfite treatment must be performed under very harsh conditions (0.2 N sodium hydroxide at elevated temperature for several hours). Under these conditions bisulfite conversion and chain breakage are competing reactions, and bisulfite conversion only approaches completion when >95% of the DNA has been cleaved to less than 350 bp (Warnecke et al., 2002). This means that large amounts of starting DNA must be used and the DNA must be long. This prevents the use of DNA from paraffin sections, where the DNA is almost all <300 bp, and also prevents the use of small amounts of DNA, as in the case of early embryos, small tissue biopsies, and other cases in which large amounts of DNA are not available. Third, CpG dinucleotides in certain sequence contexts are inherently resistant to bisulfite conversion (Warnecke et al., 2002), and are scored as spurious sites of methylation. Fourth, the loss of all C-G base pairs introduces a large bias in the PCR amplification step in favor of PCR product derived from unconverted or methylated starting material. (Warnecke et al., 1997). Each of these artifacts can be severe.

Together the loss of sequence information upon bisulfite conversion, the strong PCR biases, the artifacts of bisulfite conversion, and the need for large amounts of long starting DNA renders conventional BGS inappropriate for whole-genome methylation profiling by ultrahigh throughput DNA sequencing.

Over the past few years this laboratory has developed new methods to fractionate the normal human genome into methylated and unmethylated compartments and have determined the methylation status of CpG dinucleotides in excess of 30 million base pairs from the fractionated genomes in order to characterize the methylation landscape of the normal human genome (Rollins et al., 2006). In that work, new computational methods were developed that mapped annotated features of the genome onto very large assemblages of sequence data. Although this method, which depends on the enzymatic fractionation of DNA into methylated and unmethylated compartments, has provided information on the methylation status of more CpG sites than the sum total of all other methods, it remains incapable of whole-genome methylation profiling because of shortcomings that cannot be overcome with existing technology.

Examples of methylation abnormalities are identified by the method of Rollins et al. (2006). It should be noted that the method disclosed herein can be applied to any sequenced genome; mammary carcinoma was characterized because highly abnormal methylation patterns are known to be present in the genomes of these cells and these genomes provide an excellent test system.

Previous studies from the Klimasauskas and Weinhold groups (Dalhoff et al., 2006a, 2006b) have shown that a wide variety of functional groups can be efficiently transferred by DNA methyltransferases to the 5 position of cytosines in DNA by means of synthetic AdoMet analogs in which the methyl group has been replaced by any of a wide variety of functional groups. Specifically, Dalhoff et al. (2006a) synthesized synthetic variants of AdoMet with a range of functional groups replacing the methyl group, which also enabled the efficient functioning of DNA MTases. Dalhoff et al (2006b) then demonstrated the transfer of a variety of functional groups to the 5 position of Cs in DNA sites of cytosine and guanine repeats (CpG sites) with essentially 100% efficiency using DNA methyltransferases.

Haga et al. (1993) demonstrated the photo-conversion (conversion under influence of light) of cytosine in the presence of 2.3-dimethyl-2-butene in acetone to the corresponding cyclobutane photo-adducts (product formed by the light induced addition of two or more reactants). This chemistry was applied by Matsumura et al., (2008) and Fujimoto et al. (2010) for the on-DNA conversion of C to U. Applicant's research seeks to apply the knowledge derived from these research studies on AdoMet, enzymatic transfer using Mtase and photo-conversion of C to U, to devise a novel method for single cell, whole genome methylome analysis.

Bulky groups such as biotin can be added to every recognition site for a given methyltransferase. Here DNA methyltransferase M.SssI can be used to transfer specific reactive groups to the 5 position of cytosines in every unmethylated CpG dinucleotide; non-CpG cytosines are not modified. If the cytosine is methylated, this reaction is blocked—only unmethylated CpG dinucleotides are derivatized. The most important aspect of the transferred group is that it alters base pairing during sequencing or during amplification by PCR so as to allow discrimination of CpG dinucleotides that were methylated or unmethylated in the starting DNA. The method is conceptually related to bisulfite genomic sequencing, but does not suffer from the deficiencies that render BGS unusable in whole-genome methylation profiling.

Example 1: Methods for Genome-Wide DNA Methylation Profiling Based on DNA Methyltransferase Aided Site-Specific Conversion of Cytosine in CpG Islands A superior method of methylation profiling based on a unique and innovative approach is developed. The Klimasauskas and Weinhold groups (Dalhoff et al., 2006a, 2006b) synthesized S-adenosyl-L-methionine (AdoMet) analogs in which the methyl group has been replaced by a variety of functional groups, and show that DNA methyltransferases are able to specifically transfer these functional groups to the 5 position of cytosines in DNA CpG sites. Efficiency is essentially 100% (Dalhoff et al., 2006a, 2006b). Thus DNA methyltransferases have been used for sequence-specific, covalent attachment of larger chemical groups to DNA, providing new molecular tools for precise, targeted functionalization and labeling of large natural DNAs.

We take advantage of this capacity to use CpG site-specific DNA methyltransferases to modify the 5 position of C with suitable reactive intermediates that can subsequently convert C to a uridine (U) analog. Such a conversion strategy meets the above mentioned criteria and overcomes the drawbacks in existing methods, therefore advancing the field of genome-wide DNA methylation profiling.

A novel genome-wide methylation profiling approach based on DNA methyltransferase aided site-specific conversion of C in unmethylated CpG dinucleotides is developed. In this approach, AdoMet analogs derivatized with C-reactive functionalities are used as substrates of DNA methyltransferases to transfer the reactive functionalities to the 5 position of C in unmethylated CpG dinucleotides (FIG. 1). For example, CpG site-specific bacterial DNA methyltransferase M.SssI, which methylates all CpG dinucleotides using AdoMet as a donor, may be used in order to drive chemical conversion of C's to U's in unmethylated CpG dinucleotides; this is enabled by the enzyme's strict CpG site recognition and high selectivity for bond formation at the 5 position of C (Renbaum et al., 1990). Analogs of AdoMet are developed that enable the M.SssI directed transfer of groups to unmethylated C's of DNA, to facilitate the efficient photo-conversion of these modified CpG C's to U's with minimal damage to DNA. These enzymatically attached reactive groups or functionalities initiate highly efficient intramolecular reactions leading to conversion of C to U analogs in neutral aqueous solution. After conversion, high throughput DNA sequencing of the converted DNA provides a single base-resolution methylation profile; unmethylated cytosines are sequenced as thymines, while methylated cytosines are sequenced as cytosines.

Bisulfite genomic sequencing is the current gold standard method for methylome analysis (Katja et al., 2013). This method entails the bisulfite treatment of DNA which causes the conversion of unmethylated C to U. Methylated C's remain unaffected. These methylated C's are thereafter identified upon sequencing of the bisulfite treated DNA, as these are the only C's read as cytosine. On the other hand the unmethylated cytosines (that have been converted to U) are read as thymidines There are a number of innovative aspects to this method, presenting several advantages over BGS. First, in this new approach, the CpG site-specific bacterial DNA methyltransferase M.SssI, which methylates all CpG dinucleotides, transfers conversion chemical groups to the 5 position of cytosines in every unmethylated CpG dinucleotide; non-CpG cytosines and 5-methyl C's are not modified due to the enzyme's strict CpG site recognition and high regioselectivity for the 5 position of C. This has distinctive advantages over traditional bisulfite chemistry including the specific conversion of only unmethylated CpG sites, instead of all unmethylated cytosines when bisulfite is used. This increases the information content for the converted sequences and thereby facilitates alignment of reads to the genome, meaning that it is still possible to identify the corresponding sequences of the converted sequence in the genome.

In contrast, upon BGS, all unmethylated C's are converted. This is an immense number of nucleotides that is being converted so much so that often the converted DNA no longer resembles the parent DNA. Therefore, it becomes hard to identify which stretches in the converted DNA corresponds to the same regions in the parent DNA. BGS thus causes the loss of sequence information. Further, by not directly affecting all C's, the chemical conversion used in our method promises to be less prone to DNA cleavage and will cause far less DNA damage than does BGS, enabling sequencing of longer DNA fragments.

In addition, by not directly affecting all cytosines the conversion chemistry is less toxic and causes far less DNA damage than does BGS, which enables the sequencing of longer DNA fragments (current bisulfite protocols are often limited to the analysis of DNA fragments <500 bp).

Second, upon being modified with reactive groups at the 5 position of cytosines, further conversion is limited to the modified C's and occurs in an intramolecular fashion with high efficiency. Moreover, the versatility of conversion chemistries allows us to finely optimize the conversion to secure the smallest extent of DNA damage and retain the maximum DNA sequence information.

Third, bisulfite conversion also faces the disadvantage of requiring single stranded DNA; double stranded DNA is resistant to conversion and is read as methylated even when unmethylated. Hence, bisulfite treatment, must be performed under very harsh conditions (0.2 N NaOH at elevated temperatures for several hours), necessitating usage of large amounts of starting DNA (Warnecke et al., 2002).

Fourth, the reliability of BGS is further reduced by the resistance of CpG dinucleotides, in certain sequence contexts, to bisulfite conversion (Warnecke et al., 2002).

Fifth, PCR (Polymerase Chain Reaction i.e. a means of amplifying DNA) amplification step after the conversion step favors product derived from unconverted or methylated starting material, introducing large bias (Warnecke et al., 1997). In contrast, due to its specificity, high efficiency and mild conversion conditions, DNA MTase-aided photo-conversion of C promises to eliminate the deficiencies of BGS such as loss of information content, reactivity of non-CpG cytosines, and need for large amounts of long DNA as starting material.

Bisulfite sequencing and the limitations thereof are discussed above. In contrast, due to its specificity, high efficiency and mild conversion conditions, DNA methyltransferase-aided conversion of C retains the important advantage of BGS (the ability to test every CpG dinucleotide for methylation) while avoiding its deficiencies such as loss of information content, reactivity of non-CpG cytosines, and the requirement for large amounts of long DNA as starting material. The new method is thus simpler and more amenable to automation and DNA sample preparation for high throughput next-generation sequencing than existing methods, providing a novel and robust approach to comprehensively profile genome-wide DNA methylation patterns.

Advances in chemistry and biology research into DNA methyltransferases have generated a novel tool kit to chemically modify the 5 position of C in unmethylated CpG's in order to initiate a conversion reaction on this specific C. Versatile chemical mechanisms are explored for suitable C to U conversion in DNA. For example, it has been reported that photo-irradiation can generate a 5,6-cyclobutane intermediate between an alkene and the 5,6 position double bond of a C via a 2+2 cycloaddition, leading to the interruption of the conjugate system, and deamination at the 4 position (Haga et al., 1993). Notably, this chemistry has been applied to on-DNA conversion of C to U (Matsumura et al., 2008, Fujimoto et al., 2010).

Figure 2:
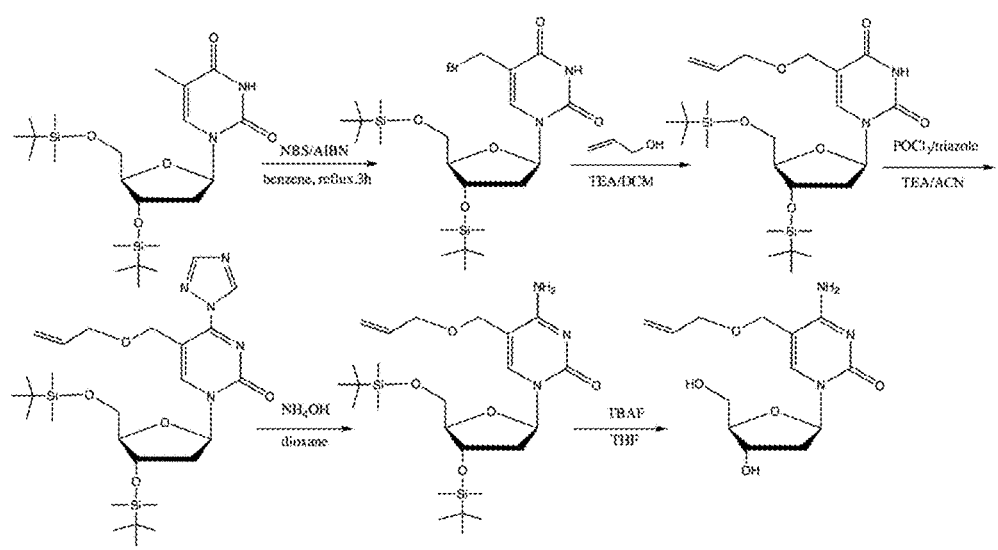
FIG. 2. Synthetic scheme of 5-All-OMC.

Example 2: Photochemical Conversion of 5 Position-Modified Deoxycytidine to Deoxyuridine Analog For the enzyme-aided site-specific C to U conversion, it is a prerequisite that the 5 position attached chemical conversion moiety should be able to trigger an intramolecular reaction resulting in C to U conversion. Since such an example has never been reported, we started our research by designing and synthesizing deoxycytidines with their 5 position derivatized with photo-reactive moieties. We designed 5 position-modified C by attaching a double bond-containing chain with 1 to 5 carbon units inserted between the double bond and the 5 position of C. We have synthesized one of the model compounds 5-allyloxymethyl-dC (5-All-OMC), in which the double bond is 3 carbon units front the 5 position following the synthetic route shown in FIG. 2. The product was fully characterized by HR MS and $^1$H NMR.

Photo-irradiation of 5-All-OMC at about 300 nm was then conducted in aqueous solution for up to 12 h, and the reaction products separated and monitored by HPLC and UV absorption. MS and HPLC profiles indicate that 5-All- OMC (MW 298) is converted photochemically to a new product 5-All-OMU (MW 299) with high efficiency (FIG. 3).

Figure 4:
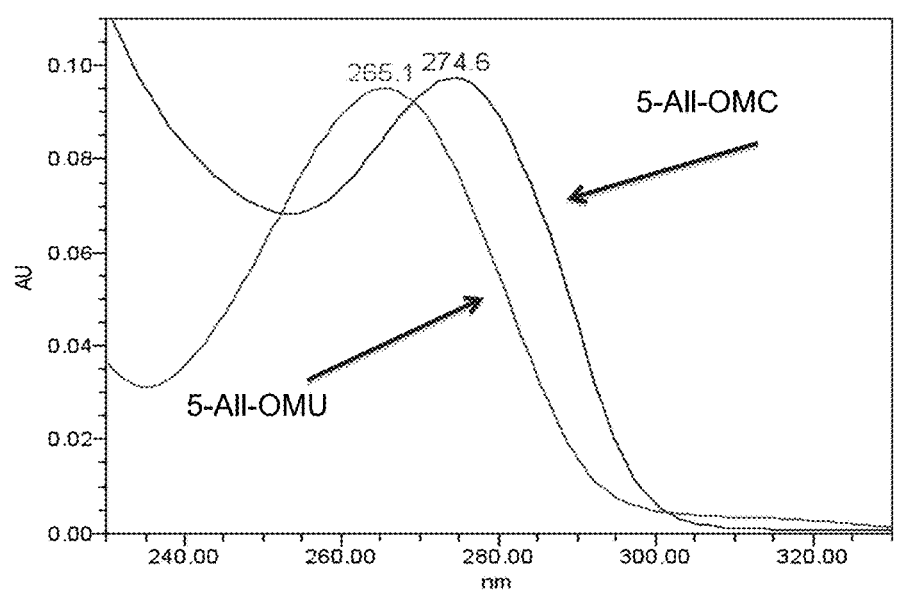
FIG. 4. UV absorption spectra of the new photochemically generated product (5-All-OMU) reveals maximum absorption at 265 nm, typical of U, while the starting material (5-All-OMC) shows the expected absorption of C with $\lambda max=274$ nm.
Figure 5:
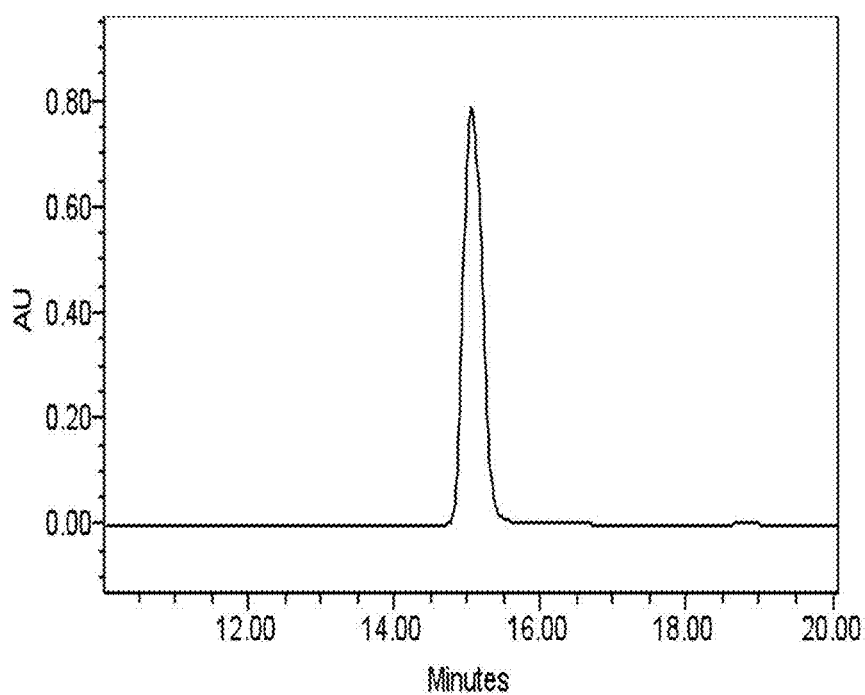
FIG. 5. The mixture of the photochemically generated product from 5-AOMC and the synthesized 5-AOMU shows a single peak in HPLC analysis.

Both C and 5-methyl-C remain intact after photo-irradiation under the same conditions. UV absorption spectra of the new photochemically generated product (5-All-OMU) reveals maximum absorption at 265 nm, typical of U, while the starting material (5-All-OMC) shows the expected absorption of C with λmax-274 nm (FIG. 4). The results show that 5-All-OMC is converted to a U analog by means of photo-irradiation. To further verify this conversion, 5-All-OMU was synthesized and characterized. The mixture of the photochemically generated product from 5-All-OMC and the synthesized 5-All-OMU shows a single peak in HPLC (FIG. 5), indicating that the new product is identical to 5-All-OMU. The photochemically generated 5-All-OMU was also characterized by $^1$HNMR.

These data clearly demonstrate that modification at the 5 position of C with an alkene moiety can lead to formation of a U analog by photo-irradiation under mild conditions with high efficiency.

Example 3: Site Specific Photochemical Conversion of C to U Analog in DNA

Figure 6:
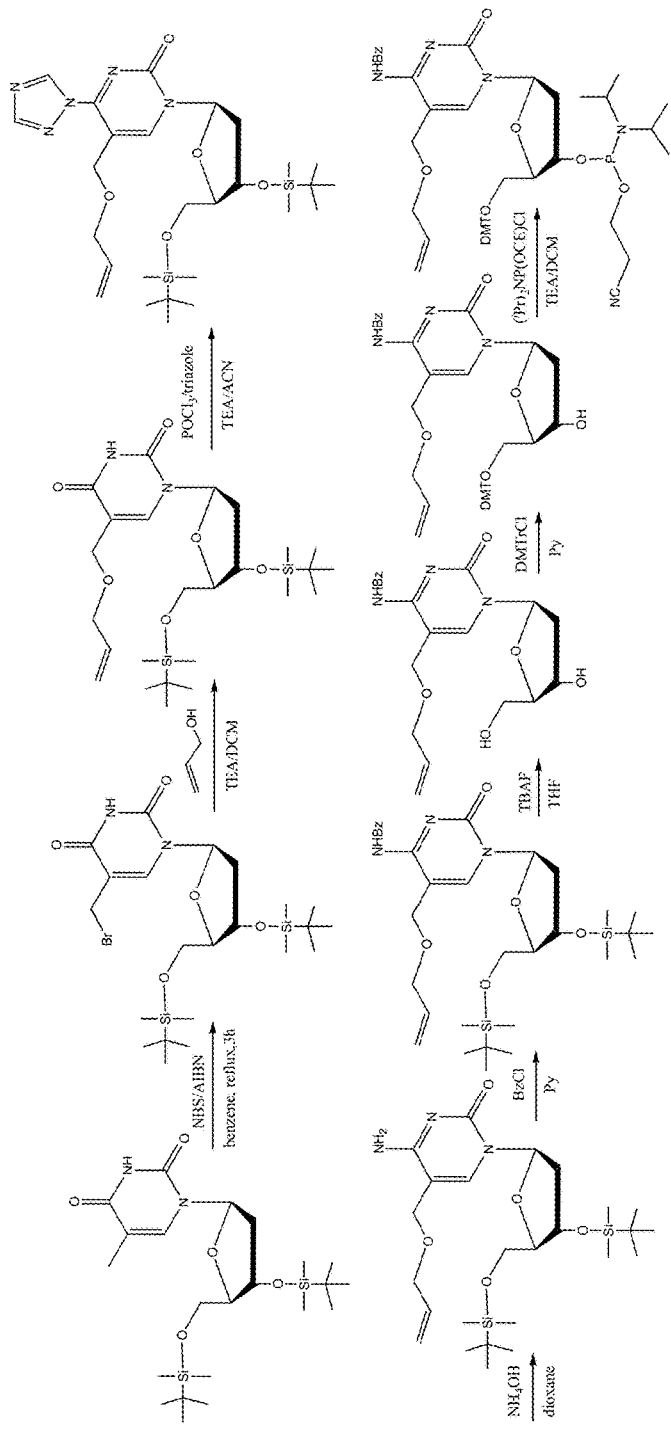
FIG. 6. Synthesis of 5-All-OMC phosphoramidite.
Figure 7:
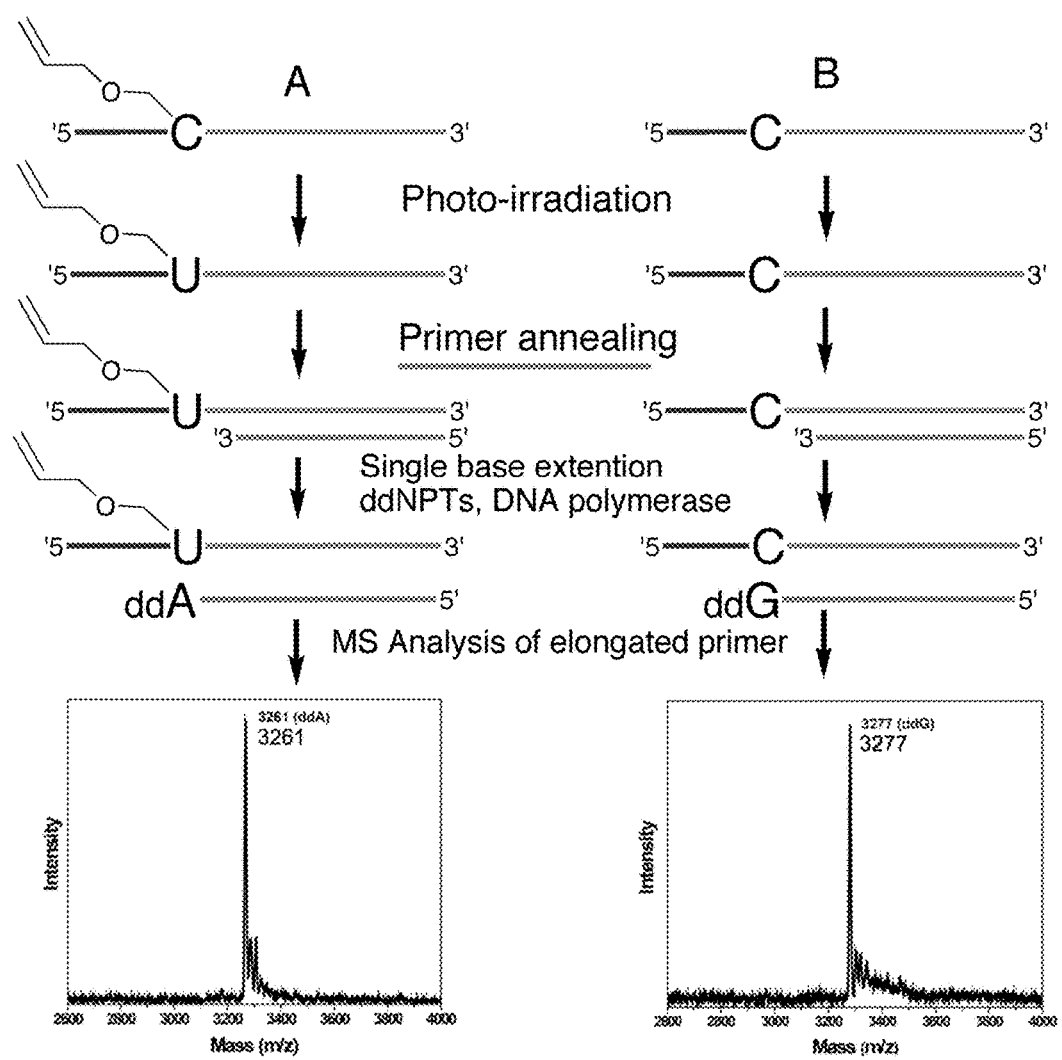
FIG. 7. Single base extension MS analyses of primer elongation show conversion of 5-All-OMC to 5-All-OMU (C to U) in a DNA strand after photo-irradiation, resulting in a primer extension product (MW 3261) incorporating a ddA (A), while in a counterpart DNA strand, unmodified C remains intact, resulting in a ddG incorporated extension product (MW 3277) (B).

To test the feasibility of the photochemistry approach for converting C to U on a real DNA chain, a fully protected 5-All-OMC phosphoramidite was synthesized (FIG. 6) and 5-All-OMC (C*) was incorporated into a 16mer oligonucleotide 5'-TACGA(C*)GAGTGCGGCA-3' (SEQ ID NO: 1) via standard oligonucleotide synthesis. After HPLC purification, the modified 16mer was characterized by MALDI-TOF MS yielding a peak with MW of 5001, equal to the calculated mass. Then photo-irradiation of oligo 5'-TACGA(C*)GAGTGCGGCA-3' (SEQ ID NO: 1) was conducted to convert C* to a U analog. The outcome for conversion of C* in DNA was detected by using single base extension-MS analysis (FIG. 7). In this analysis, the photo-irradiated oligonucleotide was annealed with a primer 5'-TGCCG-CACTC-3' (MW 2964) (SEQ ID NO: 2), then incubated with ddNTPs and DNA polymerase. With the aid of DNA polymerase, one of the 4 ddNTPs can be selectively incorporated onto the 3' end of the primer. Photo-chemistry induced conversion of C to U should be able to direct the incorporation of ddA, resulting in an elongated primer with a MW of 3261, otherwise ddG should be incorporated giving an elongated primer of MW 3277.

Actual MS measurement of the one-base elongated primer shows the MW as 3261, which matches the MW of the primer incorporated with an single ddATP, thus the existence of a complementary U on the template was confirmed, and the photochemical conversion of the C* to a U analog on DNA demonstrated (FIG. 7 top). In the control experiment, photo-irradiation of the unmodified counterpart 5'-TAC-GACGAGTGCGGCA-3' (SEQ ID NO: 3) was conducted under the same conditions. The single base extension MS analysis of the resulting primer elongation product gave a MW of 3277, which matches the MW of the primer extended with a single ddGTP (FIG. 7 bottom), unambiguously showing that only if the 5-position of C is modified with a photo-reactive moiety, can it be converted to the U analog in a DNA fragment with high efficiency. We also measured possible photoirradiation-induced DNA damage. Under the conditions we used (300 nm, over 10 h) no DNA damage was observed.

The above studies show that 5 position modification of C with a photo-reactive moiety provides us with a new route for highly efficient C to U conversion, without the drawbacks of bisulfite conversion. Therefore the feasibility of CpG site-specific conversion of C to U is demonstrated and the results offer the basis and rationale for the DNA methyltransferase-aided DNA methylation profiling method described.

Example 4: Exploration of C-U Conversion Chemistry Triggered by a 5 Position Reactive Moiety A library of 5 position-derivatized deoxycytidine model compounds is used to systematically screen and optimize the C-reactive functionalities that most efficiently convert C into U. The model compounds are partially listed in FIG. 8.

Species of AdoMet analogs used as DNA methyltransferase substrates are sulfonium derivatives of AdoHcy, in which photoactive groups (R) replace the methyl group in AdoMet (FIG. 8). Such AdoMet analogs containing photoactive groups (R) serve as substrates for CpG specific DNA methyltransferase, such as M.SssI, and as a result of enzymatic reaction, these photoactive groups (R) can be transferred to the 5 position of C of unmethylated CpG dinucleotides in DNA.

(1) The photoactive groups (R) include alkenes (FIG. 8, $a$, $b$, $a$, $d$, $e$) which form a cyclobutane intermediate with 5,6 double bond of C upon photo-irradiation, and further result in C to U conversion. The photoactive groups (R) also include alkenes modified with $R_1$, $R_2$ and $R_3$, which facilitates the photoreaction. $R_1$, $R_2$ and $R_3$ are hydrogen, alkyl, aryl, amide, carboxylic acid, ester, nitro group, cyano group, aldehyde, ketone and sulfonamide. Such an alkene or $R_1$, $R_2$ and $R_3$ modified alkenes can be separated from the sulfur atom in AdoMet analogs by a carbon chain of various length (n=1-8). Either alkyl chains or chemically cleavable structures (such as ester linkers) can be inserted between the above mentioned alkenes and the sulfur atom in AdoMet analogs.

(2) The photoactive groups (R) include the above mentioned alkene conjugated butadiene moiety (FIG. 8, $c$). Such butadienes are linked to the sulfur atom in AdoMet analogs by a carbon chain of various length.

(3) The photoactive groups (R) include maleic anhydride and maleimide analogs (FIG. 8, $f$, $g$, $h$, $i$) which are linked to the sulfur atom in AdoMet analogs by either a saturated or double bond and containing a carbon chain of various length.

(4) The photoactive groups (R) also include N, N double bond containing functionalities that can be used for photo-reaction with the 5,6 double bond of C upon photo-irradiation. For example R can be tetrazole-containing moieties (FIG. 8, $j$, $k$, $l$) which are linked to the sulfur atom in AdoMet analogs by either a saturated or double bond and containing a carbon chain of various length.

Example 5: Syntheses of AdoMet Analogs Containing Photoreactive Groups

Synthesis of AdoMet analogs with the desired extended side chains is carried out by regioselective S-alkylation of AdoHcy with corresponding triflates or bromides of the photoreactive moieties under mild acidic conditions. A diastereomeric mixture of sulfonium is expected after alkylation of AdoHcy, and further RP-HPLC (reverse phase high performance liquid chromatography) purification is conducted to isolate the enzymatically active S-epimer for the subsequent transfer reaction. Examples of the synthesis route for AdoMet analog are shown in FIG. 9. Triflates or bromides of the photoreactive moieties needed for AdoMet analogs synthesis can be synthesized using commercially available starting materials as shown in FIG. 10.

Figure 11:
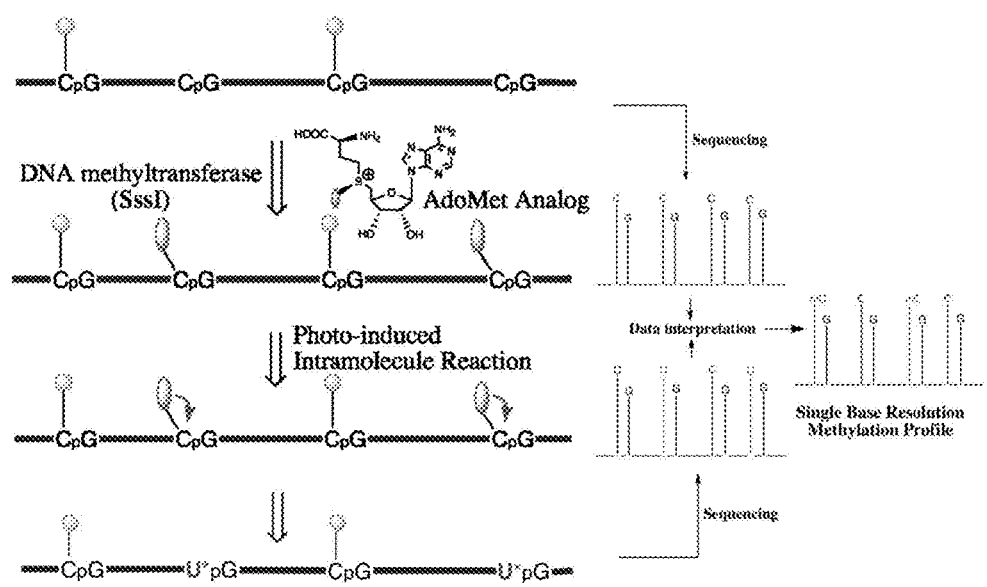
FIG. 11. DNA methylation profiling method based on DNA methyltransferase aided CpG site-specific conversion of C to U. An optimized AdoMet analog is used to deliver the conversion group to an unmethylated CpG so that only modified C can be further converted to U via photo-triggered intramolecular reaction. Subsequent sequencing permits DNA methylation status to be read out at single base resolution.

Example 6: DNA Methyltransferase Guided Transfer of C-Reactive Functionalities on CpG-Containing DNA and Subsequent Site-Specific C to U Conversion AdoMet derivatives are designed based on the results of the experiments above and a possible library of AdoMet derivatives to be synthesized is identified. Synthesis of AdoMet analogs with the desired extended side chains is carried out following reported methods (Dalhoff et al., 2006a, 2006b) by regioselective S-alkylation of AdoHcy with corresponding triflates or bromides of the photoreactive moieties under mildly acidic conditions (FIG. 10). A diastereomeric mixture of sulfonium is expected after alkylation of AdoHcy, and further RP-HPLC purification is used to isolate the enzymatically active S-epimer for subsequent transfer reactions. With AdoMet analogs as substrates, a CpG site-specific DNA methyltransferase (M.SssI) is used to transfer a photo-reactive group to the 5 position of unmethylated cytosines on both synthetic DNA and genomic DNA samples (FIG. 11). MALDI-TOF MS is used to evaluate the efficiency of reactive moiety transfer onto the DNA. Further site-specific photochemical conversion of C to U is carried out using the optimized reaction conditions obtained above. Single-base extension experiments (FIG. 7) are used to study on-DNA conversion efficiency.

The ideal AdoMet analogs are identified, and the conditions for both enzymatic transfer of modifying functionality and on-DNA conversion are optimized. The photo-irradiation conditions are further optimized by screening for optimal wavelength, intensity and other conditions (temperature, time, buffer, pH, and auxiliary ingredients) to maximize the conversion yield and minimize possible side reactions on DNA.

Example 7: Combined DNA Methyltransferase-Aided Conversion Chemistry and Next-Generation DNA Sequencing to Achieve Real-World DNA Methylation Profiling After validation of the DNA methyltransferase-aided CpG site specific conversion of C to U analog, methylation patterns in real-world genomic DNA preparations can be determined from the mammary carcinoma cell line MCF-7, for which we have very large amounts of methylation data. DNA is purified by proteinase K digestion, phenol extraction, and dialysis against 10 mM Tris HCl, pH 7.2. DNA then is reacted with the optimal AdoMet derivative identified above and with M.SssI (New England Biolabs, Inc.). The derivatized DNA then is subjected to high throughput DNA sequencing (FIG. 11), and CpG dinucleotides in the NCBI reference sequence that appear as TpG are scored as unmethylated CpG dinucleotides in the starting DNA. The required software has been developed and validated (Edwards et al., 2010).

After conversion of unmethylated cytosines to uracil analogs, an inert "tail" from the added reactive groups may remain at the 5 position of the cytosine. This tail extends into the major groove of the DNA helix, but it is well known that modification of this position does not interfere with incorporation of nucleotides during polymerase extension, and this position has been modified in a large number of applications (Ju, et al., 2006) including polymerase-catalyzed labeling of DNA and RNA with bulky adducts such as biotin, digoxigenin, and large fluorescent moieties. Such modifications do not markedly interfere with the efficiency or specificity of dNTP incorporation. This allows coupling the well-established sample preparation protocols (emulsion PCR or bridging PCR) and high-throughput DNA sequencing technologies with the enzyme-aided CpG site specific C to U conversion of genomic DNA.

Therefore the workflow (FIG. 11) of this new genome-wide DNA methylation profiling method consists of: 1) enzymatic transfer of C-reactive moiety to 5 position of C; 2) photoreactions leading to C to U analog conversion; 3) sequencing sample preparation; and 4) integrated high-throughput DNA sequencing and data interpretation using any sequencing platform adapted to our enzyme-aided and photo-chemistry based C to U conversion. Validation of this work flow establishes the basis for further automation of the protocols.

Example 8: Detection of Non-CpG Methylation

Some cell types contain non-CpG methylation (Lister et al., 2009), the function of which is currently unknown. We can map ~22% of all non-CpG methylation by a simple modification of the M.SssI protocol by substitution of M.CviJI, which methylates the cytosine in GpC dinucleotides (Xu et al., 1998), for M.SssI, which is specific for CpG dinucleotides.

Example 9: Methylation Profiling and Single-Molecule Sequencing

Our technology also can be used in single-molecule sequencing technologies that identify bases by electronic properties as the DNA passes through nanopore chambers. AdoHcy derivatives are developed that allow accurate identification of derivatized cytosines so as to distinguish cytosine from 5 methyl cytosine. This represents a simple extension of the technology that allows the extremely fast and economical mapping of genomic methylation patterns. The Methyl-seq method elaborated here provides converted DNA that can be sequenced not only by all current methods but is also perfectly suited to the new single molecule methods under development.

Example 10: Photo-Irradiation Mediated Conversion of C to U at a Wavelength which is Benign to DNA Among versatile chemical mechanisms which can be explored for suitable C to U conversion in DNA, the most promising chemical mechanism that can convert C, that is not methylated at the 5 position, to a U derivative is photo-irradiation mediated [2+2] cycloaddition between an alkene and the 5,6 double bond of C. Photo-irradiation mediated (2+2) cycloaddition leads to the interruption of the conjugate system in C and produces a 5,6-cyclobutane intermediate between an alkene and the 5,6 position double bond. Due to the interruption of the conjugate system, further deamination at the 4 position (Haga, et al., 1993) can readily occur resulting in formation of a U derivative. Notably, this chemistry has been applied to on-DNA conversion of C to U (Matsumura, et al., 2008, Fujimoto, et al., 2010). Methylated C cannot undergo [2+2] cycloaddition with alkene substrates and therefore is not converted into U in this process.

We have demonstrated that a C with its 5 position modified with an alkene-bearing chemical group can be photoconverted to a U analog by 300 nm photo-irradiation using the model compound 5-allyloxymethyl-dC (5-All-OMC).

Moreover, we propose to use a light source for photo-irradiation that has no damaging effect on DNA. To this end, further chemical modifications at the photo-reactive double bond were proposed to extend the conjugation system so that the optical absorption properties of the alkene reactive center can occur at a longer wavelength of light, ensuring photocyloaddition and oxidative deamination upon irradiation with wavelengths above 350 nm and into the visible spectrum.

Conjugation-extension modifications provide a wide range of olefins that could be tested to optimize the suitable double bond containing species that can be used to design and synthesize AdoMet analogs. A variety of complementary double bond species modified with either electron withdrawal groups or electron donating groups can be used to derivatize AdoMet analogs. On the other hand, the distance between these modified double bonds and the 5,6 double bond of C is also taken into consideration for a space and energy favorable intramolecular cycloaddition.

Figure 12:
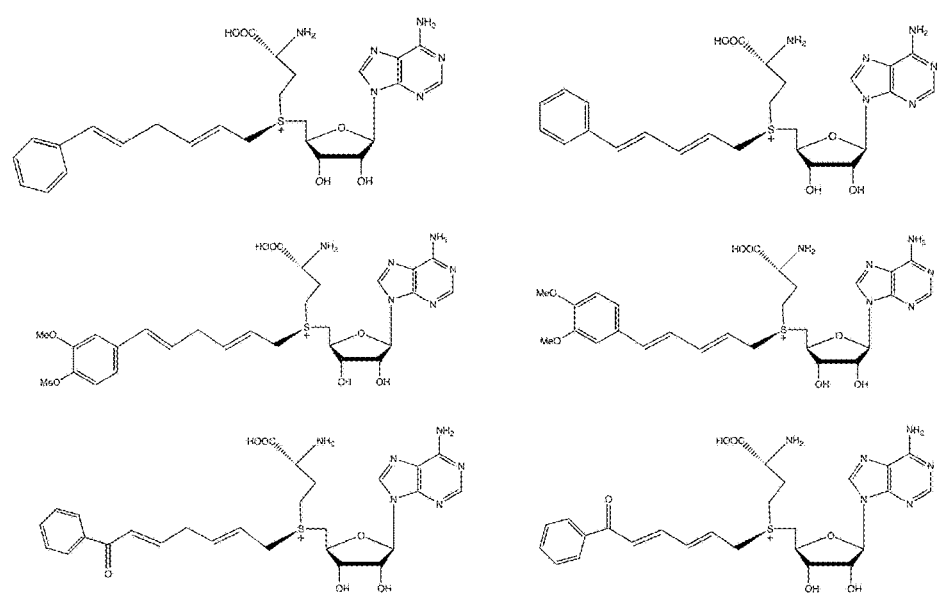
FIG. 12. Example structures of AdoMet analogs in which the photoactive alkene is modified with phenyl, dimethoxyphenyl groups or other groups.
Figure 13:
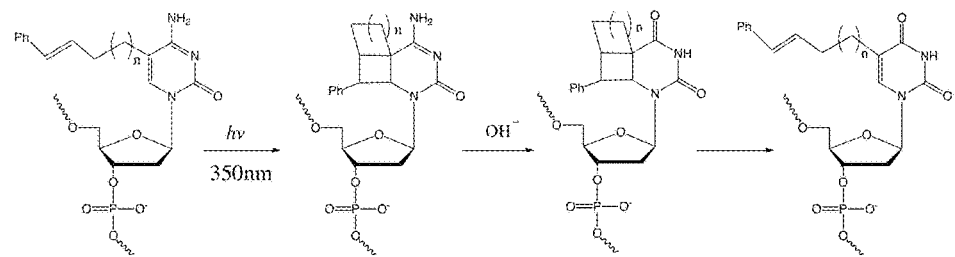
FIG. 13. Photocatalyzed conversion of an enzymatically modified C in DNA to a U derivative via a cycloaddition intermediate when C is modified with a long-wavelength absorbing double bond, such as a phenyl modified alkene.

FIG. 12 shows example structures of AdoMet analogs in which the photoactive alkene is modified with phenyl, dimethoxyphenyl or other groups. Attachment of long-wavelength absorbing photo-reactive moieties at the 5-position of CpG sites can be carried out by using DNA methyltransferase and such designed AdoMet analogs as the substrate. Subsequent C to U conversion will be achieved by using DNA-safe photo-irradiation (above 330 nm) as shown in FIG. 13. The photo-reactive moieties at the CpG sites directly harvest light energy from long-wavelength irradiation and initiate further cycloaddition with the 5,6 double bond in C's. The cyclobutane intermediate of C can easily undergo hydroxylation and deamination, resulting in the formation of U analogs within DNA and ultimately achieving CpG site-specific C to U conversion under photo-irradiation conditions.

Figure 33:
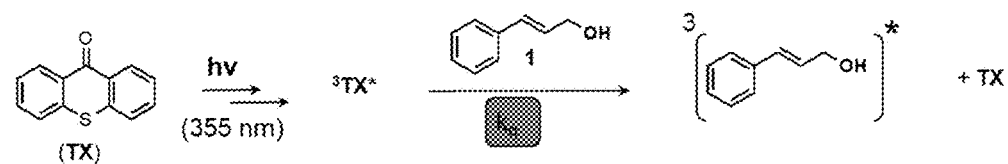
FIG. 33. To determine the rate constant of triplet energy transfer from the triplet sensitizer thioxanthone to the styrene chromophore of PhAll-OMC by laser flash photolysis, the model compound cinnamyl alcohol was used which contains the styrene chromophore. Photoexcitation of thioxanthone generated triplet states which were quenched by cinnamyl alcohol with a rate constant of $k_q$=7.8×10$^9$ M$^{-1}$s$^{-1}$ which is close to the maximum rate constant possible for triplet energy transfer.

Fluorescence studies on an AdoMet analog similar to that shown in FIG. 13 have demonstrated that the photo-excited styrene chromophore (Ph-=-) is rapidly deactivated by either [2+2] cycloaddition and/or singlet state energy transfer from the styrene chromophore to C (cf. FIG. 33). Taking advantage of the higher molar absorptivity of the styrene chromophore, energy transfer to the C chromophore can also lead to [2+2] cycloaddition and subsequent conversion to U.

For a more efficient photoreaction leading to formation of photocycloaddition intermediates, a variety of species of photo-sensitizers or photo-catalysts will also be used to facilitate the excitation, especially those having long wavelength absorption properties such as thioxanthone (TX) and its derivatives. Upon long wavelength irradiation, TX can be excited to generate a triplet$^3$(TX)* intermediate which is capable of transferring energy and generating triplet excited states of the above mentioned (FIGS. 12 and 13) 5-position modified double bond containing moieties.

The rate constant for such a triplet energy transfer from TX to the styrene chromophore in an AdoMet analog similar to that shown in FIG. 13 was determined by laser flash photolysis to be $7.8 \times 10^9$ Ms$^{-1}$. This high rate constant is close to the theoretical maximum rate constant for triplet energy transfer. The generated triplet excited double bond containing moiety readily reacts with the 5,6 double bond of C leading to cyclobutane intermediate formation, which facilitates C to U conversion.

Furthermore, [2+2] cycloadditions are known to proceed generally more efficiently from triplet excited states than from singlet excited states (generated by direct photolysis) because of the longer lifetime of triplet excited states.

Alternatively, in addition to a variety of 5 position modifying groups which facilitate the C to U photo-conversion, mild and efficient photo reaction conditions are applied in C to U conversion in real-world DNA by using visible light combined with the use of the photocatalyst Tris (bipyridine) ruthenium (II) chloride (Ru(bpy)$_3^{2+}$).

Figure 14:
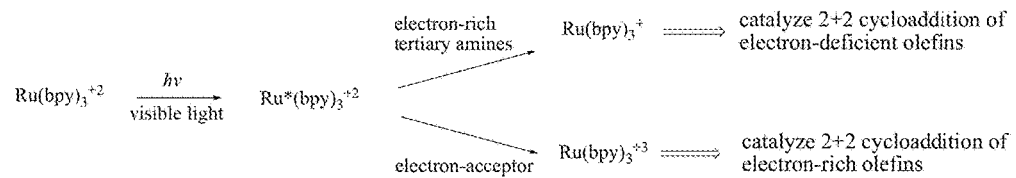
FIG. 14. Two-path photocatalysis mechanism of $Ru(bpy)_3^{2+}$, a versatile photocatalyst which can engage [2+2] cycloaddition of both electron-deficient and electron-rich olefins.

Irradiation of Ru(bpy)$_3^{2+}$ with visible light ($\lambda$max=452 nm) produces a photoexcited state Ru*(bpy)$_3^{2+}$ which can extract an electron from a relatively electron-rich amine base. The resulting Ru(bpy)$_3^{3+}$ complex then reduces an aryl enone to the key radical anion intermediate involved in [2+2] cycloaddition. On the other hand Ru*(bpy)$_3^{3+}$, can also pass an electron to an electron acceptor, the resulting Ru(bpy)$_3^{2+}$ then oxidize electron-rich styrene, affording a radical cation that would undergo subsequent [2+2] cycloaddition. Thus through either a reductive quenching cycle or an oxidative quenching cycle, Ru*(bpy)$_3^{2+}$ turns out to be a powerful photoredox catalyst for [2+2] photocycloaddition of olefins (Ischay et al., 2008; 2010; Du et al., 2009). Its two-path photocatalysis mechanism makes Ru(bpy)$_3^{2+}$ a versatile photocatalyst which can engage [2+2] cycloaddition of both electron-deficient and electron-rich olefins (Michael, et al., 2008; 2010) (FIG. 14). This advantage provides us with a wide range of both electron-deficient and electron-rich olefins from which we screen and optimize the suitable double bond containing species that can be used to design and synthesize AdoMet analogs. Upon attachment of photo-reactive moieties at the 5-position of CpG sites by using DNA methyltransferase and such AdoMet analogs as substrate, subsequent C to U conversion is achieved by Ru$^{2+}$-visible light photocatalysis. Thus, combining the use of this Ru$^{2+}$ complex as a photocatalyst and visible light irradiation of DNA with CpG modification provides another option for site-specific C to U conversion.

Figure 15:
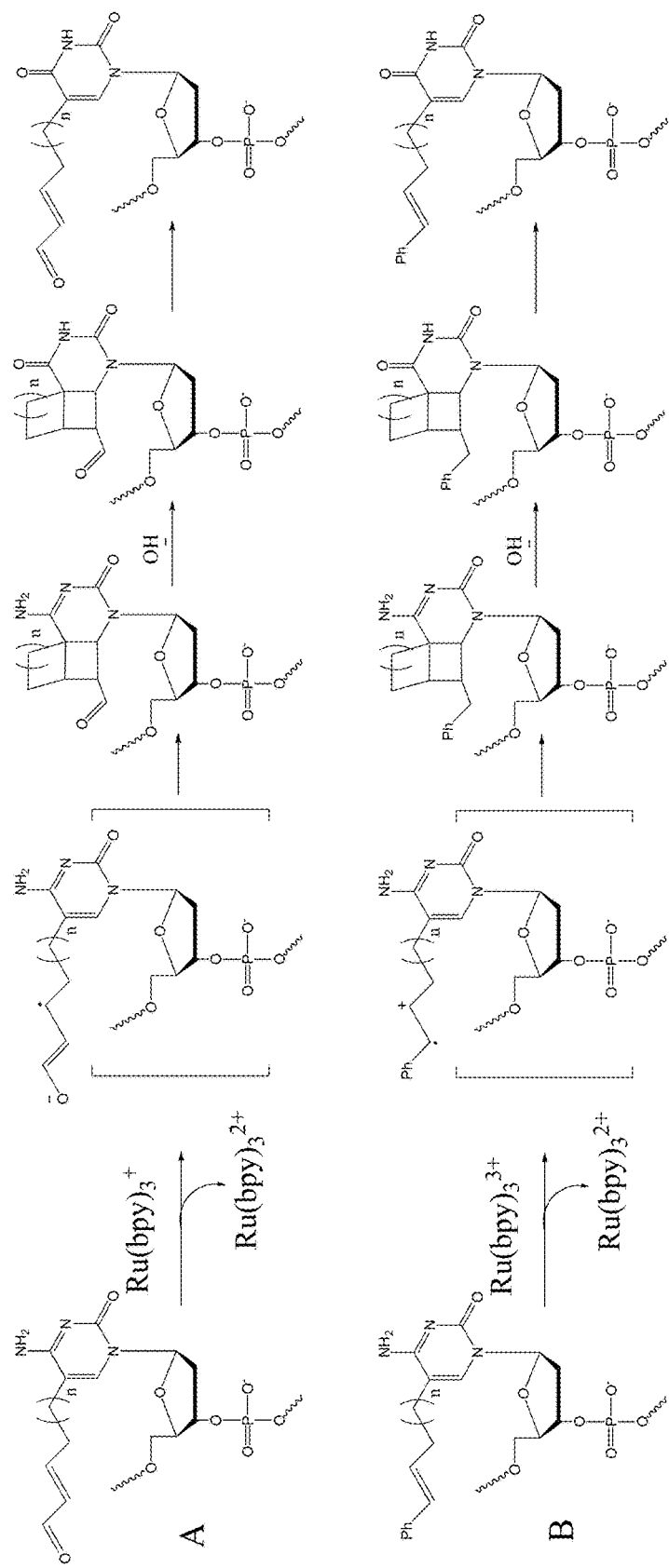
FIG. 15. A. $Ru(bpy)_3^{2+}$-visible light catalyzed photo-conversion of a 5-position modified C in DNA to a U via a cycloaddition intermediate when C is modified with an electron-deficient double bond. B. $Ru(bpy)_3^{2+}$-visible light catalyzed photo-conversion of a 5-position modified C in DNA to a U via a cycloaddition intermediate when C is modified with an electron-rich double bond.

FIG. 15 shows two examples of Ru(bpy)$_3^{2+}$-visible light catalyzed photo-conversion of 5-position modified C to U in DNA. Examples of Ru(bpy)$_3^{2+}$ complex can be Ru(bpy)$_3$Cl$_2$ and Ru(bpy)$_3$(PF$_6$)$_2$. The visible light photocatalysis reaction mixture contains the Ru(bpy)$_3^{2+}$ complex, tertiary amines (for example N,N-diisopropylethylamine (i-Pr$_2$Net)), quaternary ammonium cations (such as MV(PF$_6$)$_2$, methyl viologen, or MV$^{2+}$), Mg$^{2+}$ or Li$^+$. The light source can be ordinary household bulbs or lasers (with wavelength from 400 nm-600 nm).

Therefore, the conditions for photoreaction mediated C to U conversion include photo-irradiation at wavelengths from 300 nm to 700 nm, at a temperature between 0° C. and 90° C. in a buffered solution with pH between 4 and 10, with or without an above mentioned photosensitizer or photocatalyst along with other necessary ingredients.

Example 11: Mutagenesis of M.SssI

A method for whole-genome, single-CpG methylation profiling that is effective at the single-cell level using novel enzymatic activities and a photochemical strategy that utilizes synthetic analogs of S-adenosyl-L-methionine (AdoMet) is being developed. A crucial component of the technology is the CpG specific cytosine-5 DNA methyltransferase, M.SssI.

The bacterial restriction methyltransferase M.SssI from a *Spiroplasma* species normally transfers sulfonium-linked methyl groups from S-adenosyl L-methionine (AdoMet) to the 5 positions of cytosine residues in cytosine-phosphate-guanosine (CpG) dinucleotides in duplex DNA. Previous studies have shown that M.SssI can transfer other sulfonium-linked moieties from synthetic AdoMet derivatives to DNA, as described in Klimauauskas et al., U.S. Patent Application Publication No. 2012/0088238 A1. Kriukiene et al. (2013) demonstrated the 100 fold increase in the transferase activity of M.SssI upon substitution of Glutamine 142 and Aspargine 370 to Alanines. However, while a beneficial reduction in selectivity results, it is almost certain that a detrimental decrease in enzymatic activity is incurred due to the increased hydrophobicity of the AdoMet binding site and the drastic reduction in the size of the amino acid side chains in the AdoMet binding site. We perform a similar mutagenesis on M.SssI, and also generate mutants with Glutamine 142 and Aspargine 370 substituted to Serine.

Figure 16:
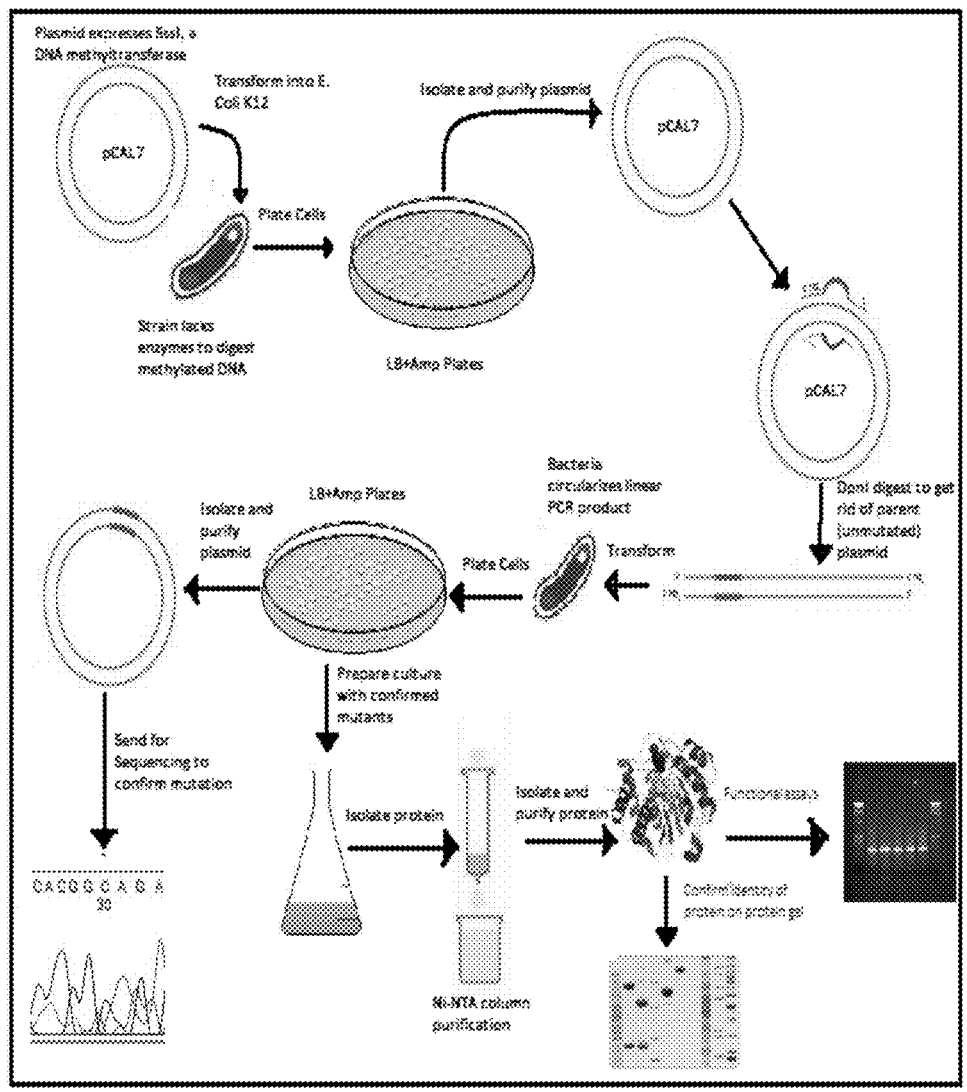
FIG. 16. Outline of the methods for the generation, isolation, purification and analysis of the functional activity of mutant M.SssI.

FIG. 16 summarizes the experimental design for the generation, isolation and analysis of the activity of mutant M.SssI.

M.SssI has been engineered to increase the efficiency of transfer of reactive groups from synthetic AdoMet analogs. Mutations Q142 and N370 are both located in the active site of M.SssI and the mutations of these residues to non-polar alanines possibly opens up the active site thereby facilitating more efficient binding to substrates larger than a methyl group. Here, the efficiency of M.SssI upon substitution of the aforementioned amino acids to serine is further investigated. It was hypothesized that the serine mutant will be more stable than the alanine variant in the presence of DNA and AdoMet by restoring the hydrophilic nature and relaxed specificity of the AdoMet binding site while maintaining the improved transfer rate of the alanine mutants. We also designed M.SssI Q142S/N370A and Q142A/N370S variants to further explore the effect of different combinations of substitutions at these two sites on the transfer activity of the enzyme.

Bacterial Strain

The following strain was used for expressing M.SssI: *E. coli* K12 strain ER1821 F-glnV44 e14-(McrA-) rfbD1 relA1 endA1 spoT1 thi-1 Δ(mcrC-mrr) 114::IS10 (Wait-Rees et al 1991). The strain was obtained from New-England Biolabs.

The bacterial strain ER1821 was selected because it has genes deleted that code for McrBC, an enyme that specifically restrict DNA modified by different sets of sequence-specific cytosine methylases.

Bacteria were routinely grown in LB medium [Sambrook, 1989] at 37° C. They were made chemically competent using the standard $CaCl_2$ method (Tu et al., 2008). Competent cells had a transformation efficiency of ~$10^7$ cfu/μg DNA. A batch of cells were also made electrocomptetent using a standard glycerol protocol [Sambrook, 1989]. Electrocompetent cells had a transformation of ~$10^8$ cfu/μg DNA.

Plasmids and Oligonucleotides

The expression construct pCAL7 was selected because it directs the expression of the DNA M.SssI variant present in *Spiroplasma* species and has the same sequence specificity as mammalian DNA methyltransferase (CpG), but a higher turnover number and no requirement for hemimethylated substrates (Renbaum and Razin, 1992).

pCAL7 is a 7.4 kb plasmid that was used to express the CpG specific DNA methyltransferase M.SssI. Site directed mutagenesis was used to engineer the wild type M.SssI to the His-tagged mutant variant, by mutating two conserved positions in the cofactor-binding pocket (Q142A/N370A). Plasmid transformation was performed following the protocol of Tu et al., 2013. Plasmid miniprep was performed using GeneJET Plasmid Miniprep Kit from Fermentas Life Sciences.

The DNA used for investigating the activity of mutant SssI was a 460 bp PCR amplified fragment of the Dnmt1 gene. It contains a number of CpG sites making it useful for the study of the efficiency of the enzymatic transfer.

Primers were designed for inserting the 6x His-tag, site directed mutagenesis, and sequencing (for verifying the mutation in the sequence). The primers used for mutagenesis were designed using Stratagene software. The primers for sequencing were manually designed to anneal ~100 bp from the expected mutation. For the 6x his-tag insertion, a method similar to the one described by Naismith et al. (2008) involving the use of non-overlapping primer pairs was designed to improve the chances of inserting the large 18 bp fragment. Table 1 as follows lists the primers used for site directed mutagenesis. Primers were ordered from Integrated DNA Technologies.

TABLE 1

Primer pairs used for 6x His tag insertion (His), substitution of Q142 and N370.

| Primer Sequence | Primer Name |
|---|---|
| 5'-atacccctgttgagataagtctgcacaaggaaatga atatgttaataaatctatattttcaaag-3' (SEQ ID NO: 4) | Q142 sense |
| 5'-ctttgaaaaatatagatttattaacatattcattt ccttgtgcagacttatctcaacagggtat-3' (SEQ ID NO: 5) | Q142A antisense |
| 5'-tcgcttccaaaacttctactgatattgaagctcca caaacaaatattttttgattttcag-3' (SEQ ID NO: 6) | N370A sense |
| 5'-ctgaaaatcaaaaaatatttgtttgtagagcttca atatcagtagaagttttggaagcga-3' (SEQ ID NO: 7) | N370A antisense |
| 5'-ttattaacatattcatttccttgttcagacttatc tcaacagggtattc-3' (SEQ ID NO: 8) | Q142S sense |
| 5'-gaatacccctgttgagataagtctgaacsaggaaat gaatatgttaataa-3' (SEQ ID NO: 9) | Q142S antisense |
| 5'-tgaaaatcaaaaaatatttgtttatggaagttcaa tatcagtagaaattttggaagcg-3' (SEQ ID NO: 10) | N370S sense |
| 5'-cgcttccaaaacttctactgatattgaacttccac aaacaaatattttttgattttca-3' (SEQ ID NO: 11) | N370S antisense |
| 5'-gcttccaaaacttctactgatattaaatttccaca aacaaatattttttgatttc-3' (SEQ ID NO: 12) | S370N_ antisense |
| 5'-gaaaatcaaaaaatatttgtttgtggaaattcaat atcagtagaagttttgqaagc-3' (SEQ ID NO: 13) | S370N_sense |
| 5'-cttttgaatacccctgttgagataagtcttgacaag gaaatgaatatgttaataaatct-3' (SEQ ID NO: 14) | S142Q_ antisense |
| 5'-agatttattaacatattcatttccttgtcaagact tatctcaacagggtattcaaaag-3' (SEQ ID NO: 15) | S142Q_sense |
| 5'-*gaaacagaccATGcaccatcaccaccacat* AGCAAAGTAGAAAATAAAACAAAAAAAC-3' (SEQ ID NO: 16) | His sense |

TABLE 1 -continued

Primer pairs used for 6x His tag insertion (His),
substitution of Q142 and N370.

| Primer Sequence | Primer Name |
|---|---|
| 5'-*gtg*CAT*qgtctgttt*cctgtgtgaaattgttat ccgc-3' (SEQ ID NO: 17) | His antisense |

The His insert in the primer is underlined and the overlapping regions between the His sense and antisense primers are in italics.

Site-Directed Mutagenesis Using Chemically Competent Cells

Site-directed mutagenesis was carried out on the 7.4 kb pCa17 plasmid to insert the His tag and the substitution mutations. Mutagenesis was carried out by oligonucleotide directed mutagenesis outlined in the QuickchangeII protocol by Agilent Technologies, using the primers listed in Table 1. In brief, the plasmid was PCR amplified with a primer set, transformed into ER1821 cells and plated on ampicillin plates. 2-4 colonies were picked for miniprep (using GeneJET Plasmid Miniprep Kit). The miniprep colonies were then sent for sequencing along with the sequencing primers to GeneWiz Inc to confirm success of mutagenesis.

Site-Directed Mutagenesis Using Electrocompetent Cells

Site-directed mutagenesis was carried out on pCa17 plasmid to introduce the substitution mutations using the protocol outlined in the QuickchangeII-E protocol by Agilent Technologies. In brief, the plasmid was PCR amplified using the mutagenesis primers, chloroform extracted, ethanol precipitated, diluted to 6 µl with water. 2 µl of this solution was electroporated into 50 µl of electrocompetent *E. coli* which was then diluted by addition to 200 µl of SOC. 50 µl of this solution was then plated on ampicillin plates following which the aforementioned miniprep and sequencing procedures were followed.

Figure 36:
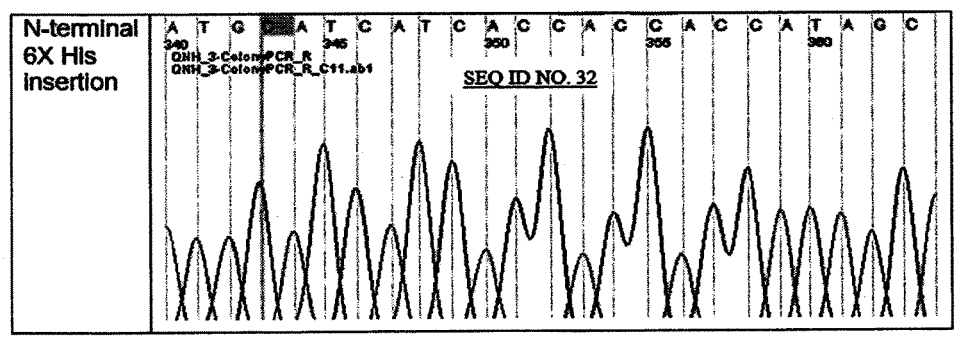
FIG. 36. Sequencing confirmation of N-terminal 6× His tag insert.

The wild type and mutant variants that were made or are in the process of being designed along with their names are provided in FIG. 17. The substitutions generated by site-directed mutagenesis were confirmed by sequencing, the results of which are summarized in FIG. 35. The insertion of the His-tag was similarly confirmed by sequencing (FIG. 36).

Sequencing the plasmid after mutagenesis confirmed the presence of the substitutions. For insertion of the 6×His tag, a set of non-overlapping primers was designed using PCR conditions described by Naismith et al (2008), such that the newly synthesized DNA could be used as the template in subsequent amplification cycles. This method was very inefficient. This caused applicants to use the SS plasmid, the plasmid into which the His tag was initially inserted as a template to generate the other mutant variants as well as the His-tagged wild-type variant.

In order to increase the efficiency of the mutagenesis electrocompetent cells were made and chemical transformation was substituted with electroporation for the transformation of E4102S with the mutagenesis product. The electrocompetent cells had 10 fold greater transformation efficiency than their chemically competent counterparts. The use of these cells, as expected, drastically improved the number of colonies per mutagenesis reaction to ~50 colonies (compared to just 1 or 2 for mutagenesis with chemically competent cells). However, sequencing results revealed greater than 50% of these colonies contained the parental DNA without the desired mutation. Observation of the possible fragments that could be generated using NEBCutter, suggested that perhaps the 1350 bp fragment (which contains the M.SssI sequence, origin of replication and Amp resistance sequence), as observed as a band in the gel, was recircularizing within *E. coli*.

M.SssI activity was estimated by a restriction protection assay. M.SssI expressing pCa17 plasmid was isolated using the GeneJET Plasmid Miniprep Kit and tested for methylation using the methylation sensitive restriction enzyme HpaII. 200 ng of plasmid was incubated with 1 U of HpaII and 1× CutSmart Buffer (supplied by New England Biolabs) and incubated at 37° C. for 1 hour. 10 µl of this solution was mixed with 1µl of 6×DNA Loading Dye and loaded onto a 1.5% agarose gel. The gels were viewed using Bio-Rad Gel Doc.

Figure 18:
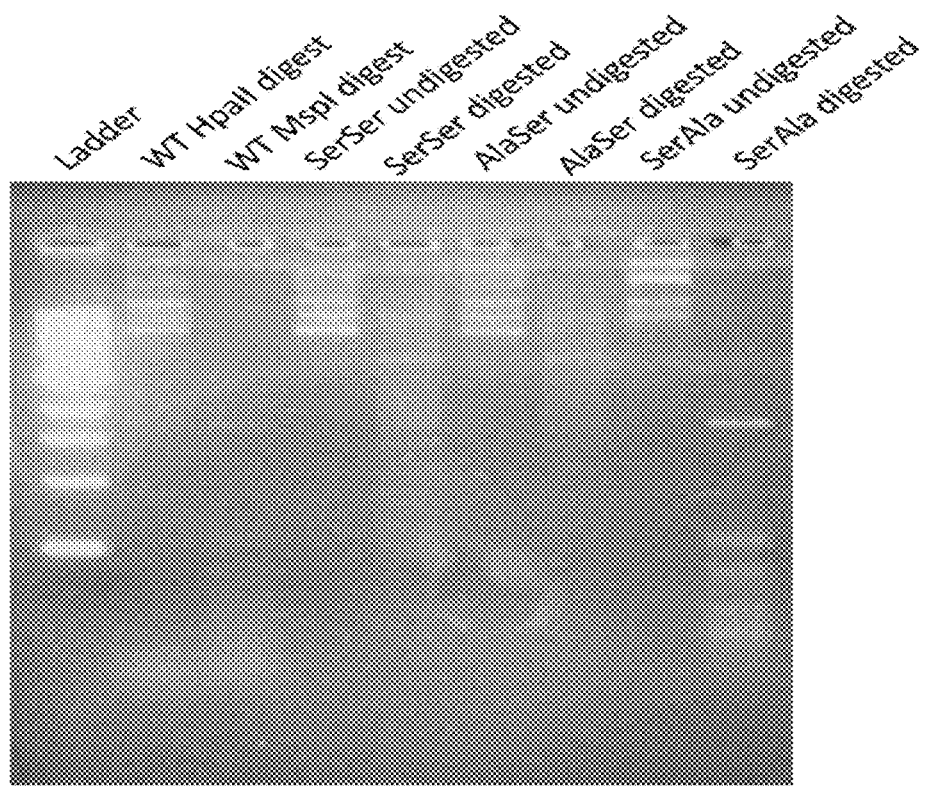
FIG. 18. Gel picture of wild type (WT) and mutant pCa17 digested with HpaII for 1 hour. Digestion of wildtype plasmid with methylation insensitive MspI serves as a positive control for digestion. The gel results of the in vivo functional assay of the mutant variants of M.SssI. The gel result with the isolated plasmid digested with HpaII indicated that the wildtype was completely resistant to HpaII digestion as expected, SerSer and AlaSer mutant plasmids were partially resistant to HpaII digestion, whereas the SerAla mutant was completely digested by HpaII. The result confirms that the SerSer and AlaSer mutants are capable of methyl transfer, however, at an expectedly lower efficiency than the wild type due to its larger active site.

The results of the in-vivo functional assay with the mutant variants of M.SssI are shown in FIG. 18. The plasmids from the mutants were isolated and digested with HpaII. It was observed that SerSer (SssI Q142S/N370S) and AlaSer (M.SssI Q142A/N370S) mutant plasmids are partially resistant to HpaII digestion whereas the SerAla (M.SssI Q142S/N370A) mutant was completely digested by HpaII.

We hypothesized that the mutant plasmid isolated from the bacteria would be resistant to HpaII digestion if it was expressing a functional methyltransferase. The gel result for the isolated plasmid digested with HpaII (see FIG. 18) indicated that the wild-type was completely resistant to HpaII digestion as expected, SerSer and AlaSer mutant plasmids were partially resistant to HpaII digestion, whereas the SerAla mutant was completely digested by HpaII. The result confirms that the SerSer and AlaSer mutants are capable of methyl transfer, however at an expectedly lower efficiency than the wild-type due to its larger active site.

Future efforts will focus on the completion of mutagenesis and the purification of the His-tagged wild type and additional mutant M.SssI proteins. Subsequently the proteins will be further tested for their methyltransferease activity. Simultaneously, synthetic AdoMet will be screened and optimized for high efficiency of both enzymatic transfer and photo-conversion using plasmid DNA, and finally experiments will be performed, using the optimal AdoMet derivative, to determine methylation patterns in real world genomic DNA preparations, specifically those which have large amounts of methylation data (for example, DNA from the mammary carcinoma cell line MCF-7). Subsequent high throughput next generation sequencing will facilitate DNA methylation status to be read out at single base pair resolution and validate the accuracy of our method.

Depending on the successes of these experiments this new method for methylome analysis of DNA could be effectively and economically used at the single cell level. Whole-genome sequencing from single cells is recognized as the essential next step in genome biology and anticipated to be useful in many clinical applications; this method thus allows whole genome methylation profiling that involves only slight modifications of the DNA sequencing protocol to be done in parallel.

Figure 19:
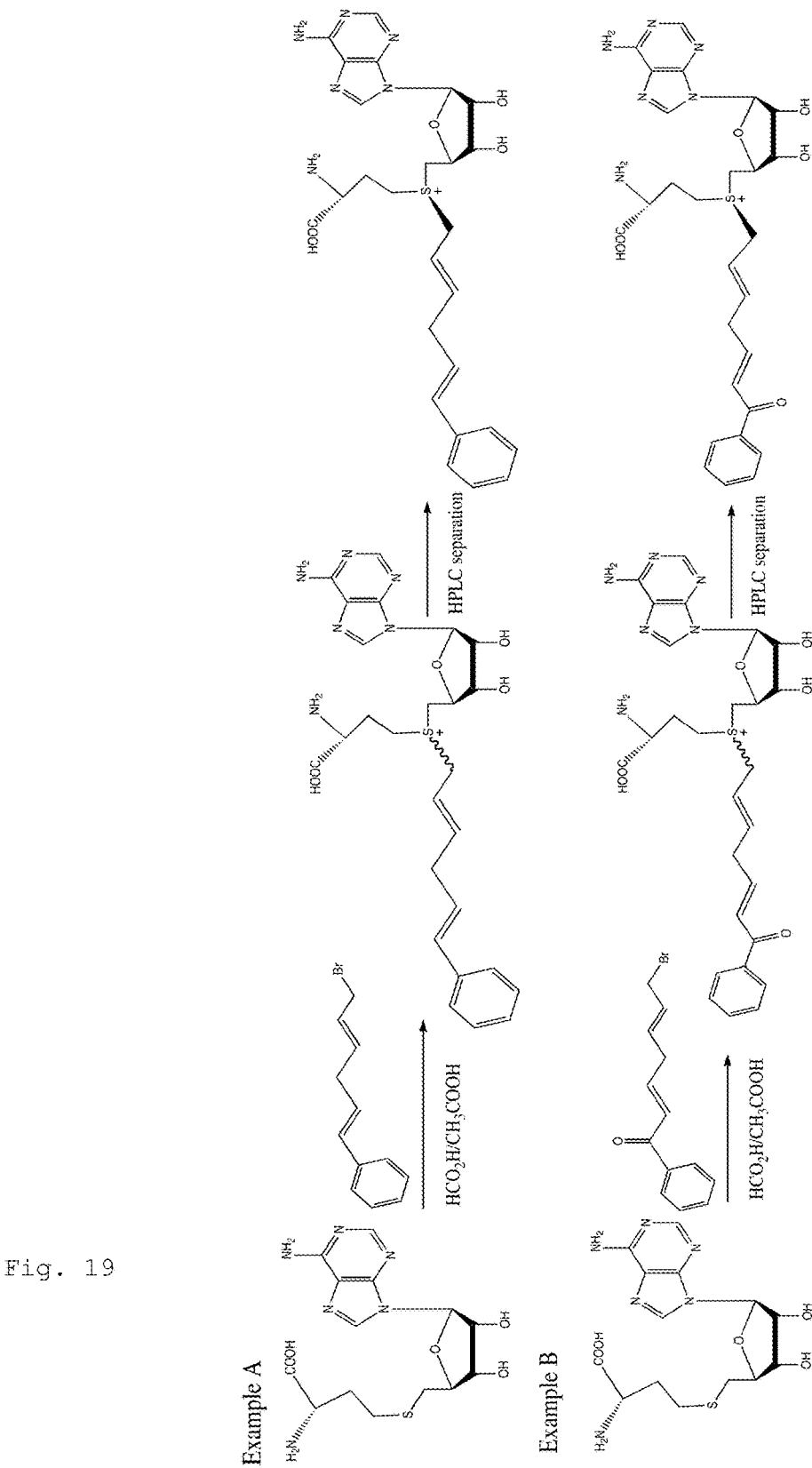
FIG. 19. Example scheme for the syntheses of AdoMet analogs containing photoreactive groups with long-wavelength absorption.

Example 12: Syntheses of AdoMet Analogs Containing the Desired Long-Wavelength Absorbing Photo-Reactive Moieties Synthesis of AdoMet analogs with the desired long-wavelength absorbing photo-reactive moieties is carried out by regioselective S-alkylation of AdoHcy with corresponding triflates or bromides of the photoreactive moieties under mild acidic conditions. A diastereomeric mixture of sulfonium is expected after alkylation of AdoHcy, and further RP-HPLC (reverse phase high performance liquid chromatography) purification is conducted to isolate the enzymatically active S-epimer for the subsequent transfer reaction. Examples of the synthesis route for AdoMet analog are shown in FIG. 19. Triflates or bromides of the photoreactive moieties needed for such AdoMet analog synthesis can be prepared using commercially available starting materials.

The AdoMet derivatives contain sulfonium-linked photoactive groups that are much bulkier than the methyl group carried by AdoMet. We therefore introduced amino acid substitutions that replaced bulky Glutamine (Q) 142 and Asparagine (N) 370 with either Alanine or Serine in order to enlarge the AdoMet binding pocket of M.SssI (see Example 11). The efficiency of transfer of bulky photoactive groups from AdoMet derivatives will be increased by this modification. We have derived the following mutants of M.SssI: 0142S, N370S; Q142S N370A; Q142A, N370S; 0142O, N370S; Q142Q, N370A; Q142S, N370N; Q142A, N370N. Each enzyme has been purified and will be tested for efficiency in transfer of bulky photoactive groups from AdoMet derivatives to unmethylated CpG dinucleotides in DNA.

Example 13: Further Testing of Photo-Conversion Reaction

An alternative method to test the conversion of a C with its 5 position modified with a photoactive group within a synthetic single stranded DNA molecule to a U analog utilizes a synthetic double-stranded DNA molecule, which takes advantage of a simple gel-based restriction endonuclease assay.

Both strands of a DNA molecule of at least 50 base pairs are synthesized as oligonucleotides containing one modified C in a CpG context. The C within the same CpG moiety in both strands is replaced with one of the 5 position modified photo-convertible analogs described earlier using standard phosphoramidite-based synthetic chemistry. The oligonucleotides are designed in such a way that, after PCR, the resulting double-stranded DNA molecule will be cleaved with one restriction enzyme in the absence of photo-conversion and a different restriction enzyme in the presence of photo-conversion. Confirmation of the photo-conversion event is via detection of the resulting restriction fragments on agarose gels, or following denaturation, the single strand fragments via MALDI-TOF mass spectrometry. Additional restriction sites allow for ease of discrimination of fragments on gels, while additional modifiable CpG sites elsewhere in the length of the synthetic DNA molecule provide further options for testing photo-conversion of multiple C analogs at various short distances from each other. An example of such an assay is shown (FIG. 20).

Figure 21:
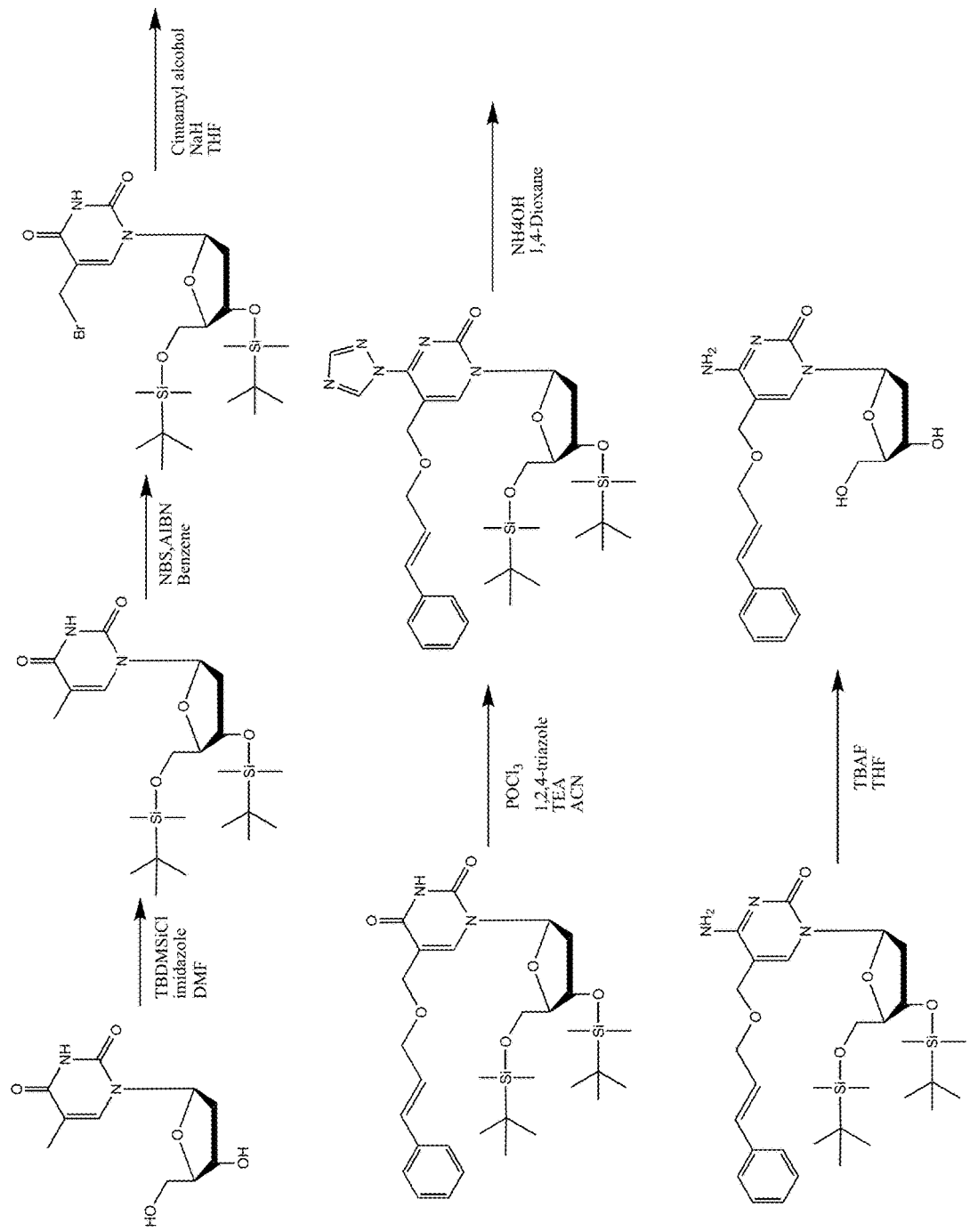
FIG. 21. Example of the synthesis route for 5-PhAllOMC.
Figure 22:
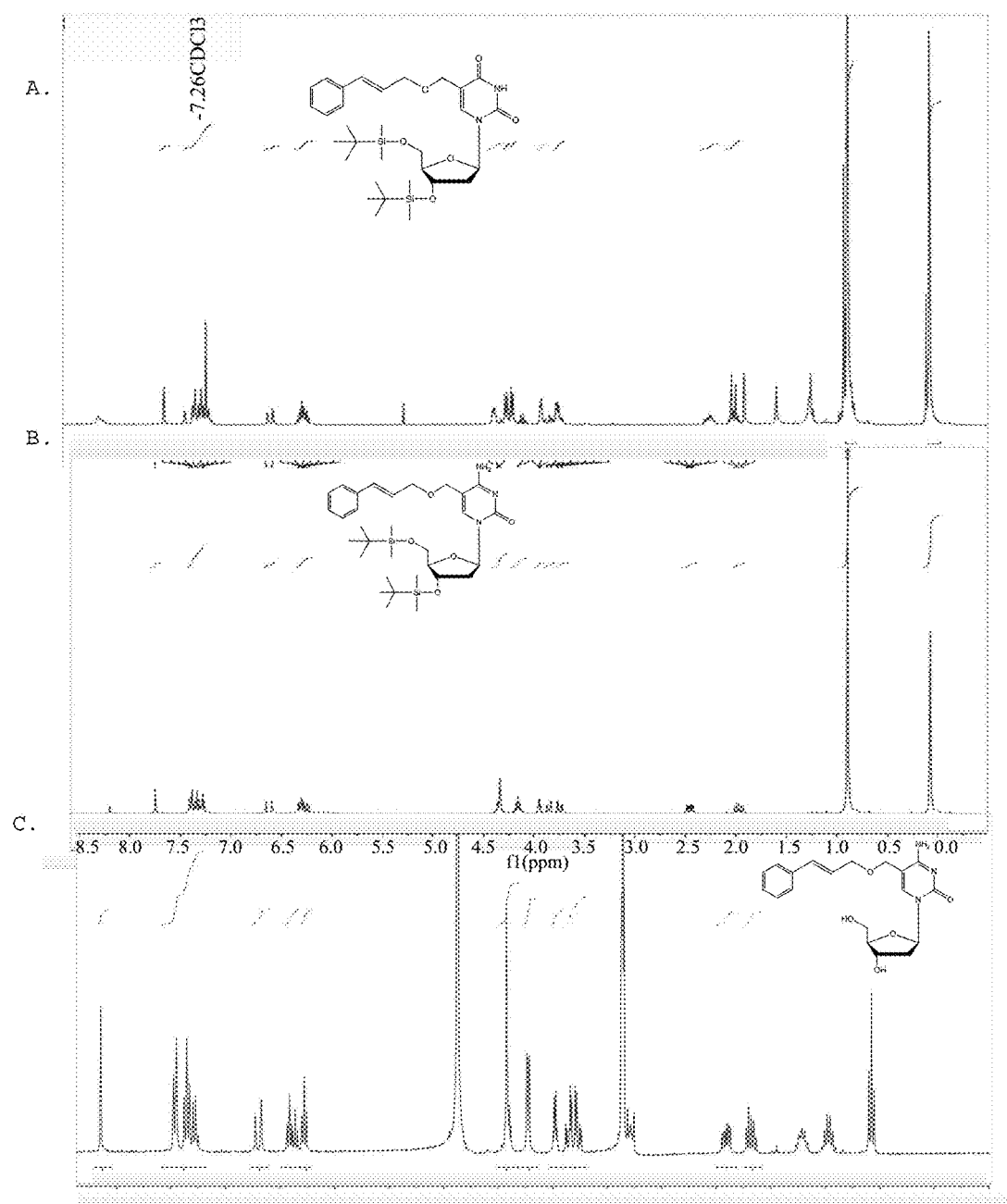
FIG. 22. A. Nuclear magnetic resonance (NMR) spectrum for compound 4 of FIG. 24. B. Nuclear magnetic resonance (NMR) spectrum for compound 6 of FIG. 24. C. Nuclear magnetic resonance (NMR) spectrum for compound 7 of FIG. 24.
Figure 23:
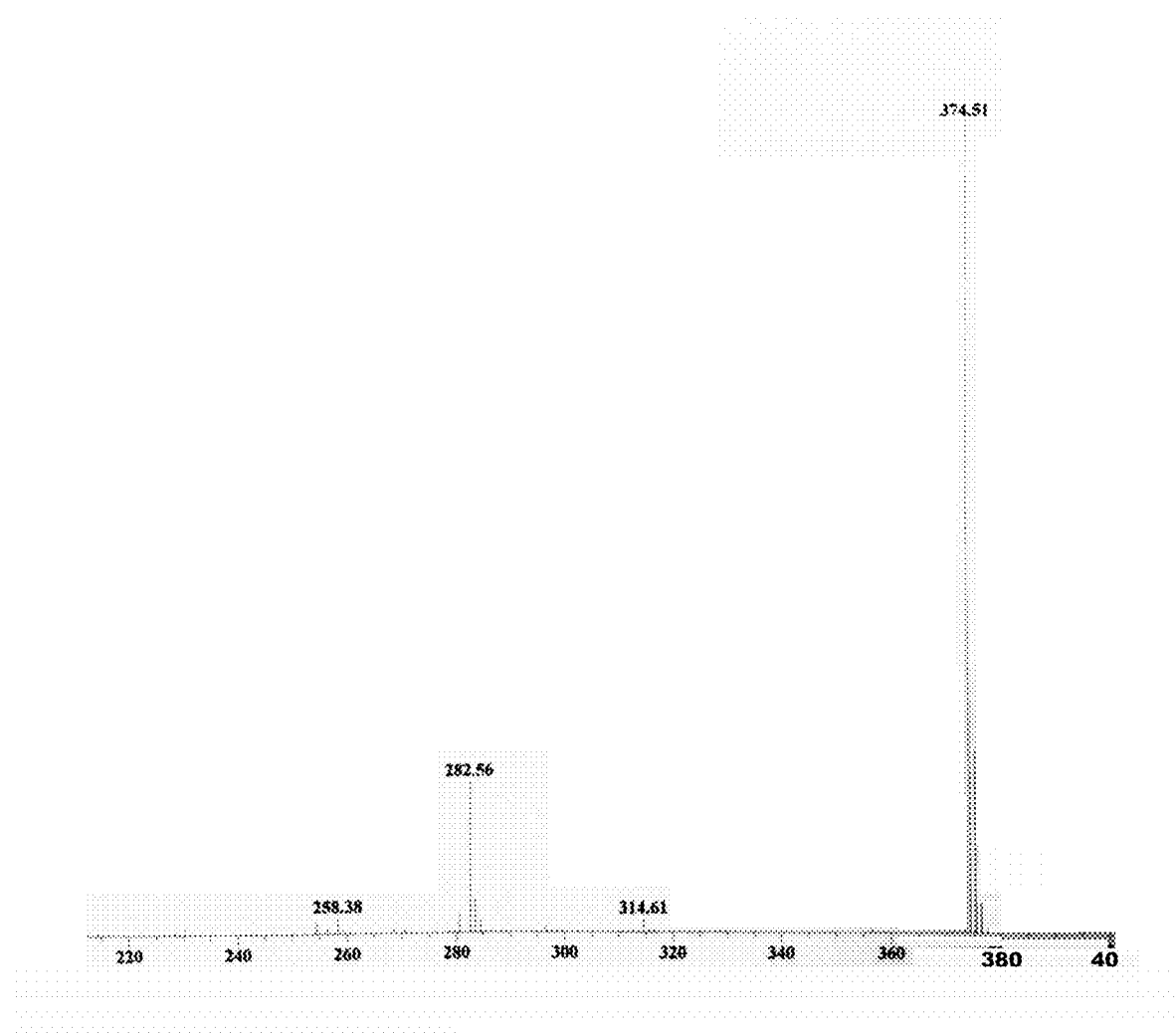
FIG. 23. Mass spectrum of 5-PhAll-OMC.
Figure 24:
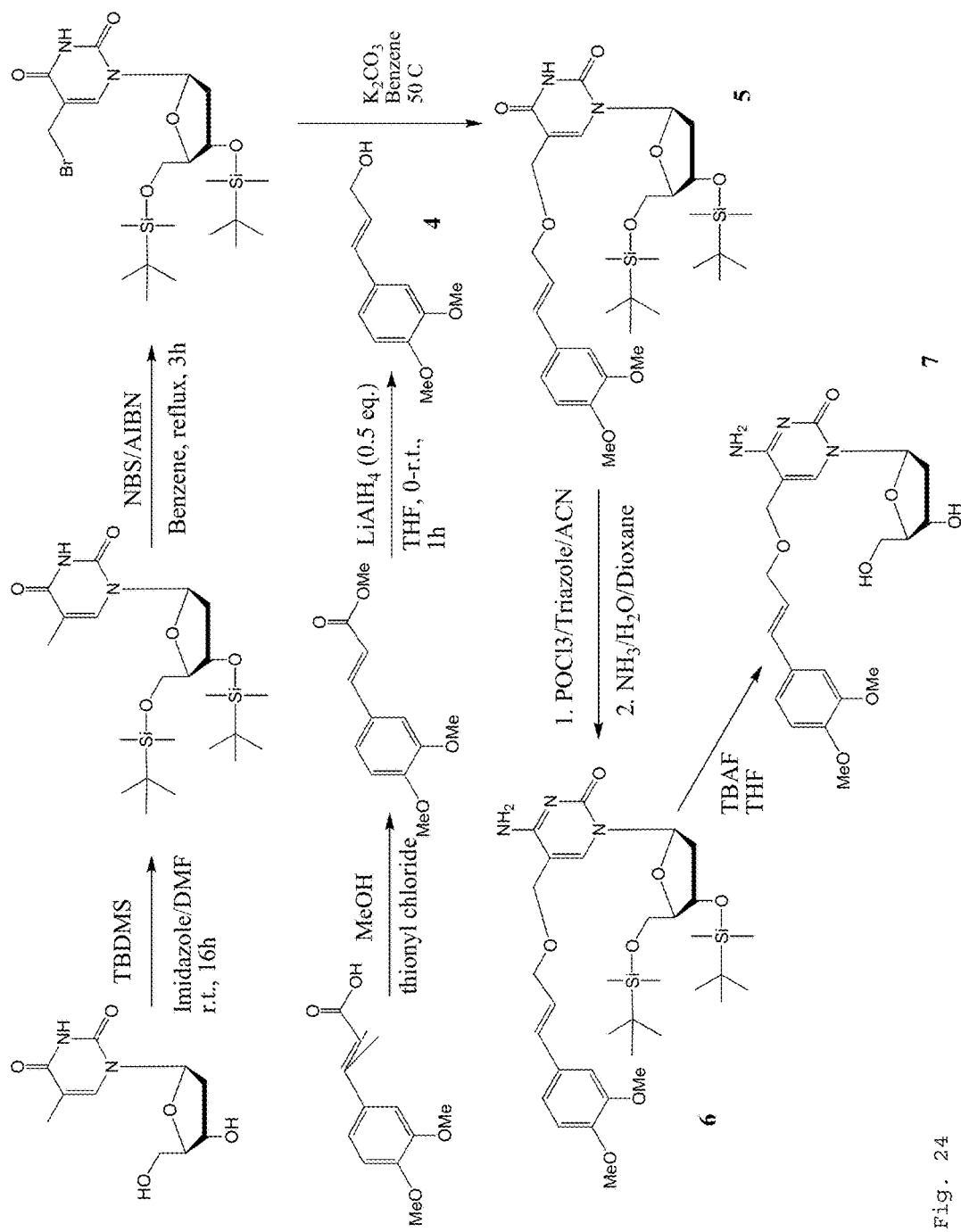
FIG. 24. Example synthesis route for 5-DiMePhAll-OMC.

Example 14: Synthesis of Model Compounds for Use in Testing of Photo-Conversion Reaction Because of the likely damaging effects of UVB radiation (300 nm) used to convert the 5-All-OMC to the 5-All-OMU analogue, a phenylallyl derivative of cytidine (5-PhAll-OMC) so that a longer, DNA-benign wavelength could be used to trigger C to U conversion was synthesized instead. Specifically, both model compounds 5-PhAllOMC and 5-DiMePhAll-OMC have been synthesized. An example of the synthesis route for 5-PhAll-OMC is shown in FIG. 21. Nuclear magnetic resonance (NMR) spectra for compounds 4, 6 and 7 of FIG. 20 are respectively shown in FIGS. 22 A, B and C. A mass spectrum of 5-PhAll-OMC is shown in FIG. 23. An example of the synthesis route for 5-DiMePhAll-OMC is shown in FIG. 24.

Figure 25:
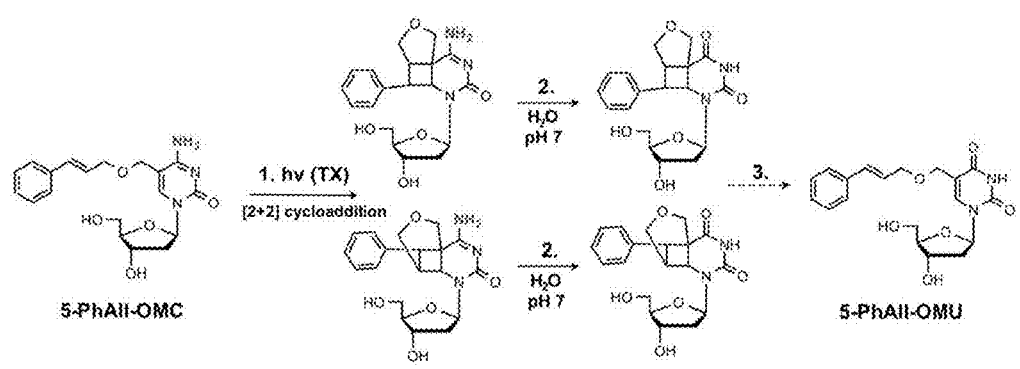
FIG. 25. Photochemical conversion of 5-PhAll-OMC to 5-PhAll-OMU. (1.) Direct photolysis or triplet sensitization initiates a [2+2] cycloaddition. (2.) The primary amine group of C is oxidized to a carbonyl group. This reaction occurs spontaneously in aqueous solution (pH=7) due to the loss of the double bond in C. (3.) In the final step cycloreversion can generate 5-PhAll-OMU. A cycloreversion of a similar dT derivative has been reported in the literature (Matsumura, et al., 2008, Fujimoto, et al., 2010).

5-PhAll-OMC was irradiated with 350 nm light in the presence of the triplet photosensitizer thioxanthone (TX). The detailed mechanism of the transformation of 5-PhAll-OMC to a U analogue is shown in FIG. 25. The majority of the starting material was converted to a cyclobutyl derivative with oxidative deamination at the 4 position, as confirmed by mass spectrometry, infrared spectroscopy, and $^1$H and $^{13}$C NMR.

Figure 26:
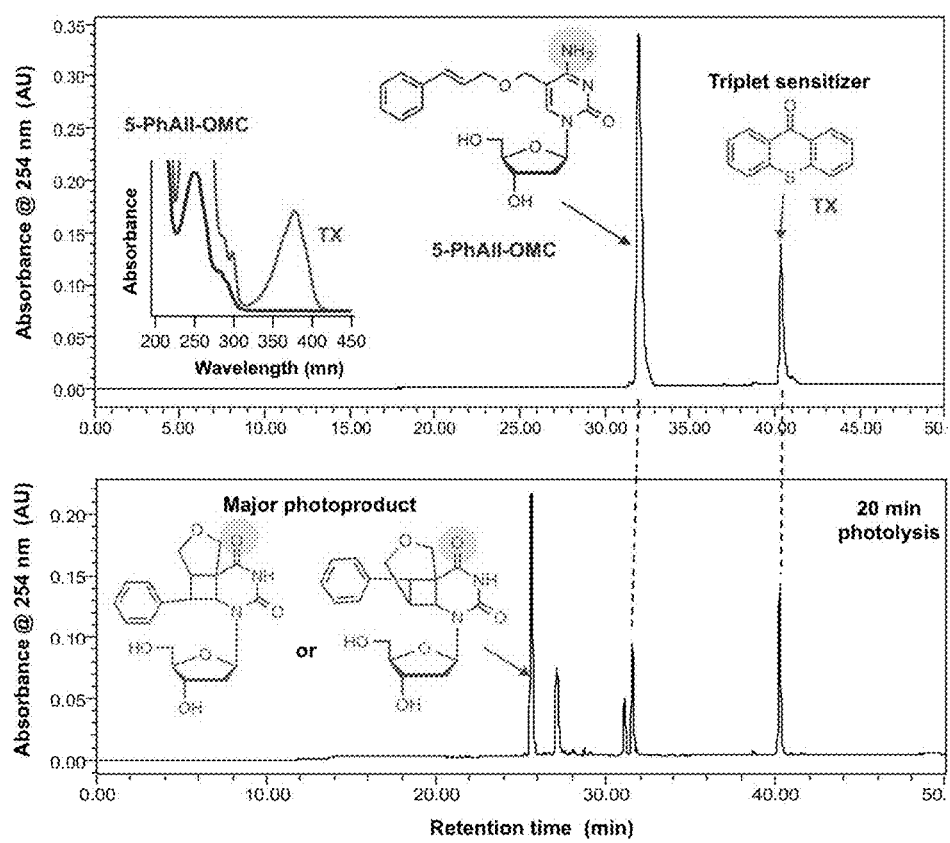
FIG. 26. Top, HPLC analysis of 5-PhAll-OMC (shown in the top graph at top center) in the presence of the triplet sensitizer thioxanthone (TX; shown in the top graph at top right) before photoirradiation. The inset shows the UV absorption spectra of TX and 5-PhAll-OMC; note that 350 nm light does not interact with cytosine but is strongly absorbed by TX. Bottom: analysis after 20 min photoirradiation with 350 nm light. While the concentration of the sensitizer (TX) remained unchanged, 5-PhAll-OMC was mostly consumed and new photoproducts appeared. The major photoproduct was isolated and identified by MS, $^1$H-NMR and $^{13}$C-NMR as a cyclobutyl derivative of U, either a straight or cross adduct (as shown in the bottom graph on left side).
Figure 27:
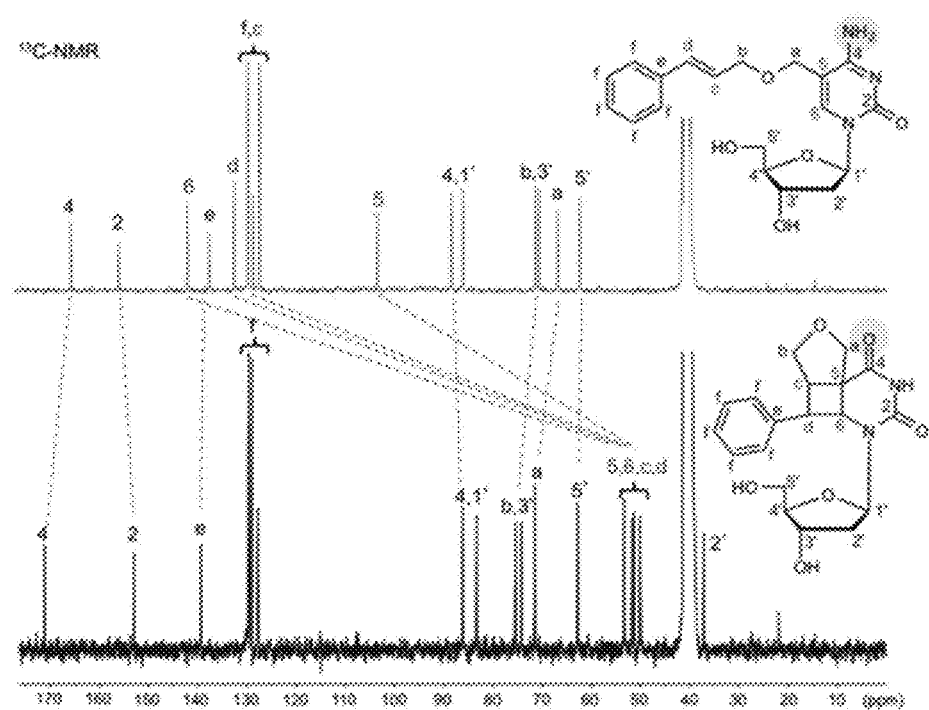
FIG. 27. $^{13}$C-NMR analysis of 5-PhAllOMC (top) and isolated photoproduct (bottom). Major shifts were observed for carbon atoms 5, 6, c, and d. For simplicity, only the straight [2+2] cylooadduct is shown. These results, like those of infrared spectroscopy, show oxidative deamination of the 4 position without effect on base pairing positions.

The new product was found 1 mass unit higher than the starting material 5-PhAll-OMC, indicating possible U analog was generated from 5-PhAll-OMC. FIG. 26 shows HPLC analysis of 5-PhAll-OMC in the presence of the triplet sensitizer thioxanthone (TX) before photoirradiation. The inset shows the UV absorption spectra of TX and 5-PhAll-OMC; note that 350 nm light does not interact with cytosine but is strongly absorbed by TX. FIG. 26 at the bottom shows an analysis after 20 min photoirradiation with 350 nm light. While the concentration of the sensitizer (TX) remained unchanged, 5-PhAll-OMC was mostly consumed and new photoproducts appeared. The $^{13}$C NMR spectra, shown in FIG. 27, unambiguously confirm the formation of a [2+2] cycloadduct in either straight or cross configuration.

Figure 28:
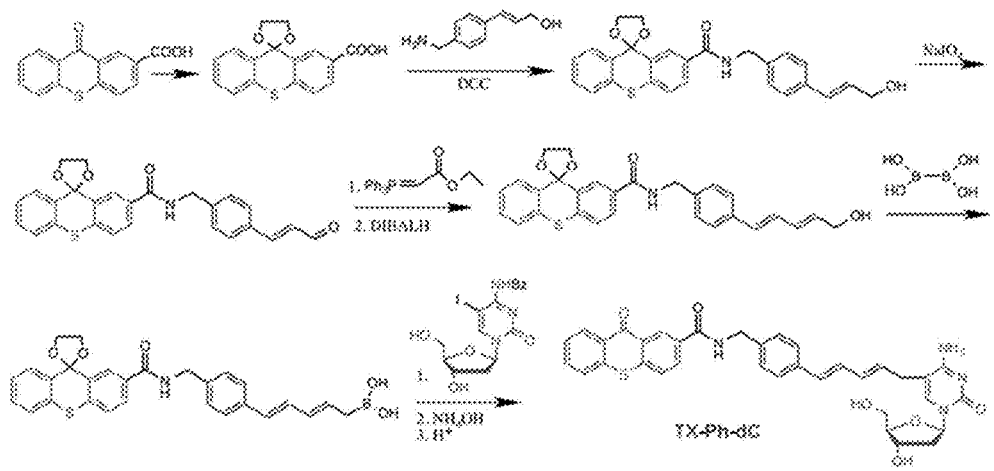
FIG. 28. Synthesis of photo-sensitizer conjugated model compound (TX-Ph-C). Incorporation of the TX photosensitizer into the photoactive group will increase specificity and efficiency of the deamination reaction.

Example 15: Synthesis of Model Compounds in which Photo-Sensitizer (TX) is Covalently Attached to the Photoreactive Functionality for Use in Testing of Photo-Conversion Reaction To increase efficiency and to reduce the likelihood of unexpected side reactions, the TX sensitizer is to be covalently linked to the phenyl chromophore. Intramolecular triplet energy transfer will deactivate the TX triplet state within a few nanoseconds to induce triplet excited moieties in the this phenylalkenyl chromophore (FIG. 28), which then react with the double bond of C via [242] cycloaddition (Turro, et al., 2010). Because of the orders of magnitude reduction in TX triplet lifetime from microseconds to nanoseconds (due to intramolecular energy transfer) undesired side reactions, such as electron transfer reactions, which damage DNA, are highly unlikely. FIG. 28 shows one of the synthetic routes for a model compound which has photosensitizer (TX) covalently attached.

Example 16: Synthesis of Photo-Sensitizer Containing AdoMet Analogues

Figure 29:
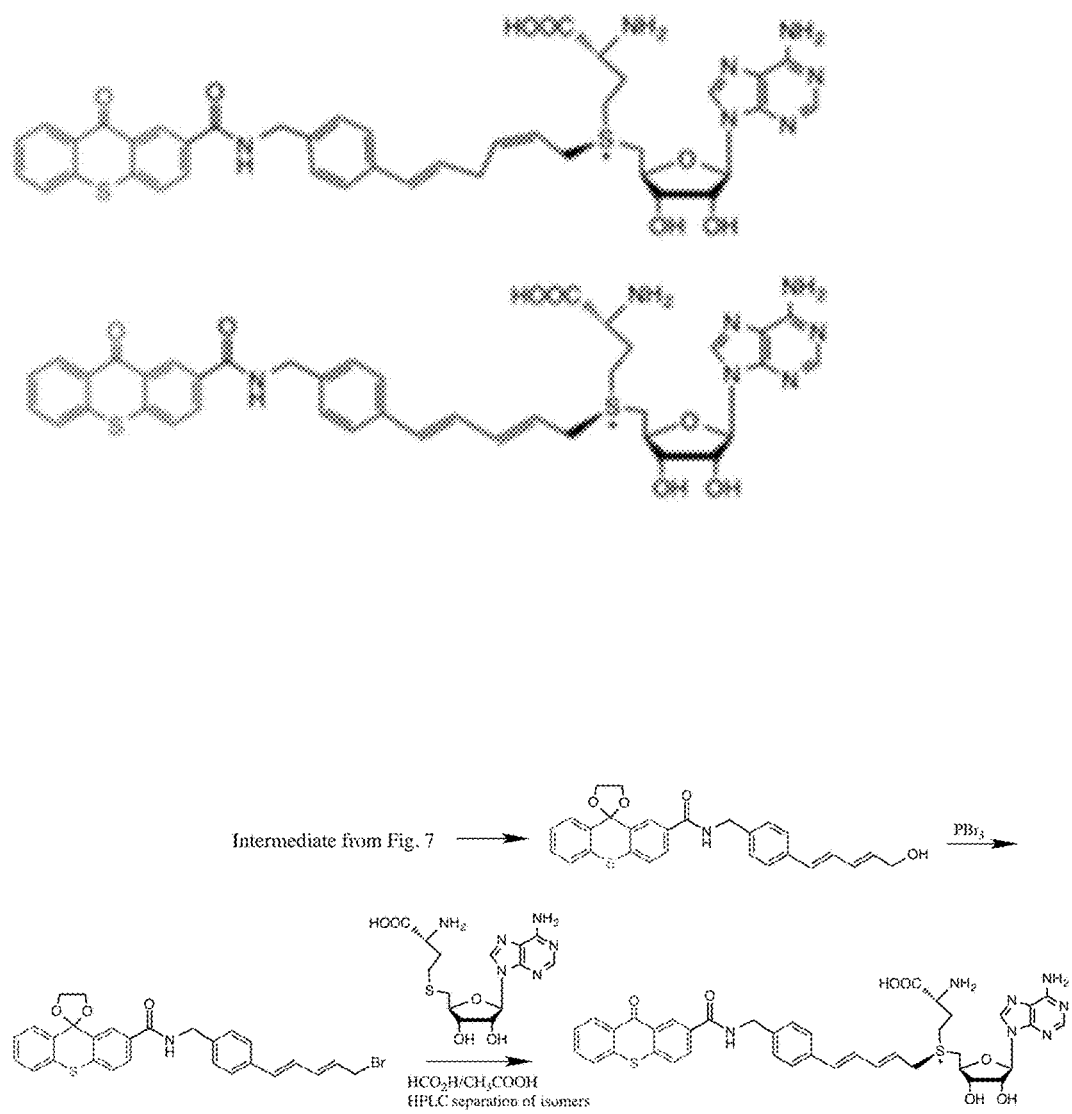
FIG. 29 Top: Sensitizer-containing AdoMet analogues that will deliver a highly efficient photoactive deaminating group to the cytosine of unmethylated CpG sites in double stranded DNA. The thioxanthone photosensitizer is shown. Bottom: Scheme for synthesis of sensitizer-containing AdoMet analogue.

Sensitizer-containing AdoMet analogues will deliver a highly efficient photoactive deaminating group to the cytosine of unmethylated CpG sites in double stranded DNA. The structures and a synthetic scheme for one compound is presented in FIG. 29.

Figure 30:
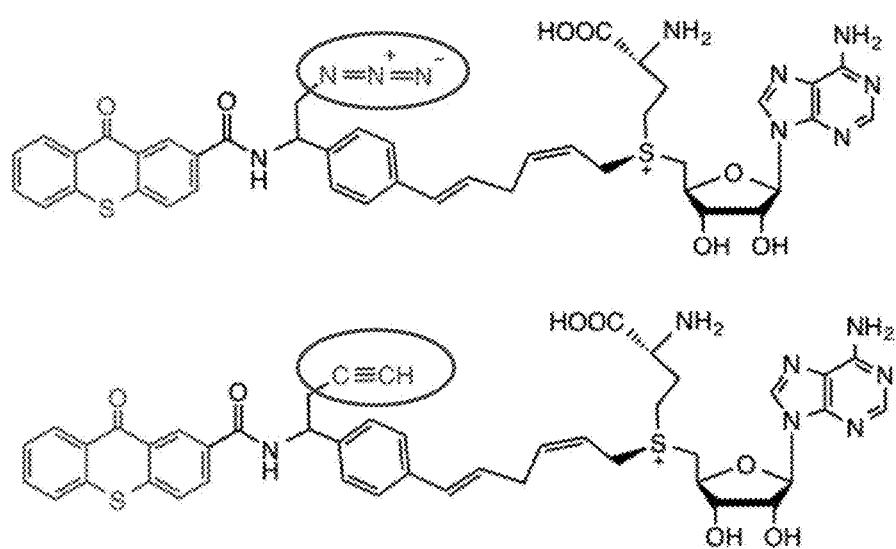
FIG. 30. Example structures of the AdoMet analogue containing both photo-sensitizer (TX) and clickable moieties (azido modification is at top, alkyne at bottom, both are circled in this figure).

Example 17: Synthesis of AdoMet Analogues Containing Both Photo-Sensitizer (TX) and Clickable Moieties for CpG Site Enrichment and Sequencing The CpG dinucleotide is underrepresented by about a 5-fold in human genomic DNA and is concentrated in CpG islands (Bestor et al., 2014) and as a result in short-read next-generation sequencing only about 20% of all DNA sequences contain even a single CpG dinucleotide; this means that 80% of sequencing costs are wasted. It is especially beneficial and essential to detect very small amounts of tumor DNA. This can be done by adding an azido or alkyne moiety to the AdoMet analogue shown in FIG. 30 so that derivatized DNA that contained unmethylated CpG dinucleotides can be captured and purified on alkyne or azido magnetic beads by Click chemistry (Kolb et al., 2001). The result will be a 5-fold increase in throughput. Azido- and alkyne-modified photoactive groups are shown in FIG. 30.

Figure 31:
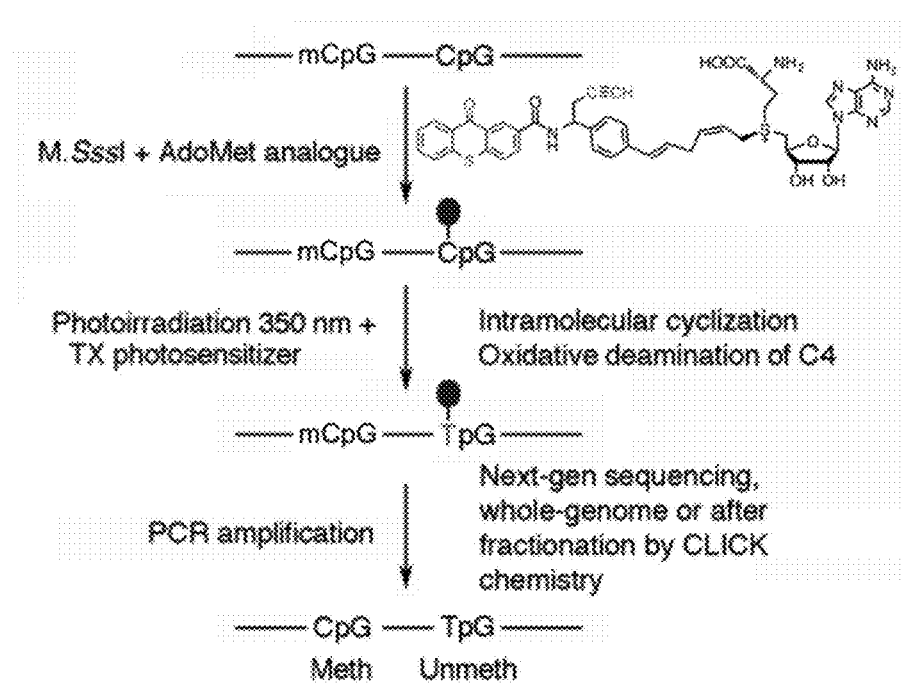
FIG. 31. Summary of the overall scheme of photochemical methylation profiling. Modifications to be introduced in order to purify DNA fragments that contain unmethylated CpG sites by Click chemistry. Those DNA fragments that contain unmethylated CpG dinucleotides will be collected on magnetic beads that contain the complementary modification (alkyne or azido) in the presence of copper ions. The beads will be washed in neutral aqueous buffer, adapters ligated, and DNA amplified by PCR directly off the beads prior to library construction.

Example 18: CpG Site-Enriched Photochemical Methylation Profiling Using AdoMet Analogues Containing Both Photo-Sensitizer (TX) and Clickable Moieties To increase the efficiency of photochemical methylation profiling, those DNA fragments that contain unmethylated CpG dinucleotides will specifically be extracted by means of Click chemistry, as shown in FIG. 31. If the transferred group has an alkyne moiety, magnetic beads decorated with azido groups will be used for the capture; transferred groups with azido moieties will be captured on alkyne-derivatized beads (Kriukiend et al., 2013). Captured DNA will then be processed for Next-Gen DNA sequencing. This will ensure that only those DNA fragments that contain one or more unmethylated CpG sites will be subjected to sequencing. Notice that this method has single-CpG resolution, and all methylated CpG sites will be sequenced as CpG sites and all unmethylated CpG sites as TpG's.

Figure 32:
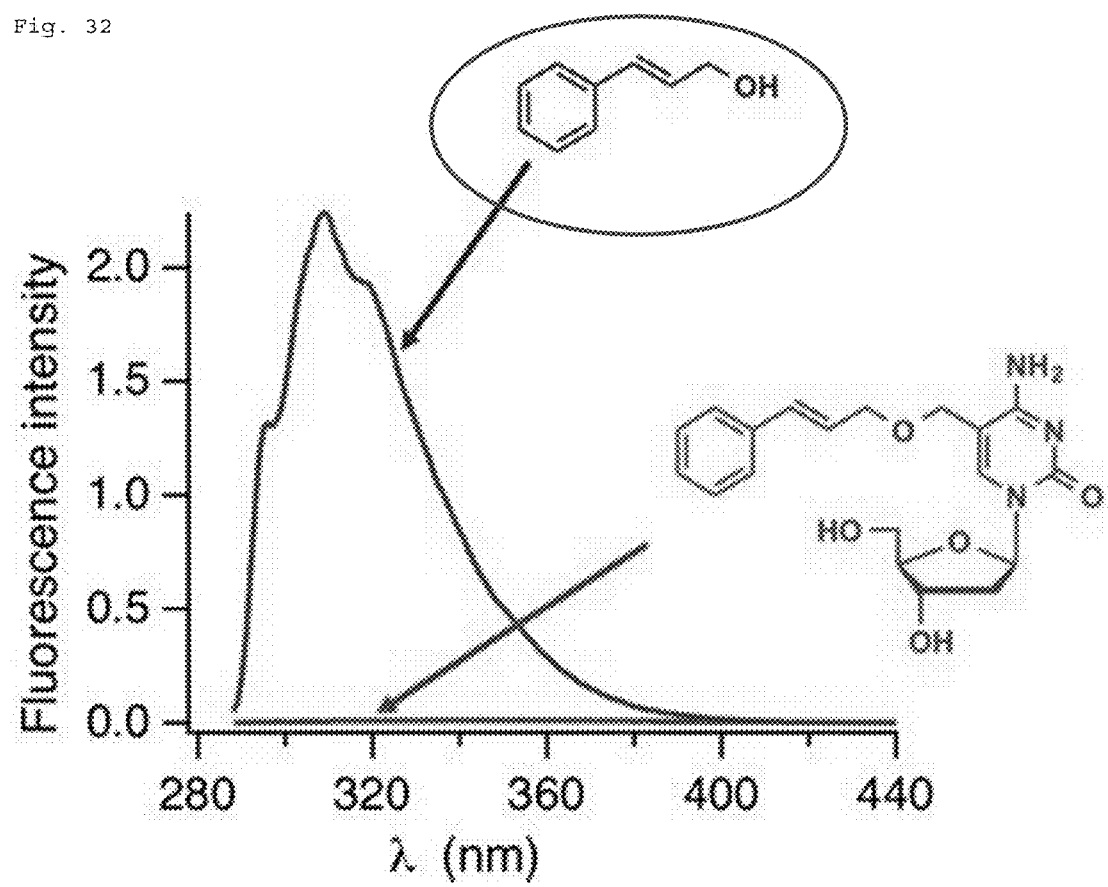
FIG. 32. Fluorescence spectra of compounds cinnamyl alcohol (circled) and the model compound 5-PhAll-OMC of FIG. 21 in acetonitrile (ACN) solution ($\lambda_{ex}$=282 nm). This figure shows that the fluorescence of the cinnamyl ether chromophore (styrene chromophore) is quenched efficiently when covalently linked to C due to singlet state energy transfer to C and/or [2+2] cycloaddition of the cinnamyl double bond to C.

Furthermore, FIG. 32 shows fluorescence spectra of two compounds in acetonitrile solution ($\lambda_{ex}$=282 nm). The loss of fluorescence of the styrene chromophore, when the deoxycytidine moiety is covalently linked to 5-PhAll-OMC of FIG. 21, is caused by fast intramolecular [2+2] cycloaddition (first reaction step leading to U) and/or singlet state energy transfer from the styrene chromophore to the deoxycytidine moiety. Taking advantage of the higher molar absorptivity of the styrene chromophore, energy transfer to the deoxycytidine chromophore can also lead to [2+2] cycloaddition and subsequent conversion to U.

[2+2] cycloadditions are known to proceed often more efficiently from triplet excited states than from singlet excited states. We showed by laser flash photolysis and transient absorption spectroscopy, that triplet excited states of the styrene chromophore in 5-PhAll-OMC of FIG. 21 can be efficiently populated by triplet sensitization using thioxanthone.

Thioxanthone derivatives have excellent light absorption properties in the near UV spectral region until 400 nm, a spectral region which is not harmful to DNA. To determine the rate constant of triplet energy transfer by laser flash photolysis, the model compound 5-PhAll-OMC of FIG. 21 was used which contains the styrene chromophore.

Photoexcitation of thioxanthone generated triplet states which were quenched by the styrene chromophore (5-PhAll-OMC of FIG. 21) with a rate constant of $7.8 \times 10^9$, $M^{-1}s^{-1}$ which is the maximum rate constant possible for triplet energy transfer (FIG. 33).

FIG. 34 shows decay traces of the transient absorbance of thioxanthone triplet monitored at 625 nm after pulsed laser excitation (355 nm, 5 ns pulse width) in argon saturated acetonitrile solutions in the absence and presence of various concentrations of 5-PhAll-OMC of FIG. 21 (0 to 0.25 mM) (FIG. 34 A) and the determination of the triplet energy transfer rate constant (FIG. 34 B).

REFERENCES

Bergstrom D E, Inoue H and Reddy P A (1982) Pyrido (2,3-d) pyrimidine nucleosides. Synthesis via cyclization of C-5-substituted cytidine. *Journal of Organic Chemistry* 47(11), 2174-2178.

Church G M, Gilbert W. (1984) Genomic sequencing. Proc Natl Acad Sci USA. 81, 1991-1995.

Clark S J, Harrison J, Paul C L, Frommer M. (1994) High sensitivity mapping of methylated cytosines. Nucleic Acids Res. 22, 2990-2999.

Dalhoff C, G Lukinavicius, S Klimasauskas and E Weinhold (2006a) Direct transfer of extended groups from synthetic cofactors by DNA methyltransferases *Nat Chem Biol* 2:31-2.

Dalhoff C, G Lukinavicius, S Klimasauskas and E Weinhold (2006b) Synthesis of S-adenosyl-L-methionine analogs and their use for sequence-specific transalkylation of DNA by methyltransferases *Nat Protoc* 1, 1879-86.

Du J, Yoon T P, (2009) Crossed Intermolecular [2+2] Cycloadditions of Acyclic Enones via Visible Light Photocatalysis *J. Am. Chem. Soc.* 131 (41), pp 14604-14605.

Eads C A, Laird P W. (2002) Combined bisulfite restriction analysis (COBRA). Methods Mol Biol 200, 71-85.

Edwards J R, O'Donnell A H, Rollins R A, Peckham H E, Lee C, Milekic M H, Chanrion B, Fu Y, Su T, Hibshoosh H, Gingrich J A, Haghighi F, Nutter R, Bestor T H (2010) Chromatin and sequence features that define the fine and gross structure of genomic methylation patterns. Genome Res. 20, 972-980.

Fujimoto K, Konishi-Hiratsuka K, Sakamoto T, Yoshimura Y (2010) Site-specific cytosine to uracil transition by using reversible DNA photo-crosslinking. ChemBioChem 11(12), 1661-1664.

Gitan R, Shi H, Chen C, Yan P, Huang T (2002) Methylation-Specific Oligonucleotide Microarray: A New Potential for High-Throughput Methylation Analysis *Genome Res.* 12, 158-164.

Goll M, Bestor Timothy (2005) Eukaryotic Cytosine Methyltransferases. Annual Review of Biochemistry Vol. 74: 481-514

Haga N, Ogura H (1993) Photocycloaddition of cytosine and 2'-deoxycytidines to 2,3-dimethyl-2-butene *Heterocycles* 36(8), 1721-1724.

Ischay M A, Anzovino M E, Du J, Yoon T P (2008) Efficient Visible Light Photocatalysis of [2+2] Enone Cycloadditions *J. Am. Chem. Soc.*, 130 (39), pp 12886-12887.

Ischay M A, Lu Z, Yoon T P (2010) [2+2] Cycloadditions by Oxidative Visible Light Photocatalysis *J. Am. Chem. Soc.* 132 (25), pp 8572-8574.

Kriukiené E, Labrie V, Khare T, Urbanavičiūtė G, Lapinaitė A, Koncevičius K, Li D, Wang T, Pai S, Ptak C, Gordevičius J, Wang S C, Petronis A, Klimašauskas S (2013) DNA unmethylome profiling by covalent capture of CpG sites. Nature Communications, 4, 2190.

Laird P W (2010) Principles and challenges of genome-wide DNA methylation analysis. Nature Reviews Genetics 11, 191-203.

Lin Q and Lim R. V (2011) Photoinducible bioorthogonal chemistry: a spatiotemporally controllable tool to visualize and perturb proteins in live cells, *Acc. Chem. Res.,* 44 (9), 828-839.

Lukinavicius G, Lapinaite A, Urbanaviciute G, Gerasimaite R, Klimasauskas S (2012) Engineering the DNA cytosine-5 methyltransferase reaction for sequence-specific labeling of DNA Nucleic Acids Res, 40(22), 11594-602.

Matsumura T, Ogino M, Nagayoshi K, Fujimoto K (2008) Photochemical site-specific mutation of 5-methylcytosine to thymine *Chemistry Letters* 37, 94-95.

Naismith J, Liu H (2008) An efficient one-step site-directed deletion, insertion, single and multiple-site plasmid mutagenesis protocol *BMC Biotechnology* 8:91.

Renbaum, P., Abrahamove, D., Fainsod, A., Wilson, G. G., Rot-tern, S. and Razin, A. (1990) Nucleic Acids Res. 18, 1145-1152.

Robertson K D (2005) DNA methylation and human disease Nature Reviews Genetics 6, 597-610.

Rollins R, Haghighi F, Edwards J, Das R, Zhang M, Ju J, and Bestor T H (2006) Large-scale structure of genomic methylation patterns Genome Res. 16, 157-163.

Sambrook J, Fritsch E F, Maniatis T. (1989). Molecular Cloning; a laboratory manual. 2nd edition. Cold Spring Harbor, N.Y.: Cold Spring Harbor Laboratory Press.

Steigerwald S D, Pfeifer G P, Riggs A D. (1990) Ligation-mediated PCR improves the sensitivity of methylation analysis by restriction enzymes and detection of specific DNA strand breaks. Nucleic Acids Res. 18, 1435-1439.

Suzuki M M, Bird A (2008) DNA methylation landscapes: provocative insights from epigenomics. Nature Reviews Genetics 9, 465-476.

Trinh B N, Long T I, Laird P W. (2001) DNA methylation analysis by MethyLight technology. Methods 25, 456-462.

Turro N J, Ramamurthy V, Scaiano J C. Modern Molecular Photochemistry of Organic Molecules; University Science Books: Sausalito, Calif., 2010.

Waalwijk C, Flavell R A. (1978) DNA methylation at a CCGG sequence in the large intron of the rabbit beta-globin gene: tissue-specific variations. Nucleic Acids Res 5, 4631-4634.

Warnecke P M, Stirzaker C, Song J, Grunau C, Melki J R, Clark S J. (2002) Identification and resolution of artifacts in bisulfite sequencing. Methods. 27, 101-107.

Warnecke P M, Stirzaker C, Melki J R, Millar D S, Paul C L, Clark S J. (1997) Detection and measurement of PCR bias in quantitative methylation analysis of bisulphite-treated DNA. Nucleic Acids Res. 25, 4422-426.

What is claimed is:
1. A method of determining whether a cytosine present at a predefined position within a single strand of a double-stranded DNA of known sequence is non-methylated comprising:
a) contacting the double-stranded DNA with a CpG methyltransferase and an S-adenosylmethionine analog having the structure:

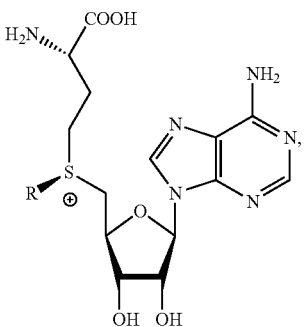

wherein R (1) is a chemical group capable of (i) being transferred from the S-adenosylmethionine analog by the CpG methyltransferase to the 5 carbon of each non-methylated cytosine within the double-stranded DNA and (ii) forming a covalent bond between the chemical group and the 5 carbon of each such non-methylated cytosine within the double-stranded DNA, thereby producing a derivative of the double stranded DNA and (2) has one of the following structures:

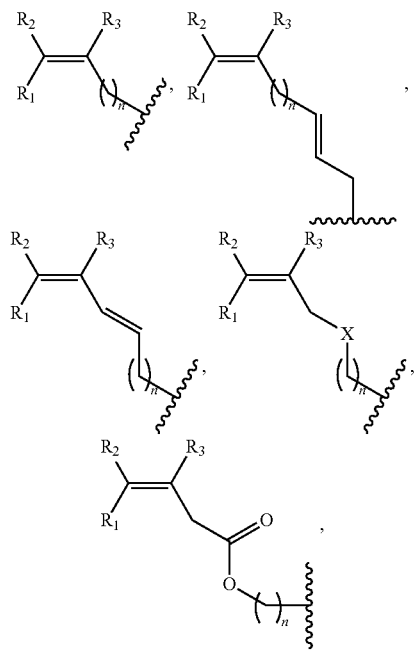

wherein each of $R_1$, $R_2$ and $R_3$ is independently H, alkyl, aryl, $C(O)NH_2$, $C(O)R'$, CN, $NO_2$, or $S(O)_2NHR'$;
wherein X is O or NR';
wherein R' is H, alkyl or aryl; and
wherein n is an integer from 1 to 8;
b) photoirradiating the derivative of the double-stranded DNA at a wavelength greater than 330 nm up to 700 nm so as to photocatalytically convert each cytosine to which the chemical group R is covalently bound to a uracil analog;
c) separately obtaining the single strand from the photoirradiated derivative of the double-stranded DNA;
d) determining the sequence of the single strand ee obtained in step c); and
e) comparing the sequence of the single strand determined in step d) to the sequence of the single strand of the double-stranded DNA prior to performing steps a-d,
wherein the presence of a uracil analog at the predefined position within the single strand of the photoirradiated derivative of the double-stranded DNA indicates that the cytosine at that position in the single strand of the double stranded DNA of known sequence is non-methylated.

2. The method of claim 1, wherein the chemical group R has any one of the following structures:

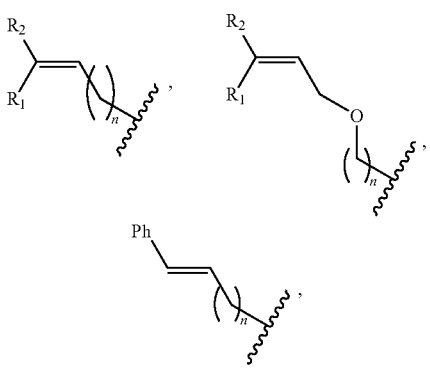

wherein one of $R_1$ and $R_2$ is aryl and the other is H, alkyl, aryl, $C(O)NH_2$, $C(O)R'$, CN, $NO_2$, $S(O)_2NHR'$;
wherein R' is H, alkyl or aryl; and
wherein n is an integer from 1 to 8.

3. The method of claim 1, wherein the CpG methyltransferase is M.SssI methyltransferase or a mutant thereof having methyltransferase activity, M.HhaI methyltransferase or a mutant thereof having methyltransferase activity, or M.CviJI methyltransferase or a mutant thereof having methyltransferase activity.

4. The method of claim 1, wherein the cytosine at the predetermined position in the single strand of the double-stranded DNA is present in a CpG site.

5. The method of claim 1, wherein in step d) the determination of the sequence is obtained by sequencing by synthesis.

6. The method of claim 1, further comprising attaching the single strand from the photoirradiated derivative of the double-stranded DNA to a solid support after step c) and prior to step d).

7. The method of claim 1, wherein the CpG methyltransferase is the mutant M.SssI methyltransferase comprising relative to non-mutant M.SssI methyltransferase from E. coli K12 strain ER1821 (i) substitution of serine for the amino acid Q142 and (ii) substitution of serine for the amino acid N370.

8. The method of claim 1, wherein the photoirradiation in step b) is carried out in the presence of a catalyst having long wavelength absorption properties.

9. The method of claim 8, wherein the catalyst is thioxanthone (TX) or a derivative thereof having catalytic properties.

10. The method of claim 1, wherein the photoirradiation in step b) is carried out at a temperature between 0° C. and 90° C.

11. The method of claim 1, wherein the photoirradiation in step b) is carried out in a buffered solution with pH between 4 and 10.

12. The method of claim 8, wherein the catalyst is covalently linked to the S-adenosylmethionine analog.

13. A method of determining whether a cytosine present at a predefined position within a single strand of a double-stranded DNA of known sequence is non-methylated comprising:

a) contacting the double-stranded DNA with a CpG methyltransferase and an S-adenosylmethionine analog having the structure:

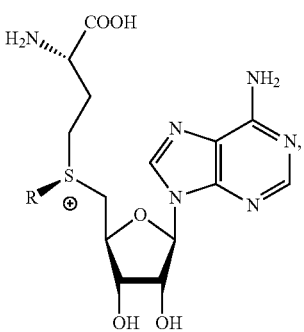

wherein R (1) is a chemical group capable of (i) being transferred from the S-adenosylmethionine analog by the CpG methyltransferase to the 5 carbon of each non-methylated cytosine within the double-stranded DNA and (ii) forming a covalent bond between the chemical group and the 5 carbon of each such non-methylated cytosine within the double-stranded DNA, thereby producing a derivative of the double stranded DNA and (2) has one of the following structures:

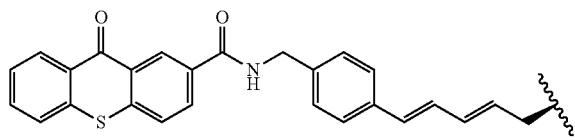

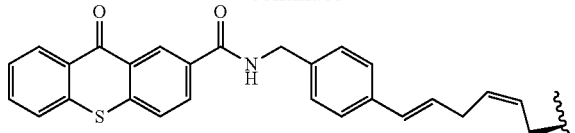

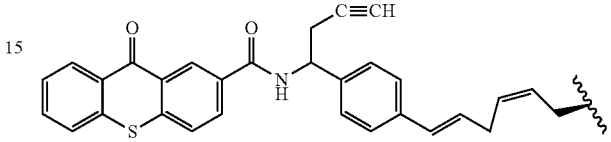

or b) photoirradiating the derivative of the double-stranded DNA at a wavelength greater than 330 nm up to 700 nm so as to photocatalytically convert each cytosine to which the chemical group R is covalently bound to a uracil analog;

c) separately obtaining the single strand from the photoirradiated derivative of the double-stranded DNA;

d) determining the sequence of the single strand so obtained in step c); and e) comparing the sequence of the single strand determined in step d) to the sequence of the single strand of the double-stranded DNA prior to performing steps a-d, wherein the presence of a uracil analog at the predefined position within the single strand of the photoirradiated derivative of the double-stranded DNA indicates that the cytosine at that position in the single strand of the double stranded DNA of known sequence is non-methylated.

14. The method of claim 13, wherein the CpG methyltransferase is the mutant M.SssI methyltransferase comprising relative to non-mutant M.SssI methyltransferase from *E. coli* K12 strain ER1821 (i) substitution of serine for the amino acid Q142 and (ii) substitution of serine for the amino acid N370.

* * * * *

SEQUENCE LISTING

```
<160> NUMBER OF SEQ ID NOS: 40

<210> SEQ ID NO 1
<211> LENGTH: 15
<212> TYPE: DNA
<213> ORGANISM: Artificial Sequence
<220> FEATURE:
<223> OTHER INFORMATION: Sequence is synthesized
<220> FEATURE:
<221> NAME/KEY: modified_base
<222> LOCATION: (6)..(6)
<223> OTHER INFORMATION: 5-All-OMC

<400> SEQUENCE: 1
tacgagagtg cggca                                              15

<210> SEQ ID NO 2
<211> LENGTH: 10
<212> TYPE: DNA
<213> ORGANISM: Artificial Sequence
<220> FEATURE:
<223> OTHER INFORMATION: Sequence is synthesized

<400> SEQUENCE: 2
tgccgcactc                                                    10

<210> SEQ ID NO 3
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 3
tacgacgagt gcggca                                             16

<210> SEQ ID NO 4
<211> LENGTH: 64
<212> TYPE: DNA
<213> ORGANISM: Artificial Sequence
<220> FEATURE:
<223> OTHER INFORMATION: Sequence is synthesized

<400> SEQUENCE: 4
ataccctgtt gagataagtc tgcacaagga aatgaatatg ttaataaatc tatattttc  60 aaag                                                              64
```

<210> SEQ ID NO 5
<211> LENGTH: 64
<212> TYPE: DNA
<213> ORGANISM: Artificial Sequence
<220> FEATURE:
<223> OTHER INFORMATION: Sequence is synthesized

<400> SEQUENCE: 5
ctttgaaaaa tatagattta ttaacatatt catttccttg tgcagactta tctcaacagg    60
gtat    64

<210> SEQ ID NO 6
<211> LENGTH: 60
<212> TYPE: DNA
<213> ORGANISM: Artificial Sequence
<220> FEATURE:
<223> OTHER INFORMATION: Sequence is synthesized

<400> SEQUENCE: 6
tcgcttccaa aacttctact gatattgaag ctccacaaac aaatattttt tgattttcag    60

<210> SEQ ID NO 7
<211> LENGTH: 60
<212> TYPE: DNA
<213> ORGANISM: Artificial Sequence
<220> FEATURE:
<223> OTHER INFORMATION: Sequence is synthesized

<400> SEQUENCE: 7
ctgaaaatca aaaatatttt gtttgtggag cttcaatatc agtagaagtt ttggaagcga    60

<210> SEQ ID NO 8
<211> LENGTH: 49
<212> TYPE: DNA
<213> ORGANISM: Artificial Sequence
<220> FEATURE:
<223> OTHER INFORMATION: Sequence is synthesized

<400> SEQUENCE: 8
ttattaacat attcatttcc ttgttcagac ttatctcaac agggtattc    49

<210> SEQ ID NO 9
<211> LENGTH: 49
<212> TYPE: DNA
<213> ORGANISM: Artificial Sequence
<220> FEATURE:
<223> OTHER INFORMATION: Sequence is synthesized

<400> SEQUENCE: 9
gaataccctg ttgagataag tctgaacaag gaaatgaata tgttaataa    49

<210> SEQ ID NO 10
<211> LENGTH: 58
<212> TYPE: DNA
<213> ORGANISM: Artificial Sequence
<220> FEATURE:
<223> OTHER INFORMATION: Sequence is synthesized

<400> SEQUENCE: 10
tgaaaatcaa aaatatttg tttgtggaag ttcaatatca gtagaagttt tggaagcg    58

<210> SEQ ID NO 11
<211> LENGTH: 58
<212> TYPE: DNA
<213> ORGANISM: Artificial Sequence
<220> FEATURE:
<223> OTHER INFORMATION: Sequence is synthesized

<400> SEQUENCE: 11
cgcttccaaa acttctactg atattgaact tccacaaaca atatttttt gattttca        58

<210> SEQ ID NO 12
<211> LENGTH: 56
<212> TYPE: DNA
<213> ORGANISM: Artificial Sequence
<220> FEATURE:
<223> OTHER INFORMATION: Sequence is synthesized

<400> SEQUENCE: 12
gcttccaaaa cttctactga tattgaattt ccacaaacaa atatttttg attttc          56

<210> SEQ ID NO 13
<211> LENGTH: 56
<212> TYPE: DNA
<213> ORGANISM: Artificial Sequence
<220> FEATURE:
<223> OTHER INFORMATION: Sequence is synthesized

<400> SEQUENCE: 13
gaaaatcaaa aaatatttgt tgtggaaat tcaatatcag tagaagtttt ggaagc          56

<210> SEQ ID NO 14
<211> LENGTH: 58
<212> TYPE: DNA
<213> ORGANISM: Artificial Sequence
<220> FEATURE:
<223> OTHER INFORMATION: Sequence is synthesized

<400> SEQUENCE: 14
cttttgaata ccctgttgag ataagtcttg acaaggaaat gaatatgtta ataaatct      58

<210> SEQ ID NO 15
<211> LENGTH: 58
<212> TYPE: DNA
<213> ORGANISM: Artificial Sequence
<220> FEATURE:
<223> OTHER INFORMATION: Sequence is synthesized

<400> SEQUENCE: 15
agatttatta acatattcat ttccttgtca agacttatct caacagggta ttcaaaag      58

<210> SEQ ID NO 16
<211> LENGTH: 56
<212> TYPE: DNA
<213> ORGANISM: Artificial Sequence
<220> FEATURE:
<223> OTHER INFORMATION: Sequence is synthesized

<400> SEQUENCE: 16
gaaacagacc atgcaccatc accaccacca tagcaaagta gaaataaaa caaaaa          56

<210> SEQ ID NO 17
<211> LENGTH: 37
<212> TYPE: DNA
<213> ORGANISM: Artificial Sequence
<220> FEATURE:
<223> OTHER INFORMATION: Sequence is synthesized

<400> SEQUENCE: 17
gtgcatggtc tgtttcctgt gtgaaattgt tatccgc                              37

<210> SEQ ID NO 18
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 18
ttccttgtca agact                                                        15

<210> SEQ ID NO 19
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 19
tttgtggaaa ttcaat                                                       16

<210> SEQ ID NO 20
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 20
ttccttgttc agactt                                                       16

<210> SEQ ID NO 21
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 21
tttgtggaag ttcaat                                                       16

<210> SEQ ID NO 22
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 22
ttccttgttc agactt                                                       16

<210> SEQ ID NO 23
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 23
tttgtggagc ttcaa                                                        15

<210> SEQ ID NO 24
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 24
ttccttgtgc agact					15

<210> SEQ ID NO 25
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 25
tttgtggaag ttcaat					16

<210> SEQ ID NO 26
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 26
ttccttgtgc agact					15

<210> SEQ ID NO 27
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 27
tttgtggagc ttcaa					15

<210> SEQ ID NO 28
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 28
ttccttgtca agact					15

<210> SEQ ID NO 29
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 29
tttgtggagc ttcaa					15

<210> SEQ ID NO 30
<211> LENGTH: 15
<212> TYPE: DNA
<213> ORGANISM: Artificial Sequence
<220> FEATURE:
<223> OTHER INFORMATION: Sequence is synthesized

<400> SEQUENCE: 30
ttccttgtca agact					15

<210> SEQ ID NO 31

```
<211> LENGTH: 16
<212> TYPE: DNA
<213> ORGANISM: Artificial Sequence
<220> FEATURE:
<223> OTHER INFORMATION: Sequence is synthesized

<400> SEQUENCE: 31
tttgtggaag ttcaat                                                    16

<210> SEQ ID NO 32
<211> LENGTH: 25
<212> TYPE: DNA
<213> ORGANISM: Artificial Sequence
<220> FEATURE:
<223> OTHER INFORMATION: Sequence is synthesized

<400> SEQUENCE: 32
atgcatcatc accaccacca ctagc                                          25

<210> SEQ ID NO 33
<211> LENGTH: 51
<212> TYPE: DNA
<213> ORGANISM: Artificial Sequence
<220> FEATURE:
<223> OTHER INFORMATION: Sequence is synthesized
<220> FEATURE:
<221> NAME/KEY: modified_base
<222> LOCATION: (24)..(24)
<223> OTHER INFORMATION: photo-convertible 5-modified cytosine

<400> SEQUENCE: 33
agcacggata cgtaggaact gaccggagac tgggcgccat ggatccgtac t             51

<210> SEQ ID NO 34
<211> LENGTH: 51
<212> TYPE: DNA
<213> ORGANISM: Artificial Sequence
<220> FEATURE:
<223> OTHER INFORMATION: Sequence is synthesized
<220> FEATURE:
<221> NAME/KEY: modified_base
<222> LOCATION: (27)..(27)
<223> OTHER INFORMATION: photo-convertible 5-modified cytosine

<400> SEQUENCE: 34
agtacggatc catggcgccc agtctccggt cagttcctac gtatccgtgc t             51

<210> SEQ ID NO 35
<211> LENGTH: 51
<212> TYPE: DNA
<213> ORGANISM: Artificial Sequence
<220> FEATURE:
<223> OTHER INFORMATION: Sequence is synthesized
<220> FEATURE:
<221> NAME/KEY: modified_base
<222> LOCATION: (24)..(24)
<223> OTHER INFORMATION: photo-convertible 5-modified cytosine

<400> SEQUENCE: 35
agcacggata cgtaggaact gaccggagac tgggcgccat ggatccgtac t             51

<210> SEQ ID NO 36
<211> LENGTH: 51
<212> TYPE: DNA
<213> ORGANISM: Artificial Sequence
<220> FEATURE:
<223> OTHER INFORMATION: Sequence is synthesized
<220> FEATURE:
<221> NAME/KEY: modified_base
```

```
<222> LOCATION: (27)..(27)
<223> OTHER INFORMATION: photo-convertible 5-modified cytosine

<400> SEQUENCE: 36
agtacggatc catggcgccc agtctccggt cagttcctac gtatccgtgc t        51

<210> SEQ ID NO 37
<211> LENGTH: 51
<212> TYPE: DNA
<213> ORGANISM: Artificial Sequence
<220> FEATURE:
<223> OTHER INFORMATION: Sequence is synthesized
<220> FEATURE:
<221> NAME/KEY: modified_base
<222> LOCATION: (24)..(24)
<223> OTHER INFORMATION: U analog
<220> FEATURE:
<221> NAME/KEY: misc_feature
<222> LOCATION: (24)..(24)
<223> OTHER INFORMATION: n is a, c, g, or t

<400> SEQUENCE: 37
agcacggata cgtaggaact gacnggagac tgggcgccat ggatccgtac t         51

<210> SEQ ID NO 38
<211> LENGTH: 51
<212> TYPE: DNA
<213> ORGANISM: Artificial Sequence
<220> FEATURE:
<223> OTHER INFORMATION: Sequence is synthesized
<220> FEATURE:
<221> NAME/KEY: modified_base
<222> LOCATION: (27)..(27)
<223> OTHER INFORMATION: U analog
<220> FEATURE:
<221> NAME/KEY: misc_feature
<222> LOCATION: (27)..(27)
<223> OTHER INFORMATION: n is a, c, g, or t

<400> SEQUENCE: 38
agtacggatc catggcgccc agtctcnggt cagttcctac gtatccgtgc t         51

<210> SEQ ID NO 39
<211> LENGTH: 51
<212> TYPE: DNA
<213> ORGANISM: Artificial Sequence
<220> FEATURE:
<223> OTHER INFORMATION: Sequence is synthesized

<400> SEQUENCE: 39
agcacggata cgtaggaact gactagagac tgggcgccat ggatccgtac t         51

<210> SEQ ID NO 40
<211> LENGTH: 51
<212> TYPE: DNA
<213> ORGANISM: Artificial Sequence
<220> FEATURE:
<223> OTHER INFORMATION: Sequence is synthesized

<400> SEQUENCE: 40
agtacggatc catggcgccc agtctctagt cagttcctac gtatccgtgc t         51
```